US007935811B2

(12) United States Patent
Robertson et al.

(10) Patent No.: US 7,935,811 B2
(45) Date of Patent: *May 3, 2011

(54) APPARATUS AND SYSTEM HAVING DRY GENE SILENCING COMPOSITIONS

(75) Inventors: Barbara Robertson, Boulder, CO (US);
Devin Leake, Denver, CO (US);
Kathryn Robinson, Golden, CO (US);
William S. Marshall, Boulder, CO (US);
Anastasia Khvorova, Boulder, CO (US)

(73) Assignee: Dharmacon, Inc., Lafayette, CO (US)

( * ) Notice: Subject to any disclaimer, the term of this patent is extended or adjusted under 35 U.S.C. 154(b) by 0 days.
This patent is subject to a terminal disclaimer.

(21) Appl. No.: 11/283,484

(22) Filed: Nov. 18, 2005

(65) Prior Publication Data
US 2006/0115461 A1 Jun. 1, 2006

Related U.S. Application Data

(60) Provisional application No. 60/630,320, filed on Nov. 22, 2004, provisional application No. 60/678,165, filed on May 4, 2005.

(51) Int. Cl.
*C07H 21/04* (2006.01)
*A61K 31/70* (2006.01)
*C40B 40/06* (2006.01)

(52) U.S. Cl. ........... 536/24.5; 536/23.1; 514/44; 506/16
(58) Field of Classification Search ........................ None
See application file for complete search history.

(56) References Cited

U.S. PATENT DOCUMENTS

| | | | |
|---|---|---|---|
| 4,924,624 A | 5/1990 | Suhadolnik et al. |
| 5,023,243 A | 6/1991 | Tullis |
| 5,138,045 A | 8/1992 | Cook et al. |
| 5,151,510 A | 9/1992 | Stec et al. |
| 5,166,320 A | 11/1992 | Wu et al. |
| 5,214,136 A | 5/1993 | Lin |
| 5,264,562 A | 11/1993 | Matteucci |
| 5,264,564 A | 11/1993 | Matteucci |
| 5,286,717 A | 2/1994 | Cohen |
| 5,399,676 A | 3/1995 | Froehler |
| 5,414,077 A | 5/1995 | Lin |
| 5,434,257 A | 7/1995 | Matteucci |
| 5,457,191 A | 10/1995 | Cook |
| 5,457,527 A | 10/1995 | Manns et al. |
| 5,459,255 A | 10/1995 | Cook |
| 5,484,908 A | 1/1996 | Swaminathan |
| 5,487,872 A | 1/1996 | Hafeman et al. |
| 5,489,677 A | 2/1996 | Sanghvi |
| 5,502,177 A | 3/1996 | Matteucci |
| 5,514,786 A | 5/1996 | Cook |
| 5,532,130 A | 7/1996 | Alul |
| 5,578,718 A | 11/1996 | Cook |
| 5,580,767 A | 12/1996 | Cowsert et al. |
| 5,587,361 A | 12/1996 | Cook |
| 5,587,469 A | 12/1996 | Cook |
| 5,587,470 A | 12/1996 | Cook |
| 5,591,721 A | 1/1997 | Agrawal |
| 5,594,121 A | 1/1997 | Froehler |
| 5,596,086 A | 1/1997 | Matteucci |
| 5,608,046 A | 3/1997 | Cook |
| 5,610,289 A | 3/1997 | Cook |
| 5,614,617 A | 3/1997 | Cook |
| 5,635,488 A | 6/1997 | Cook |
| 5,637,573 A | 6/1997 | Agrawal |
| 5,644,048 A | 7/1997 | Yau |
| 5,645,985 A | 7/1997 | Froehler |
| 5,652,355 A | 7/1997 | Metelev |
| 5,652,356 A | 7/1997 | Agrawal |
| 5,658,731 A | 8/1997 | Sproat |
| 5,670,633 A | 9/1997 | Cook |
| 5,674,108 A | 10/1997 | Rolle |
| 5,674,908 A | 10/1997 | Haces et al. |
| 5,677,437 A | 10/1997 | Teng |
| 5,681,941 A | 10/1997 | Cook |
| 5,708,161 A | 1/1998 | Reese |
| 5,734,041 A | 3/1998 | Just |
| 5,750,666 A | 5/1998 | Caruthers |

(Continued)

FOREIGN PATENT DOCUMENTS

EP 1114623 10/2001

(Continued)

OTHER PUBLICATIONS

Ambion webpage for custom siRNA synthesis, Nov. 29, 2002 as provided by the Internet Archive Wayback Machine [retrieved Sep. 11, 2009]. Retrieved from the internet: <URL http://web.archive.org/web/20021213193808/www.ambion.com/catalog/ProdGrp.html?fkApp=25&fkProdGrp=247&srcd=fpr0209a>.*
Vermeulen, A. et al., "The contributions of dsRNA structure to Dicer specificity and efficiency"; RNA,11:674-682 (2005).
*Atlas Venture*, Dharmacon and Akceli Announce Research Collaboration to Combine Reverse Transfection and siRNA for High Throughput Gene Silencing, www.atlasventure.com/home/news_content.asp?ne_id=1741 (Aug. 24, 2004).
Ambion, High Throughput siRNA Deliery in Vitro: From Cell Lines to Pimrary. Cells, TechNotes 12(2); ww.ambion.com/techlib/tn/122/3.html (downloaded Jul. 18, 2005).
*Boston Business Journal*, "Biotech firm Akceli wins first patent," www.bizhournals.com/boston/stories/2003/04/07/daily13.html.
Dhellin, Olivier et al., "Functional differences between the human LINE retrotransposon and retroviral revsere transcriptases for in vivo mRNA reverse transcription," The EMBO Journal, vol. 16, pp. 6590-6602; 1997.

(Continued)

*Primary Examiner* — Tracy Vivlemore
(74) *Attorney, Agent, or Firm* — Workman Nydegger

(57) ABSTRACT

A reverse transfection apparatus can be used for introducing siRNA into a cell to effect gene silencing. Such an apparatus can include a well plate having a well configured for transfecting cells. The well can include a substantially dry gene silencing composition that has at least a first siRNA which silences a first target gene. The gene silencing composition can be configured such that the at least first siRNA is capable of being solubilized or suspended in an aqueous medium in an amount sufficient for transfecting cells in the well. Additionally, the at least first siRNA can include a modification or a conjugate. The reverse transfection apparatus can be provided as a kit or system that additionally includes cells, polynucleotide carriers, reverse transfection reagents, and the like.

8 Claims, 34 Drawing Sheets

U.S. PATENT DOCUMENTS

| | | |
|---|---|---|
| 5,756,710 A | 5/1998 | Stein |
| 5,757,710 A | 5/1998 | Li-Chun |
| 5,763,588 A | 6/1998 | Metteucci |
| 5,767,264 A | 6/1998 | Otlvos |
| 5,770,713 A | 6/1998 | Imbach |
| 5,773,601 A | 6/1998 | Agrawal |
| 5,777,092 A | 7/1998 | Cook |
| 5,792,844 A | 8/1998 | Sangvhi |
| 5,792,847 A | 8/1998 | Bhur |
| 5,811,274 A | 9/1998 | Palsson |
| 5,811,534 A | 9/1998 | Cook |
| 5,817,781 A | 10/1998 | Swaminathan |
| 5,830,653 A | 11/1998 | Froehler |
| 5,834,439 A | 11/1998 | Haces et al. |
| 5,834,607 A | 11/1998 | Manoharan |
| 5,849,902 A | 12/1998 | Arrow |
| 5,852,182 A | 12/1998 | Cook |
| 5,852,188 A | 12/1998 | Cook |
| 5,856,455 A | 1/1999 | Cook |
| 5,859,221 A | 1/1999 | Cook |
| 5,872,232 A | 2/1999 | Cook |
| 5,883,237 A | 3/1999 | Stec |
| 5,889,136 A | 3/1999 | Scaringe et al. |
| 5,898,031 A | 4/1999 | Crooke |
| 5,912,339 A | 6/1999 | Miller |
| 5,914,396 A | 6/1999 | Cook |
| 5,919,619 A | 7/1999 | Tullis |
| 5,948,903 A | 9/1999 | Cook |
| 5,965,722 A | 10/1999 | Ecker |
| 5,973,136 A | 10/1999 | Agrawal |
| 5,989,835 A | 11/1999 | Dunlay et al. |
| 5,989,912 A | 11/1999 | Arrow |
| 5,998,203 A | 12/1999 | Matulic-adamic |
| 5,998,206 A | 12/1999 | Cowsert |
| 6,005,087 A | 12/1999 | Cook |
| 6,005,094 A | 12/1999 | Simon |
| 6,005,096 A | 12/1999 | Matteucci |
| 6,007,992 A | 12/1999 | Lin |
| 6,008,400 A | 12/1999 | Scaringe et al. |
| 6,028,183 A | 2/2000 | Lin |
| 6,043,352 A | 3/2000 | Manoharan |
| 6,060,592 A | 5/2000 | Acevedo |
| 6,110,916 A | 8/2000 | Haces et al. |
| 6,111,085 A | 8/2000 | Cook |
| 6,111,086 A | 8/2000 | Scaringe |
| 6,114,513 A | 9/2000 | Cook |
| 6,127,533 A | 10/2000 | Cook |
| 6,140,482 A | 10/2000 | Lyer |
| 6,143,881 A | 11/2000 | Metelev |
| 6,147,200 A | 11/2000 | Manoharan |
| 6,153,737 A | 11/2000 | Manoharan |
| 6,166,188 A | 12/2000 | Cook |
| 6,166,197 A | 12/2000 | Cook |
| 6,172,209 B1 | 1/2001 | Manoharan |
| 6,197,944 B1 | 3/2001 | Walder |
| 6,204,027 B1 | 3/2001 | Goodchild |
| 6,222,025 B1 | 4/2001 | Cook |
| 6,235,886 B1 | 5/2001 | Manoharan |
| 6,239,265 B1 | 5/2001 | Cook |
| 6,242,589 B1 | 6/2001 | Cook |
| 6,242,591 B1 | 6/2001 | Cole |
| 6,265,558 B1 | 7/2001 | Cook |
| 6,271,358 B1 | 8/2001 | Manoharan |
| 6,277,967 B1 | 8/2001 | Manoharan |
| 6,277,982 B1 | 8/2001 | Fraser |
| 6,300,319 B1 | 10/2001 | Manoharan |
| 6,307,040 B1 | 10/2001 | Cook |
| 6,322,987 B1 | 11/2001 | Cook |
| 6,326,358 B1 | 12/2001 | Manoharan |
| 6,331,441 B1 | 12/2001 | Balch et al. |
| 6,335,437 B1 | 1/2002 | Manoharan |
| 6,346,614 B1 | 2/2002 | Metelev et al. |
| 6,348,312 B1 | 2/2002 | Peyman |
| 6,358,931 B1 | 3/2002 | Cook |
| 6,359,124 B1 | 3/2002 | Ecker |
| 6,369,040 B1 | 4/2002 | Acevedo |
| 6,369,209 B1 | 4/2002 | Manoharan |
| 6,380,368 B1 | 4/2002 | Froehler |
| 6,391,636 B1 | 5/2002 | Monia |
| 6,395,492 B1 | 5/2002 | Manoharan et al. |
| 6,399,297 B1 | 6/2002 | Baker |
| 6,399,663 B1 | 6/2002 | Haces et al. |
| 6,403,781 B2 | 6/2002 | Cole |
| 6,410,702 B1 | 6/2002 | Swaminathan |
| 6,414,127 B1 | 7/2002 | Lin |
| 6,416,959 B1 | 7/2002 | Giuliano et al. |
| 6,420,546 B1 | 7/2002 | Seliger |
| 6,440,943 B1 | 8/2002 | Cook |
| 6,447,998 B1 | 9/2002 | Froehler |
| 6,451,991 B1 | 9/2002 | Martin |
| 6,458,940 B2 | 10/2002 | Roberts |
| 6,476,205 B1 | 11/2002 | Bhur |
| 6,485,974 B1 | 11/2002 | Papoff |
| 6,495,672 B1 | 12/2002 | Froehler |
| 6,506,559 B1 | 1/2003 | Fire |
| 6,514,464 B1 | 2/2003 | Knebel |
| 6,525,031 B2 | 2/2003 | Manoharan |
| 6,531,584 B1 | 3/2003 | Cook |
| 6,534,639 B1 | 3/2003 | Manoharan |
| 6,544,790 B1 | 4/2003 | Sabatini |
| 6,573,039 B1 | 6/2003 | Dunlay et al. |
| 6,576,752 B1 | 6/2003 | Manoharan |
| 6,590,093 B1 | 7/2003 | Scaringe |
| 6,600,032 B1 | 7/2003 | Manoharan |
| 6,608,035 B1 | 8/2003 | Agrawal |
| 6,620,591 B1 | 9/2003 | Dunlay et al. |
| 6,624,293 B1 | 9/2003 | Agrawal |
| 6,645,943 B1 | 11/2003 | Agrawal |
| 6,653,458 B1 | 11/2003 | Manoharan |
| 6,671,624 B1 | 12/2003 | Dunlay et al. |
| 6,673,611 B2 | 1/2004 | Thompson |
| 6,677,445 B1 | 1/2004 | Innis |
| 6,683,167 B2 | 1/2004 | Metelev |
| 6,716,582 B2 | 4/2004 | Gonye et al. |
| 6,716,588 B2 | 4/2004 | Sammak et al. |
| 6,716,882 B2 | 4/2004 | Haces et al. |
| 6,759,206 B1 | 7/2004 | Rubin et al. |
| 6,809,193 B2 | 10/2004 | McKay |
| 6,811,975 B2 | 11/2004 | Cook |
| 6,841,542 B2 | 1/2005 | Bartlemez |
| 6,846,921 B2 | 1/2005 | Innis |
| 6,875,578 B2 | 4/2005 | Giuliano et al. |
| 6,881,831 B2 | 4/2005 | Lyer |
| 6,902,883 B2 | 6/2005 | Dunlay et al. |
| 6,924,109 B2 | 8/2005 | Melcher et al. |
| 6,936,467 B2 | 8/2005 | Kmiec |
| 6,951,757 B2 * | 10/2005 | Sabatini ................ 435/455 |
| 6,958,239 B2 | 10/2005 | Arrow |
| 6,977,245 B2 | 12/2005 | Klinman |
| 7,045,609 B2 | 5/2006 | Metelev |
| 7,067,497 B2 | 6/2006 | Hanecak |
| 7,078,196 B2 | 7/2006 | Tuschl |
| 7,173,014 B2 | 2/2007 | Agrawal |
| 7,595,387 B2 | 9/2009 | Leake et al. |
| 2002/0006664 A1 | 1/2002 | Sabatini |
| 2002/0128466 A1 | 9/2002 | Cole |
| 2002/0160379 A1 | 10/2002 | Cook |
| 2003/0036516 A1 | 2/2003 | Agrawal |
| 2003/0045698 A1 | 3/2003 | Manoharan |
| 2003/0096770 A1 | 5/2003 | Krotz |
| 2003/0135033 A1 | 7/2003 | Klippel-Giese |
| 2003/0170642 A1 | 9/2003 | Caldwell et al. |
| 2003/0170891 A1 * | 9/2003 | McSwiggen ............ 435/366 |
| 2003/0190626 A1 | 10/2003 | Ravikumar |
| 2003/0203486 A1 | 10/2003 | Sabatini |
| 2003/0206887 A1 | 11/2003 | Morrissey |
| 2003/0228601 A1 | 12/2003 | Sabatini |
| 2003/0228694 A1 | 12/2003 | Sabatini |
| 2004/0009938 A1 | 1/2004 | Manoharan |
| 2004/0014108 A1 | 1/2004 | Eldrup |
| 2004/0014956 A1 * | 1/2004 | Woolf et al. ............. 536/23.1 |
| 2004/0014957 A1 | 1/2004 | Eldrup |
| 2004/0019008 A1 * | 1/2004 | Lewis et al. ............... 514/44 |
| 2004/0043948 A1 | 3/2004 | Baker |
| 2004/0053875 A1 | 3/2004 | Kruetzer |
| 2004/0054155 A1 | 3/2004 | Woolf |
| 2004/0058886 A1 | 3/2004 | Scaringe |

| | | | |
|---|---|---|---|
| 2004/0072779 A1 | 4/2004 | Kruetzer | |
| 2004/0096880 A1 | 5/2004 | Kmiec | |
| 2004/0102408 A1 | 5/2004 | Kruetzer | |
| 2004/0110296 A1 | 6/2004 | Vargeese | |
| 2004/0137064 A1 | 7/2004 | Lewis et al. | |
| 2004/0147022 A1 | 7/2004 | Baker | |
| 2004/0147023 A1 | 7/2004 | Baker | |
| 2004/0167090 A1 | 8/2004 | Monaharan | |
| 2004/0180351 A1 | 9/2004 | Giese | |
| 2004/0198640 A1 | 10/2004 | Leake | |
| 2004/0204420 A1 | 10/2004 | Rana | |
| 2004/0248299 A1 | 12/2004 | Jayasena | |
| 2004/0259247 A1 | 12/2004 | Tuschl et al. | |
| 2004/0266707 A1 | 12/2004 | Leake et al. | |
| 2005/0020521 A1 | 1/2005 | Rana | |
| 2005/0020525 A1 | 1/2005 | McSwiggen | |
| 2005/0026160 A1 | 2/2005 | Allerson | |
| 2005/0059044 A1 | 3/2005 | Graham | |
| 2005/0123571 A1* | 6/2005 | Rossini et al. | 424/277.1 |
| 2005/0130181 A1 | 6/2005 | McSwiggen | |
| 2005/0181385 A1 | 8/2005 | Linsley | |
| 2005/0223427 A1 | 10/2005 | Leake | |
| 2005/0239728 A1 | 10/2005 | Pachuk et al. | |
| 2005/0255487 A1 | 11/2005 | Khorova | |
| 2006/0127891 A1 | 6/2006 | McSwiggen | |
| 2006/0178324 A1 | 8/2006 | Hadwiger | |
| 2006/0223777 A1 | 10/2006 | Vermeulen | |
| 2007/0141134 A1 | 6/2007 | Kosak | |
| 2007/0167384 A1 | 7/2007 | Leake | |
| 2007/0173476 A1 | 7/2007 | Leake | |
| 2007/0269889 A1 | 11/2007 | Leake | |

FOREIGN PATENT DOCUMENTS

| | | |
|---|---|---|
| EP | 1389637 | 2/2004 |
| EP | 1559785 | 8/2005 |
| EP | 1814895 | 8/2007 |
| WO | 93-04204 | 3/1993 |
| WO | 94-01550 | 1/1994 |
| WO | 94-21825 | 9/1994 |
| WO | 94-26887 | 11/1994 |
| WO | WO 97/30731 | 8/1997 |
| WO | WO9742819 | 11/1997 |
| WO | 99-32619 | 7/1999 |
| WO | WO0012454 | 3/2000 |
| WO | WO0120015 | 3/2001 |
| WO | 01-75164 | 10/2001 |
| WO | 02-44321 | 6/2002 |
| WO | 02-094185 | 11/2002 |
| WO | 03-064625 | 8/2003 |
| WO | 03-064626 | 8/2003 |
| WO | 03-070193 | 8/2003 |
| WO | 03-070918 | 8/2003 |
| WO | 03-072705 A2 | 9/2003 |
| WO | 03-072705 A3 | 9/2003 |
| WO | 03-074654 | 9/2003 |
| WO | 2004-015107 A2 | 2/2004 |
| WO | 2004-015107 A3 | 2/2004 |
| WO | WO2004011624 | 2/2004 |
| WO | WO2004045543 | 6/2004 |
| WO | 2004-080406 | 9/2004 |
| WO | WO2004078946 | 9/2004 |
| WO | 2004-091515 | 10/2004 |
| WO | WO2004090105 | 10/2004 |
| WO | 2004-109290 | 12/2004 |
| WO | 2005-019453 | 3/2005 |
| WO | WO 2005/039645 | 5/2005 |
| WO | WO2005078094 | 8/2005 |
| WO | WO2005097992 | 10/2005 |

OTHER PUBLICATIONS

Press Release, Dharmacon Launches siArray RTF™ siRNA Libraries—First-Ever Using Reverse Transfection Technology, qb Perbio Solutions for Life Science; Layfayette, Colo.; Apr. 22, 2005.
Hannon, Gregory J., "RNA Interference," Nature, vol. 418; Jul. 11, 2002. (www.nature.com/nature).
Ketting, R.F. et al. (2001) Dicer Functions in RNA Interference and in Synthesis of Small RNA Involved in Developmental Timing in C. elegans Genes Dev., Oct. 15, 2001, 15(20):2654-9.
Paddison, P. J., et al., "A resource for large-scale RNA-interference-based screens in mammals," Nature, vol. 428; Mar. 25, 2004 (www.nature.com/nature).
He, L. et al., "MicroRNAs: Small RNAs with a Big Role in Gene Regulation," Nature, vol. 5, pp. 522-532; Jul. 2004 (www.nature.com/reviews/genetics).
Hannon, G.J., et al., "Unlocking the Potential of the Human Genome with RNA Interference," Nature, vol. 431; Sep. 16, 2004 (www.nature.com/nature).
Hammond, S.M., et al., "Post-Transcriptional Gene Silencing by Double-Stranded RNA," Nature, vol. 2; Feb. 2001 (www.nature.com/reviews/genetics).
Hannon, G., "Growth control in mammalian cells: post-transcriptional gene silencing," (www.cshl.org/public/SCIENCE/hannon.html) (2004).
Denli, A.M., et al., "RNAi: an ever-growing puzzle," Trends in Biochemical Sciences, vol. 28, No. 4, Apr. 2003.
Silva, J.M., et al., "RNA interference: a promising approach to antiviral therapy?" Trends in Molecular Medicine, vol. 8, No. 11, Nov. 2002.
Qiagen Website (www.qiagen.com), Transfection Cell Database, Using siRNA (dsRNA) as Nucleic Acid, Cell Records.
"The HiPerformance algorithm designs highly potent and specific siRNA", Technical Information, www1.qiagen.com/literature/resources/RNAi/1030174_TI_GS_siRNA_0105.-pdf; downloaded Jul. 18, 2005.
Ziauddin, J. et al., "Microarrays of cells expressing defined cDNAs," Letters to Nature, Nature, 411, pp. 107-110 (May 3, 2001); doi:10.1038/35075114.
Reverse Transfection Homepage and Guide, Ziauddin, J. and Sabatini, D., http://staffa.wi.mit.edu/sabatini_public/reverse/transfection/content (downloaded Aug. 24, 2004).
Product Insert, siARRAY™ siRNA Libraries, Version 2.0; Dharmacon RNA Technologies.
SuperArray Bioscience Corporation, Introducing siRNA Array Plates, www.supperarray.com/RNAiArrayPlates.php (downloaded Jul. 18, 2005).
SuperArray Bioscience Corporation, siRNA Array Plates, www.supperarray.com/manuals/Present_ArrayPlates.pdf (downloaded Jul. 18, 2005).
SuperArray Bioscience Corporation, Newly Released SureSilencing™ Mouse siRNA Products, www.supperarray.com/siRNAnew.php?sp=Mouse (downloaded Jul. 18, 2005).
SuperArray Bioscience Corporation, Newly Released SureSilencing™ Human siRNA Products, www.supperarray.com/siRNAnew.php?sp=Human (downloaded Jul. 18, 2005).
Qiagen, Transfection Reagent Selector Kit Handbook, Jan. 1999.
Bernstein, E., et al., "The rest is silence," RNA (2001), 7:1509-1521. Cambridge University Press.
Mousses et al., PNAi Microarray Analysis in Cultured Mammalian Cells. Genome Research 2003, vol. 13, pp. 2341-2347.
Vanhecke et al., High-Throughput Gene Silencing Using Cell Arrays, Oncogene Nov. 1, 2004 vol. 23, pp. 8353-8358.
U.S. Appl. No. 11/857,732, filed Sep. 19, 2007, Khvorova.
Amarzguioui et al., Tolerance for Mutations and Chemical Modifications in siRNA, 2003, Nucleic Acids Research, vol. 31, No. 2, pp. 589-595 Oxford University Press.
Parrish et al., Functional Anatomy of a dsRNA Trigger: Differential Requirement for the Two Trigger Strands in RNA Interference, Nov. 2000, Molecular Cell, vol. 6, pp. 1077-1087.
Elbashir et al., RNA Interference is Mediated by 21- and 22-Nucleotide RNAs, Jan. 2001, Genes & Development, vol. 15, pp. 188-200.
Letsinger et al., Cholesteryl-conjugated Oligonucleotides: Synthesis, properties, and activity as inhibitors of replication of human immunodeficiency virus in cell culture, Sep. 1989, Proc. Natl. Acad. Sci. vol. 86, pp. 6553-6556.
Boiziau et al. (1995) Antisense 2"-O-alkyl Oligoribinucleotides are efficient inhibitors of reverse transcription, Nucleic Acids Res. 23/1:64-71.
Chiu et al. (2003) siRNA function in RNAi: A Chemical Modification Analysis, RNA 9/9:1034-1048.

Conrad et al. (1995) Enzymatic synthesis of 2'-modified nucleic acids: identification of important phosphate and ribose moieties in Rnase P substrates, Nucleic Acids Res. 23/11:1845-1853.

Czauderna et al. (2003) Structural Variations and Stabilizing modifications of synthetic siRNAs in mammalian cells, Nucleic Acids Res. 31/11:2705-2716.

Grunweller et al. (2003) Comparison of different antisense strategies in mammalian cells using locked nucleic acid, 2'-O-methyl RNA, phosphorothioates and small interfering RNA, Nucleic Acids Res. 31/12:3185-3193.

Holen et al. (2003) Similar behavior of single-strand and double-strand siRNAs suggests they act through a common RNAi pathway, Nucleic Acids Res. 31/9:2401-2407.

Johansson et al. (1994) Target-specific arrest of mRNA translation by antisense 2'-O-Alkyloligoribonucleotides, Nucleic Acids Res. 22/22:4591-4598.

Larrouy et al. (1995) Rnase H is responsible for the non-specific inhibition of in vitro translation by 2'-O-alkyl chimeric oligonucleotides: high affinity or selectivity, a dilemma to design antisense oligomers, Nucleic Acids Res. 23/17:3434-3440.

Liang, L. et al (2002) Optimizing the delivery systems of chimeric RNA-DNA oligonucleotides: Beyond general oligonucleotide transfer, Eur J. Biochem 269:5953-5758.

Majlessi et al. (1998) Advantages of 2'-O-methyl oligoribonucleotide probes for detecting RNA targets, Nuclic Acids Res.26/9:2224-2229.

Monia et al. (1993) Evaluation of 2'-Modified Oligonucleotides Containing 2'-Deoxy gaps as Antisense Inhibitors of Gens Expression, J. Biol. Chem. 268/19:14514-14522.

Nykanen et al. (2001) ATP Requirements and Small Interfering RNA Structure in the RNA Interference Pathway, Cell 107:309-321.

Stump et al. (1999) The use of modified primers to eliminate cycle sequencing artifacts, Nucleic Acids Res. 27/23:4642-4648.

Uchiyama et al. (1994) Studies of the Interactions Between *Escherichia coli* Ribonuclease HI and Its Substrate, J Mol. Biol. 243:782-791.

Braasch, D. et al (2003) "RNA Interference in Mammalian Cells by Chemically-modified RNA" Biochemistry 42/26:7967-7995.

Harborth, J. et al. (Apr. 2003) "Sequence, Chemical, and Structural Cariation of Small Interfering RNAs and Short Harpin RNAs and the Effect on Mammalian Gene Silencing" Antisense & Nucleic Acid Drug Development 13/2:83-105.

Elbashir, S. M. et al (2001) Functional Anatomy of siRNAs for Mediating efficient RNAi in *Drosophila melanogaster* embyro lysate, The EMBO Journal 20/23:6877-6888.

Jackson, A. L. et al. (2003) Expression Profiling Reveals off-target Gene Regulation by RNAI, Nature Biotechnology 21/6:635-637.

Lubini et al. Stabilizing effects of the RNA 2'-sustitutent Crystal Structure of an Oligodeoxynucleotide duplex Containing 2'-O-methylated adenosines. Chem. Biol. Sep. 1, 1994(1): 39-45.

Dharmacon RNA Technologies, Dharmacon and Merck's Rosetta Collaborate to Assess Multiple Factors Affecting Efficacy and Specificity of siRNA for Gene Silencing, Oct. 8, 2003, Press Release, Layfette, CO.

Rosetta siRNA Experiments Performed in 2007, pp. 1-11.

Rossi, J., "A Cholesterol Connection in RNAi," Nature, Nov. 2004, vol. 432, pp. 155-156.

Soutscheck, J., et al., "Therapeutic Silencing of an Endogenous Gene by Systemic Administration of Modified siRNAs," Nature, Nov. 2004, vol. 432, pp. 173-178.

Kim, D. H. et al., Synthetic dsRNA Dicer Substrates Enhance RNAi Patency and efficacy, Nature Biotechnology, Advanced Online Publication, (2004), p. 1-5, Published Online Dec. 26, 2004.

Paddison, Patrick J. et al., "Short hairpin RNAs shRNAs) induce sequence-specific silencing in mammalian cells", Genes & Development 16, (2002), p. 946-958.

Zhang, Haidi et al., "Human Dicer Preferentially cleaves dsRNAs at their termini without a requirement for ATP", The EMBO Journal vol. 21, No. 21, (2002), p. 5875-5885.

Hohjoh, Hirohiko, "Enhancement of RNAi activity by improved siRNA duplexes", FEBS letters 557, (2004), p. 193-198.

Ma, Jin-Baio et al., "Structural basis for overhanging-specific small interfering RNA recognition by PAZ domain", Nature, vol. 429, May 20, 2004, p. 318-322.

Siolas, Despina, "Synthetic shRNAs as potent RNAi triggers", Nature Biotechnology, p. 1-5, published online Dec. 26, 2004.

Zeng, Yan et al., "Both Natural and Designed Micro RNAs Technique Can Inhibit the Expression of Cognate mRNAs When Expressed in Human Cells", Molecular Cell, vol. 9, Jun. 2002, p. 1327-1333.

Holen et al. (2002) Positional Effects of short interfering RNAs targeting the human coagulation trigger Tissue Factor, Nucleic Acid Research, 30/8:1757-1766.

International Search Report from PCT/US05/011008, Mar. 31, 2005, 5 Pages.

Written Opinion from PCT/US05/011008, Mar. 31, 2005, 6 Pages.

International Search Report from PCT/US05/003365, Apr. 2, 2005, 7 Pages.

Written Opinion from PCT/US05/003365, Apr. 2, 2005, 10 Pages.

Notification Regarding Review of Justification for Invitation to Pay Additional Fees from PCT/US05.003365, Apr. 2, 2005, 4 Pages.

Office Action dated Oct. 15, 2008 cited in U.S. Appl. No. 11/283,482.

Office Action dated Nov. 3, 2008 cited in U.S. Appl. No. 11/283,483.

Office Action dated Dec. 9, 2008 cited in U.S. Appl. No. 11/283,481.

Office Action dated Aug. 23, 2005 cited in U.S. Appl. No. 11/019,831.

Office Action dated Feb. 21, 2006 cited in U.S. Appl. No. 11/019,831.

Office Action dated Jun. 28, 2006 cited in U.S. Appl. No. 11/019,831.

Office Action dated Feb. 9, 2007 cited in U.S. Appl. No. 11/019,831.

Office Action dated Oct. 30, 2007 cited in U.S. Appl. No. 11/019,831.

Office Action dated Sep. 4, 2008 cited in U.S. Appl. No. 11/019,831.

Office Action dated Sep. 12, 2008 cited in U.S. Appl. No. 11/390,829.

Office Action dated Feb. 22, 2008 cited in U.S. Appl. No. 11/051,195.

Office Action dated Dec. 18, 2008 cited in U.S. Appl. No. 11/051,195.

Office Action dated Sep. 8, 2008 cited in U.S. Appl. No. 10/551,350.

Office Action dated Dec. 31, 2008 cited in U.S. Appl. No. 11/619,993.

Office Action dated Jan. 14, 2005 cited in U.S. Appl. No. 10/406,908.

Office Action dated Apr. 5, 2005 cited in U.S. Appl. No. 10/406,908.

Office Action dated Sep. 23, 2005 cited in U.S. Appl. No. 10/406,908.

Office Action dated Jan. 27, 2005 cited in U.S. Appl. No. 10/613,077.

Office Action dated Apr. 12, 2005 cited in U.S. Appl. No. 10/613,077.

Office Action dated Sep. 7, 2005 cited in U.S. Appl. No. 10/613,077.

SuperArray SureSilencing Array Plates User Manual (Version 1.0 Feb. 13, 2004)—SureSilencing Array Plates; Validated Gene-Specific siRNA for Pathway Profiling by Reverse Transfection; Frederick, MD, USA.

SuperArray SureSilencing Array Plates User Manual (Version 1.1 Mar. 5, 2004)—SureSilencing Array Plates; Validated Gene-Specific siRNA for Pathway Profiling by Reverse Transfection; Frederick, MD, USA.

U.S. Appl. No. 11/283,483, Mail Date Dec. 11, 2007, Restriction Requirement.

U.S. Appl. No. 11/283,483, Mail Date Mar. 28, 2008, Office Action Appendix/Miscellaneous Action with SSP.

U.S. Appl. No. 11/283,483, Mail Date Nov. 3, 2008, Non-Final Rejection/References.

U.S. Appl. No. 11/283,482, Mail Date Dec. 11, 2007, Restriction Requirement.

U.S. Appl. No. 11/283,482, Mail Date Oct. 15, 2008, Non-Final Rejection.

U.S. Appl. No. 11/283,481, Mail Date Dec. 12, 2007, Restriction Requirement.

U.S. Appl. No. 11/283,481, Mail Date Mar. 28, 2008, Office Action Appendix; Miscellaneous Action with SSP.

U.S. Appl. No. 11/283,481, Mail Date Dec. 10, 2008, Non-Final Rejection.

U.S. Appl. No. 11/283,483, Mail Date Dec. 28, 2009, Office Action.

U.S. Appl. No. 11/283,481, Mail Date Oct. 15, 2009, Office Action.

Minakuchi, Yoshiko, et al., Atelocollagen-Mediated Synthetic Small Interfering RNA Delivery for Effective Gene Silencing in Vitro and in Vitro, Nucleic Acids Research, 2004, vol. 32, No. 13, Oxford University Press 2004, pp. 1-7, Published online Jul. 22, 2004.

Yoshikawa, Tomohiro, et al., Transfection Microarray of Human Mesenchymal Stem Cells and On-Chip siRNA Gene Knockdown, Journal of Controlled Release 96 (2004), pp. 227-232.

U.S. Appl. No. 11/283,481, Mail Date May 11, 2010, Office Action.
U.S. Appl. No. 11/283,482, Mail Date Apr. 8, 2010, Office Action.
Office Action from U.S. Appl. No. 11/283,481, dated Oct. 15, 2009.
Office Action from U.S. Appl. No. 11/283,481, dated May 11, 2010.
Notice of Allowance from U.S. Appl. No. 11/283,481, dated Aug. 30, 2010.
Office Action from U.S. Appl. No. 11/283,483, dated Dec. 11, 2007.
Office Action from U.S. Appl. No. 11/283,483, dated Nov. 3, 2008.
Office Action from U.S. Appl. No. 11/283,483, dated Dec. 28, 2009.
Office Action from U.S. Appl. No. 11/283,482, dated Apr. 8, 2010.
Notice of Allowance from U.S. Appl. No. 11/283,482, dated Aug. 23, 2010.
Extended European Search Report from EPO Application No. 05852038.8, dated Apr. 24, 2008.
Supplemental European Search Report from EPO Application No. 05852038.8, dated May 13, 2008.
Annex to EPO Form 2001A from EPO Application No. 05852038.8, dated Aug. 1, 2008.
Examination Report from EPO Application No. 05852038.8, dated Feb. 19, 2009.
Examination Report from EPO Application No. 05852038.8, dated Jun. 23, 2009.
Examination Report from EPO Application No. 05852038.8, dated Nov. 11, 2009.
Summons to Attend Oral Hearing from EPO Application No. 0585203.8, dated May 7, 2010.
Communication EPO Application No. 05852038.8, dated Sep. 6, 2010.
Communication Pursuant to Article 94(3) EPC from EPO Application No. 05852038.8, dated Sep. 10, 2010.
Invitation to Respond to Written Opinion from Singapore Patent Application No. 200703649-4, dated Sep. 17, 2008.
Examination Report from Singapore Patent Application No. 200703649-4, dated May 19, 2009.
Examination Report from New Zealand Patent Application No. 555248, dated Oct. 8, 2008.
Examination Report from New Zealand Patent Application No. 555248, dated Nov. 25, 2009.
Examination Report from New Zealand Patent Application No. 555248, dated Dec. 7, 2009.
Examination Report from New Zealand Patent Application No. 555248, dated Jun. 2, 2010.
Examination Report from New Zealand Patent Application No. 555248, dated Jun. 10, 2010.
Office Action from Chinese Patent Application No. 200580047054.2, dated Jul. 7, 2010 with unverified English Translation.
Bellows, The Use of siRNA Screening for the Development of Novel Therapies and Mapping of Genetic Pathways, MMG 445 Basic Biotechnology eJournal 2007 3:67-72.
Denning et al., High Throughput RNAi by Reverse Transfection With Low siRNA Concentrations, Qiagen GmbH, date unreadable.
Denning et al., High Throughput RNAi by Reverse Transfection With Low siRNA Concentrations, Qiagen GmbH, from ePosters The Online Journal of Scientific Posters, Received at the EPO on Mar. 31, 2010.
SABiosciences (Annex 2), http://sabioscience.com/RNAiInfo.iph?pcatn=SIH715685ABCD, printed Aug. 27, 2010.
Ming-Hon Hou et al., Effects of Polyamines on the Thermal Stability and Formation Kinetics of DNA Duplexes with Abnormal Structure, Nucleic Acids Research, 2001, vol. 29, No. 24 5121-5128.
Chan Yong Lee et al, Inhibitory Effect of Spermine of the Susceptibility of FNA for RNase A, Journal of the Korean Chemical Society, vol. 29, No. 6, 1985.
Super Array Bioscience's siRNA Array Plates and SureSilencing siRNA and Antibody Kits, and Ambion's Silencer Phosphodiesterase siRNA Library, Mar. 19, 2004 from http://www.genomeweb.com/rnai/superarray-biosciences-s-sirna-arr.
siRNA For Gene Silencing from www.qiagen.com/goto/products/customsiRNA, date unknown.
SABioscienes, SureSilencing siRNA Arrays, dated Jan. 1, 2009, from http://www.sabiosciences.com/RNAiArrayPlate.phr.
SABiosciences, User Manual SureSilencing siRNA Arrays, Pathway-Focused Validated Gene Knockdown by RNA Interference, Part #1029A, Version 1.1, Jan. 25, 2008.
Erfle, et al., "Reverse Transfection on Cell Arrays for High Content Screening Microscopy," Nature Protocols, vol. 2, No. 2, 2007.

* cited by examiner

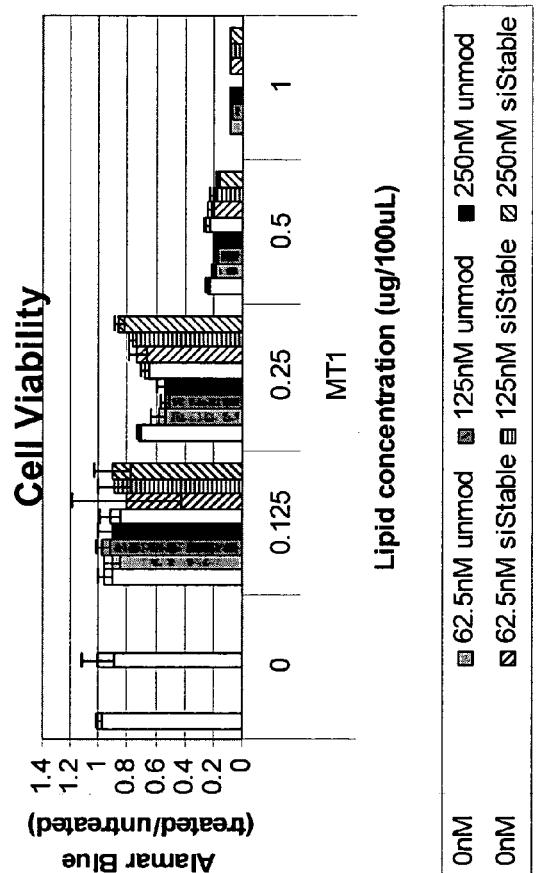
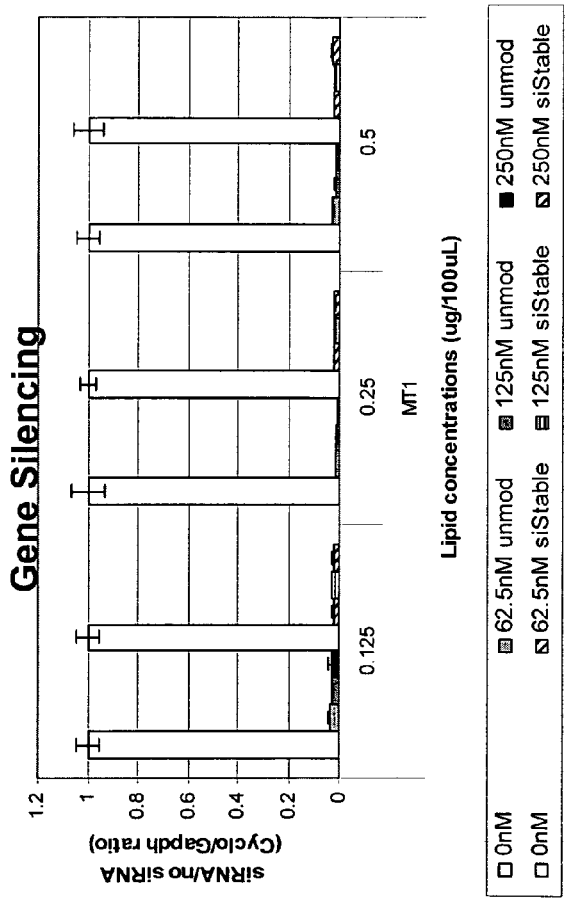
FIG. 11A
FIG. 11B

SEQUENCE LISTING

```
<160> NUMBER OF SEQ ID NOS: 34

<210> SEQ ID NO 1
<211> LENGTH: 7
<212> TYPE: RNA
<213> ORGANISM: Homo sapiens
<220> FEATURE:
<221> NAME/KEY: misc_feature
<222> LOCATION: (1)..(7)
<223> OTHER INFORMATION: shRNA loop

<400> SEQUENCE: 1 auaugug                                                                     7

<210> SEQ ID NO 2
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: siRNA targeting a SRD5a1 gene
```

```
<400> SEQUENCE: 2
ccggaaattt gaagagtat                                              19

<210> SEQ ID NO 3
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: GAPDH siRNA 1

<400> SEQUENCE: 3
caacggauuu ggucguauu                                              19

<210> SEQ ID NO 4
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: GAPDH siRNA 3

<400> SEQUENCE: 4
gaauuuggcu acagcaaca                                              19

<210> SEQ ID NO 5
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: GAPDH siRNA 4

<400> SEQUENCE: 5
gaaaucccau caccaucuu                                              19

<210> SEQ ID NO 6
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K1 siRNA 1

<400> SEQUENCE: 6
gcacauggau ggagguucu                                              19

<210> SEQ ID NO 7
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K1 siRNA 2

<400> SEQUENCE: 7
gcagagagag cagauuuga                                              19

<210> SEQ ID NO 8
<211> LENGTH: 19
<212> TYPE: RNA
<213> ORGANISM: Homo sapiens
```

```
<220> FEATURE:
<221> NAME/KEY: misc_feature
<222> LOCATION: (1)..(19)
<223> OTHER INFORMATION: MAP2K1 siRNA 4

<400> SEQUENCE: 8
gagcagauuu gaagcaacu                                                    19

<210> SEQ ID NO 9
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K1 siRNA 5

<400> SEQUENCE: 9
ccagaaagcu aauucaucu                                                    19

<210> SEQ ID NO 10
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K2 siRNA 1

<400> SEQUENCE: 10
caaagacgau gacuucgaa                                                    19

<210> SEQ ID NO 11
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K2 siRNA 2

<400> SEQUENCE: 11
gaucagcauu ugcauggaa                                                    19

<210> SEQ ID NO 12
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K2 siRNA 4

<400> SEQUENCE: 12
ggaagcugau ccaccuuga                                                    19

<210> SEQ ID NO 13
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: MAP2K2 siRNA 7

<400> SEQUENCE: 13
gaaagucagc aucgcgguu                                                    19
```

```
<210> SEQ ID NO 14
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: Cyclo3 siRNA

<400> SEQUENCE: 14
acagcaaauu ccaucgugu                                              19

<210> SEQ ID NO 15
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: Cyclo14 siRNA

<400> SEQUENCE: 15
ggccuuagcu acaggagag                                              19

<210> SEQ ID NO 16
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: Cyclo28 siRNA

<400> SEQUENCE: 16
ggcuacaaaa acagcaaau                                              19

<210> SEQ ID NO 17
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: Cyclo37 siRNA

<400> SEQUENCE: 17
uuccaucgug uaaucaagg                                              19

<210> SEQ ID NO 18
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: gapdh 4 siRNA

<400> SEQUENCE: 18
ugguuuacau guuccaaua                                              19

<210> SEQ ID NO 19
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: gapdh 3 siRNA

<400> SEQUENCE: 19
```

```
gaccucaacu acaugguuu                                                  19

<210> SEQ ID NO 20
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: gapdh 2
<220> FEATURE:
<221> NAME/KEY: misc_feature
<222> LOCATION: (1)..(19)
<223> OTHER INFORMATION: gapdh 2 siRNA

<400> SEQUENCE: 20
gaaaucccau caccaucuu                                                  19

<210> SEQ ID NO 21
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: gapdh 1 siRNA

<400> SEQUENCE: 21
caacggauuu ggucguauu                                                  19

<210> SEQ ID NO 22
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: UQCRC1 siRNA

<400> SEQUENCE: 22
gcacacagcu uacuacauc                                                  19

<210> SEQ ID NO 23
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: UQCRC2 siRNA

<400> SEQUENCE: 23
gaaaugcccu gguaucuca                                                  19

<210> SEQ ID NO 24
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: UQCRC3 siRNA

<400> SEQUENCE: 24
gaaggaacgu gaugugauc                                                  19

<210> SEQ ID NO 25
<211> LENGTH: 19
```

```
<212> TYPE: RNA
<213> ORGANISM: Homo sapiens
<220> FEATURE:
<221> NAME/KEY: misc_feature
<222> LOCATION: (1)..(19)
<223> OTHER INFORMATION: UQCRC4 siRNA

<400> SEQUENCE: 25
gagauguggu cuuuaacua                                                       19

<210> SEQ ID NO 26
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: HSPLKSTK1 siRNA

<400> SEQUENCE: 26
caaccaaagu cgaauauga                                                       19

<210> SEQ ID NO 27
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: HSPLKSTK2 siRNA

<400> SEQUENCE: 27
gguaucagcu cugugauaa                                                       19

<210> SEQ ID NO 28
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: HSPLKSTK3 siRNA

<400> SEQUENCE: 28
gcaccgaaac cgaguuauu                                                       19

<210> SEQ ID NO 29
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: HSPLKSTK4 siRNA

<400> SEQUENCE: 29
gcacauaccg ccugagucu                                                       19

<210> SEQ ID NO 30
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: G6PD4 siRNA

<400> SEQUENCE: 30
acagauacaa gaacgugaa                                                       19
```

```
<210> SEQ ID NO 31
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: G6PD3 siRNA

<400> SEQUENCE: 31
acaucgccug cguuauccu                                                    19

<210> SEQ ID NO 32
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: G6PD2 siRNA

<400> SEQUENCE: 32
ucacgagucc ugcaugagc                                                    19

<210> SEQ ID NO 33
<211> LENGTH: 19
<212> TYPE: RNA
<213> ORGANISM: Homo sapiens

<400> SEQUENCE: 33
auucacgagu ccugcauga                                                    19

<210> SEQ ID NO 34
<211> LENGTH: 19
<212> TYPE: RNA
<213> ORGANISM: Homo sapiens
<220> FEATURE:
<221> NAME/KEY: misc_feature
<222> LOCATION: (1)..(19)
<223> OTHER INFORMATION: IGF1R-73 siRNA

<400> SEQUENCE: 34
ugcugaccuc uguuaccuc                                                    19
```

US 7,935,811 B2

APPARATUS AND SYSTEM HAVING DRY GENE SILENCING COMPOSITIONS

CROSS-REFERENCE TO RELATED APPLICATIONS

This United States Patent Application claims benefit of U.S. Provisional Application Ser. No. 60/630,320, filed Nov. 22, 2004, and U.S. Provisional Application Ser. No. 60/678,165, filed May 04, 2005, both of which are incorporated herein by reference.

This United States Patent Application also cross-references the following United States Patent Applications filed herewith: Ser. No. 11/283,482, entitled APPARATUS AND SYSTEM HAVING DRY GENE SILENCING POOLS, with Barbara Robertson, Ph.D., et al. as inventors; Ser. No. 11/283,483, entitled APPARATUS AND SYSTEM HAVING DRY CONTROL GENE SILENCING COMPOSITIONS, with Barbara Robertson, Ph.D., et al as inventors; and Ser. No. 11/283,481, entitled METHOD OF DETERMINING A CELLULAR RESPONSE TO A BIOLOGICAL AGENT, with Barbara Robertson, Ph.D., et al. as inventors, wherein each is incorporated herein by reference.

BACKGROUND OF THE INVENTION

1. The Field of the Invention

The present invention relates to an apparatus and system for use in RNA interference. More particularly, the present invention relates to an apparatus and system that includes well plates having dry gene silencing compositions comprised of siRNA.

2. The Related Technology

Recently, a natural cellular regulatory pathway was discovered that uses transcribed microRNA ("miRNA") in order to control protein production. The miRNA includes a duplex region of sense and antisense RNA. This regulatory pathway uses miRNA in order to target complementary mRNA to inhibit production of the encoded protein. Accordingly, a complex series of proteins are involved in this RNA interfering pathway to inhibit or stop production of the proteins encoded by the mRNA. As such, the process is referred to as RNA interference or RNAi.

Additionally, it has been found that the RNAi pathway can be used with synthetic dsRNA (e.g., siRNA) for silencing genes and inhibiting protein expression. This can allow for siRNA having specific sequences to be produced to target complementary DNA and/or mRNA encoding a specific protein. The siRNA can interact with the natural RNAi pathway to silence a target gene and inhibit production of the encoded polypeptide. The ability to silence a specific gene and inhibit production of the encoded protein has been used for basic research of gene function, gene mapping, cellular pathway analysis, and other gene-related studies.

In order to induce gene silencing, the siRNA needs to be introduced into a cell. While the most common procedures for introducing nucleic acids into cells has been forward transfection, reverse transfection ("RTF") has been developed more recently and used as an alternative to forward transfection procedures. In certain versions of RTF protocols, a complex of lipid-nucleic acid (e.g., lipoplex) can be prepared and introduced into the test wells of a well plate. Cells are introduced into the test wells with the lipid-nucleic acid complexes, and incubated so that the siRNA can enter the cells. Examples of some RTF protocols can be found in U.S. Pat. No. 5,811,274 to Palsson, U.S. Pat. No. 5,804,431 to Palsson and U.S. Pat. No. 6,544,790 to Sabatini and in U.S. Published Applications 2002/0006664 to Sabatini and 2003/070642 to Caldwell et al. As described in these references, RTF procedures for nucleic acids generally can have fewer steps compared to traditional forward transfection and may offer benefits in attempting to isolate the transfected cells to particular regions of a single surface, such as a glass slide. However, RTF procedures for siRNA have not been optimized to the point of practical application, and improvements in gene silencing efficacy are still needed, especially for situations in which one is experimenting with multiple different siRNAs, different gene targets or different cell lines.

Therefore, it would be advantageous to have an improved RTF protocol for delivering siRNA into cells to effect gene silencing through the RNAi pathway. Additionally, it would be beneficial to have the RTF format, including the siRNA, configured in a manner that enhances the efficacy of gene silencing.

BRIEF SUMMARY OF THE INVENTION

Generally, embodiments of the present invention include well plates, kits, systems, and methods of using the same for effecting gene silencing in a cell. Accordingly, the present invention provides well plates, kits, and systems that implement an improved RTF protocol for delivering siRNA into cells to effect gene silencing through the RNAi pathway. Additionally, the well plates, kits, and systems can include siRNA configured to be implemented in an RTF protocol in a manner that enhances stability during reverse transfection. Furthermore, the present invention includes methods of using such well plates, kits, and systems.

In one embodiment, the present invention includes a reverse transfection apparatus configured for introducing siRNA into a cell to effect gene silencing. Such an apparatus includes a well plate having a well configured for transfecting cells. The well can include a substantially dry gene silencing composition that has at least a first siRNA which silences at least a first target gene. The gene silencing composition is configured such that the siRNA is capable of being solubilized or suspended in an aqueous medium in an amount sufficient for transfecting cells in the well. Optionally, the total amount of siRNA in the gene silencing composition is sufficient for implementing reverse transfection for only one well. Additionally, it is optional for the siRNA to have at least one of a hairpin structure having a loop, a modification or a conjugate. Also, the siRNA can be rationally designed to specifically silence the target gene in an efficient manner that does not induce significant silencing of non-target genes. Furthermore, the gene silencing composition can include a pool of siRNAs that target different polynucleotides of the same target gene.

In one embodiment, the present invention provides a kit or system that includes a well plate consistent with any of the foregoing characterizations. Additionally, such a kit or system can include a polynucleotide carrier. The polynucleotide carrier can be a cationic lipid, polymer, polypeptide, lipopolymer, lipid-polypeptide combination, or the like. Additionally, the kit or system can include various solubilizing solutions, reagents, cell culture media, and the like, which are discussed in more detail herein.

In one embodiment, the present invention includes a method of reverse transfection for introducing siRNA into a cell to effect gene silencing. Such a method can include providing a well plate in accordance with the foregoing characterizations. An aqueous medium can be added to the well so as to suspend or solubilize the gene silencing composition and/or siRNA into the solution. Additionally, cells can be added to the well under conditions that permit the siRNA to enter the cell. For example, the cells can be added to different wells in a 96-well plate in an amount of about $1 \times 10^3$ to about $3.5 \times 10^4$ cells per about 0.3 cm$^2$ to about 0.35 cm$^2$ of cell growth surface area, or more preferably at $2 \times 10^3$ to about $3 \times 10^4$.

In one embodiment, the method can include adding a polynucleotide carrier to the well so as to form an siRNA-carrier complex. The siRNA-carrier complex can be suspended or solubilized in the aqueous medium, and can contact the cell to induce entry into the cell, which can be by any endocytosis process. As such, the polynucleotide carrier can be added to the well as part of the aqueous medium or in addition thereto. The polynucleotide carrier can be a cationic lipid, polymer, lipopolymer, polypeptide, antibody-polypeptide conjugate, and the like. Alternatively, other polynucleotide delivery processes can be used to deliver the siRNA into the cells including electroporation, precipitation, physical bombardment, optoporation, and the like.

After the cells are combined with the siRNA composition in the well, the well plate can be maintained under conditions so that cell growth, cell division, and/or gene silencing occurs. Such conditions are usually normal cell culturing conditions well known in the art. As such, the siRNA can silence the target gene and inhibit production of a target polypeptide by at least 50%, more preferably by at least 70%, and most preferably by at least 90%.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention can be rendered by reference to specific embodiments thereof which are illustrated in the appended drawings. It is appreciated that these drawings depict only typical embodiments of the invention and are therefore not to be considered limiting of its scope. The invention can be described and explained with additional specificity and detail through the use of the accompanying drawings in which:

FIG. 2A is an embodiment of luciferase expression in a forward transfection protocol where HeLa cells at 10,000 cells per well were plated in PLL plates and transfected with LIPOFECTAMINE™ 2000-pCMV-Luc complexes to demonstrate the functionality of the pCMV-Luc expression vector. FIG. 2B is an embodiment of a cell viability study using conditions described in FIG. 2A, wherein the Y-axis represents relative levels of survival with 1.0 being 100% viability. FIG. 2C is an embodiment of a reverse transfection protocol with pCMV-Luc plasmid with a range of lipids (LIPOFECTAMINE™ 2000, OLIGO-FECTAMINE™, Transit TKO, and siRNA168 (168)) and plasmid concentrations, where HeLa cells at 10,000 cells per well, and luciferase expression levels were assessed 24 hours later using the STEADYGLOW™ kit. FIG. 2D is an embodiment of cell viability at conditions described in FIG. 2C, where "1.0" represents 100% cell viability. FIG. 2E is an embodiment of reverse transfection of cyclo 3 siRNA using LIPOFECTAMINE™ 2000, OLIGOFECTAMINE™, TKO, or siRNA168 lipids for gene silencing, where the Y-axis represents the level of gene expression compared to controls with 1.0 being 100% expression. FIG. 2F is an embodiment of cell viability results from conditions described in FIG. 2E.

FIG. 11A is a graphical representation of an embodiment of cell viability with DharmaFECT™ 1 and stabilized and unstabilized siRNA.

FIG. 11B is a graphical representation of an embodiment of the gene silencing of the conditions of FIG. 11A.

concentration and control siRNA concentration on gene silencing in 5,000 HeLa cells per well on day 2 of an experiment.

Figure 13A:
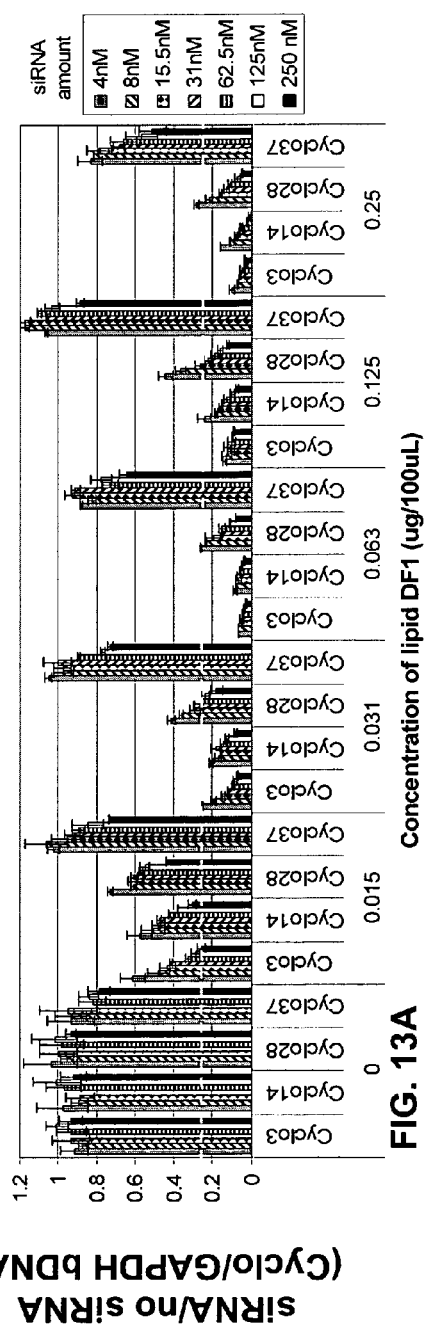
FIG. 13A is a graphical representation of an embodiment of siRNA RTF of variations in DharmaFECT™ 1 ("DF1")
Figure 13B:
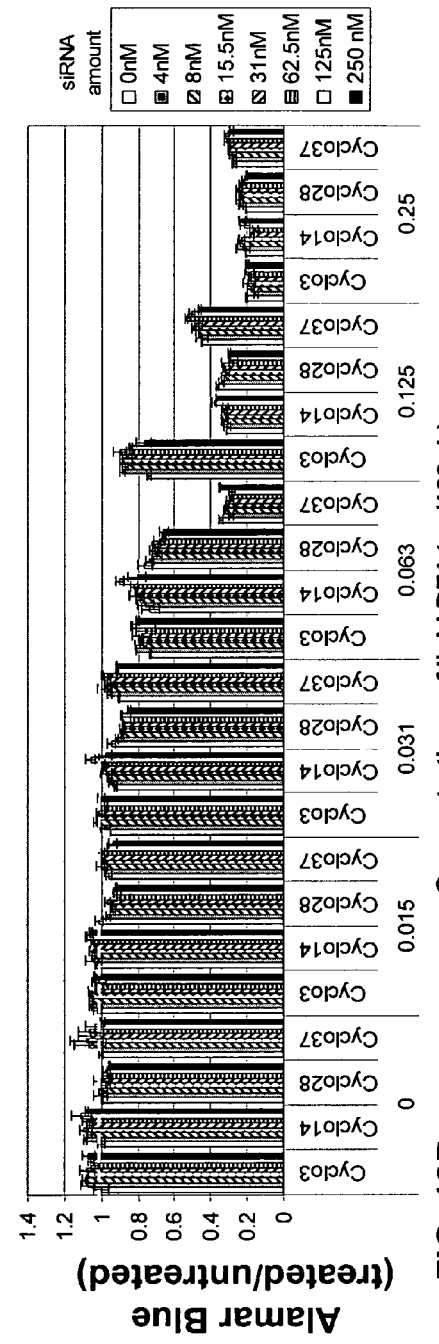

FIG. 13B is a graphical representation of the cell viability of the conditions of FIG. 13A.

Figure 14A:
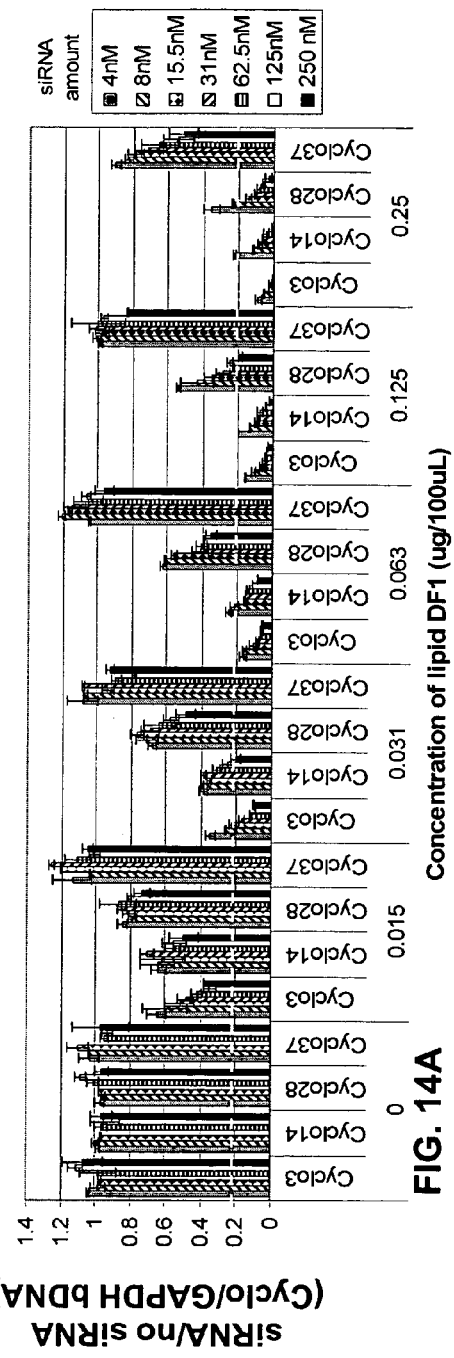

FIG. 14A is a graphical representation of an embodiment of siRNA RTF of variations in DharmaFECT™ 1 ("DF1") concentration and control siRNA concentration on gene silencing in 5,000 HeLa cells per well on day 4 of an experiment.

Figure 14B:
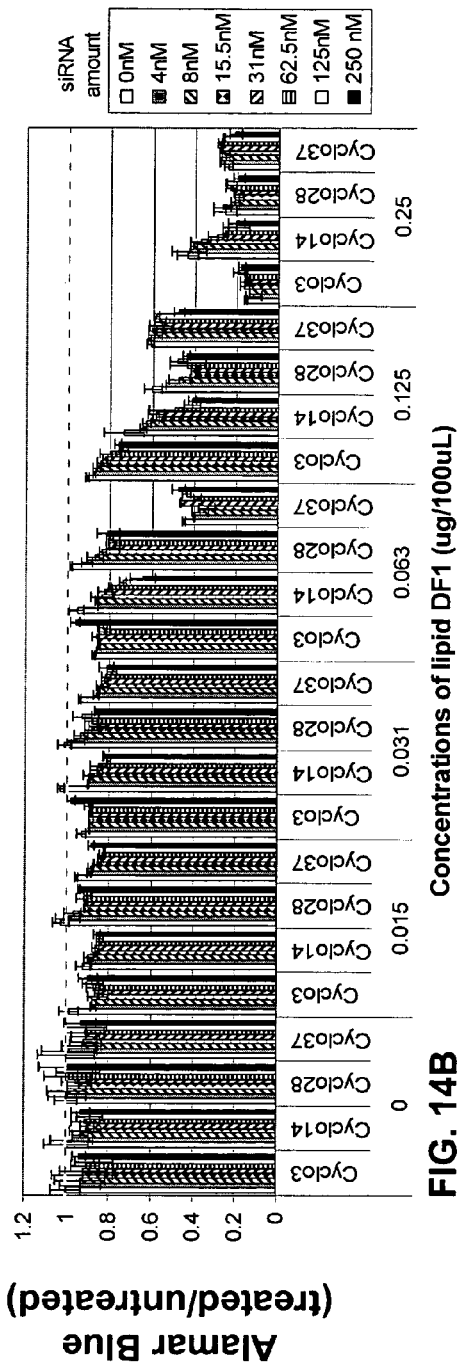

FIG. 14B is a graphical representation of the cell viability of the conditions of FIG. 14A.

Figure 15A:
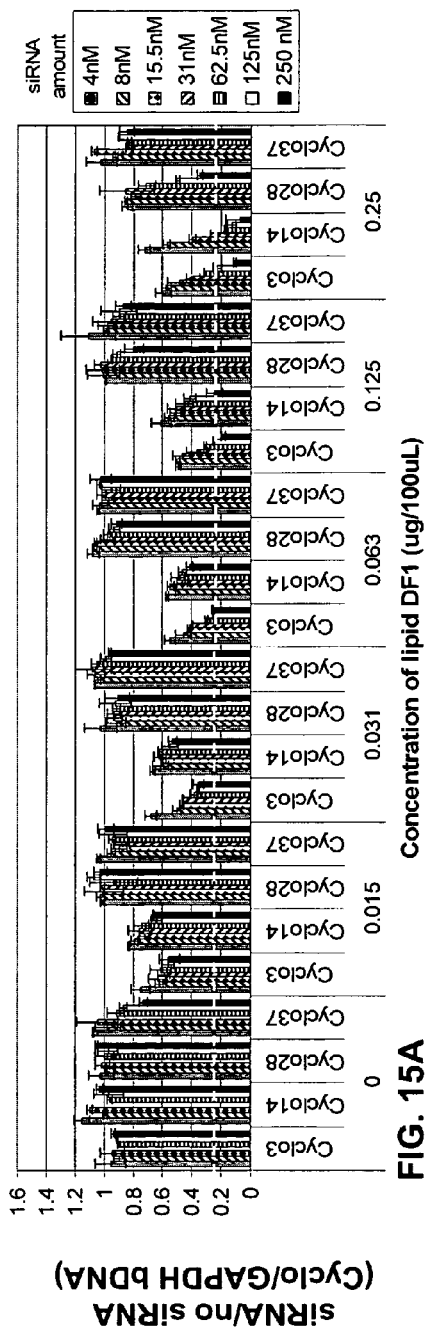

FIG. 15A is a graphical representation of an embodiment of siRNA RTF of variations in DharmaFECT™ 1 ("DF1") concentration and control siRNA concentration on gene silencing in 5,000 HeLa cells per well on day 8 of an experiment.

Figure 15B:
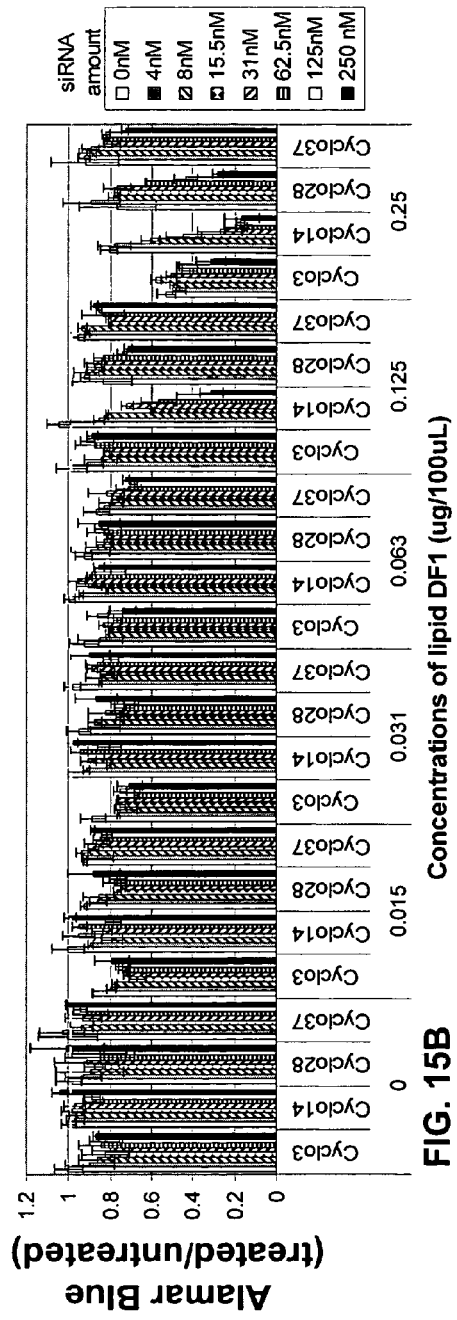

FIG. 15B is a graphical representation of the cell viability of the conditions of FIG. 15A.

Figure 16A:
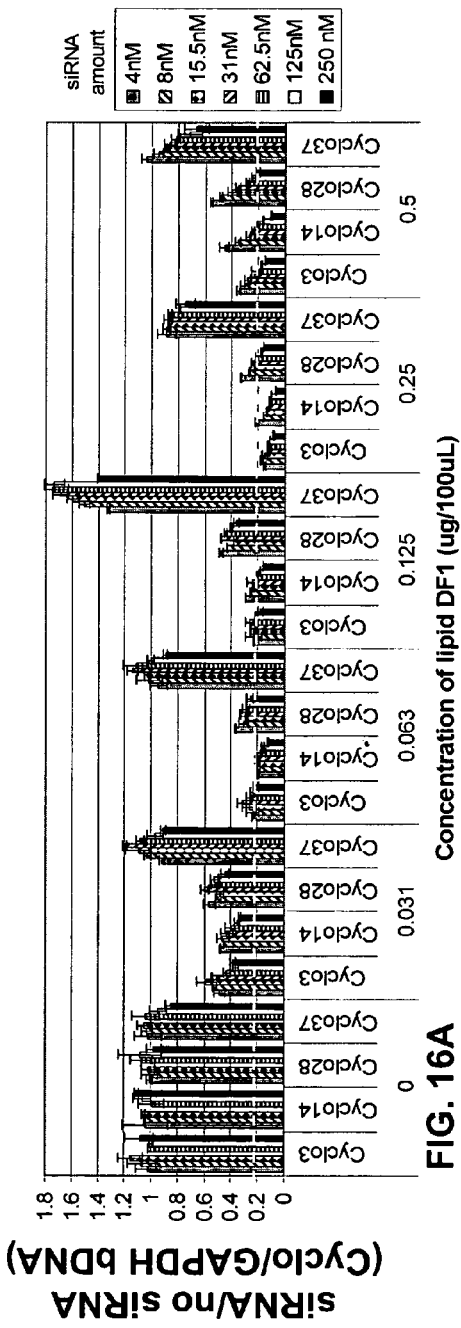

FIG. 16A is a graphical representation of an embodiment of siRNA RTF of variations in DharmaFECT™ 1 ("DF1") concentration and control siRNA concentration on gene silencing in 10,000 HeLa cells per well on day 1 of an experiment.

Figure 16B:
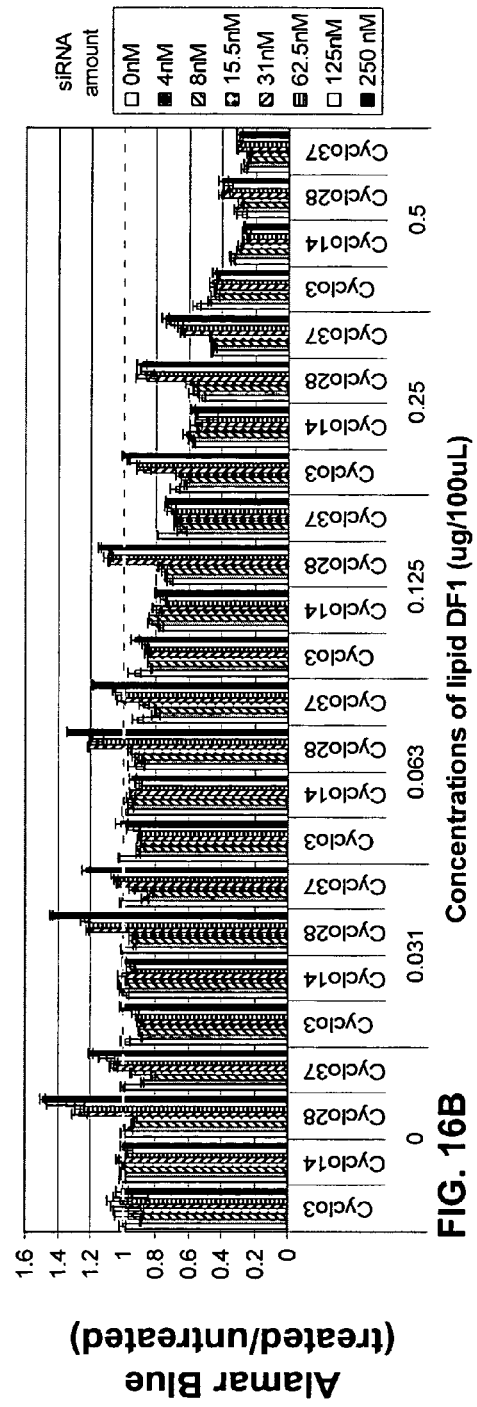

FIG. 16B is a graphical representation of the cell viability of the conditions of FIG. 16A.

Figure 17A:
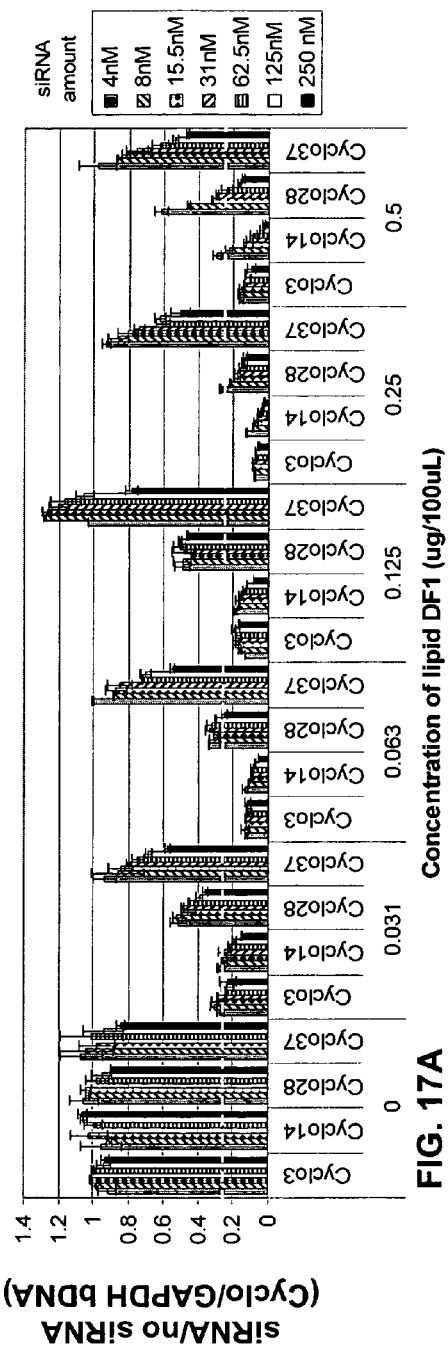

FIG. 17A is a graphical representation of an embodiment of siRNA RTF of variations in DharmaFECT™ 1 ("DF1") concentration and control siRNA concentration on gene silencing in 10,000 HeLa cells per well on day 2 of an experiment.

Figure 17B:
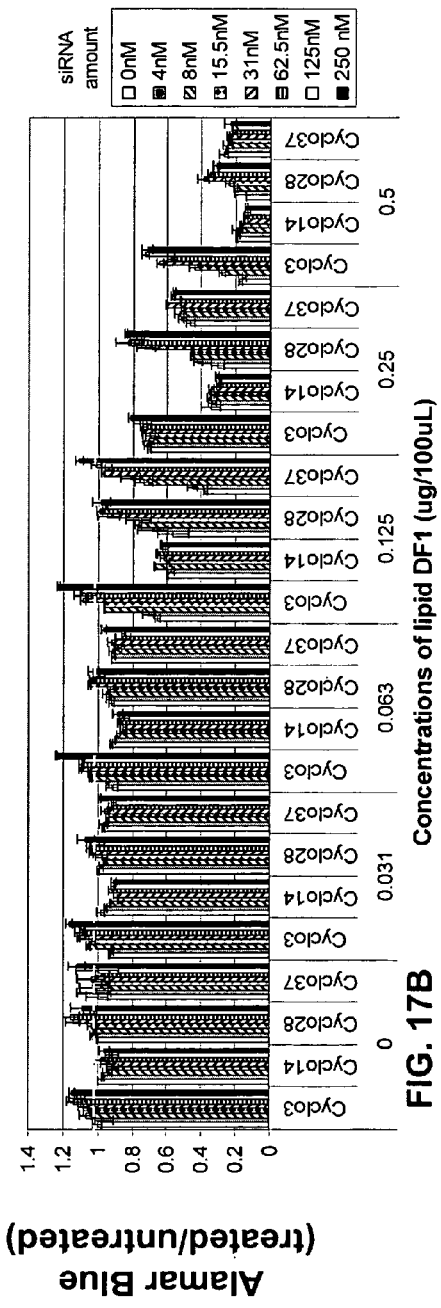

FIG. 17B is a graphical representation of the cell viability of the conditions of FIG. 17A.

Figure 18A:
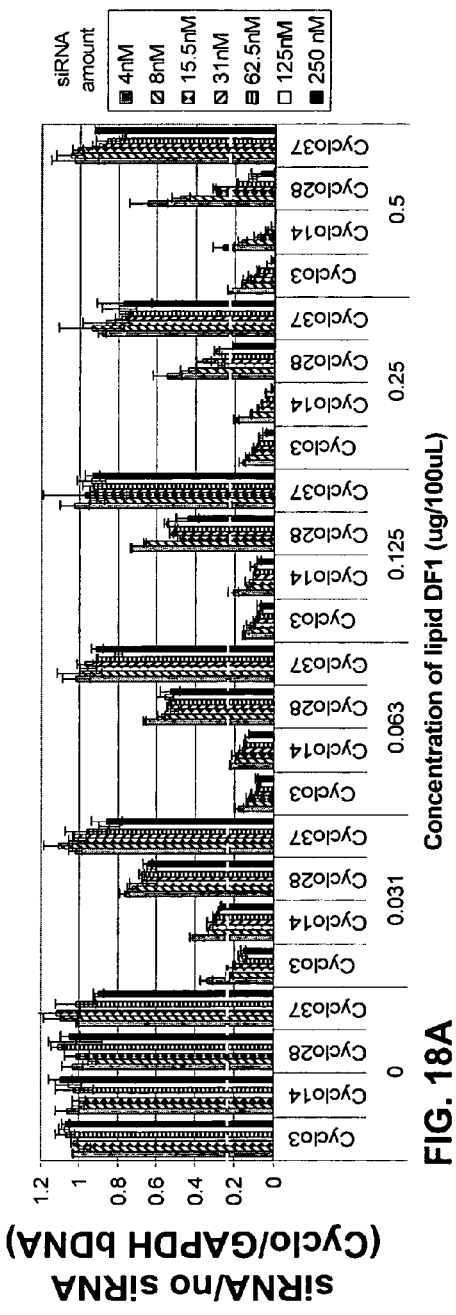

FIG. 18A is a graphical representation of an embodiment of siRNA RTF of variations in DharmaFECT™ 1 ("DF1") concentration and control siRNA concentration on gene silencing in 10,000 HeLa cells per well on day 4 of an experiment.

Figure 18B:
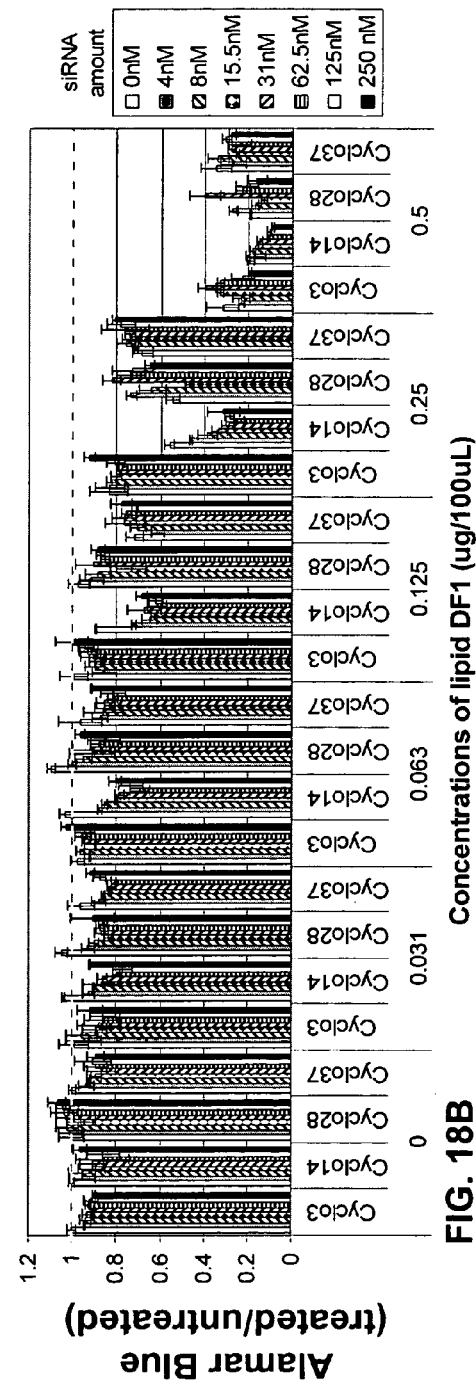

FIG. 18B is a graphical representation of the cell viability of the conditions of FIG. 18A.

Figure 19A:
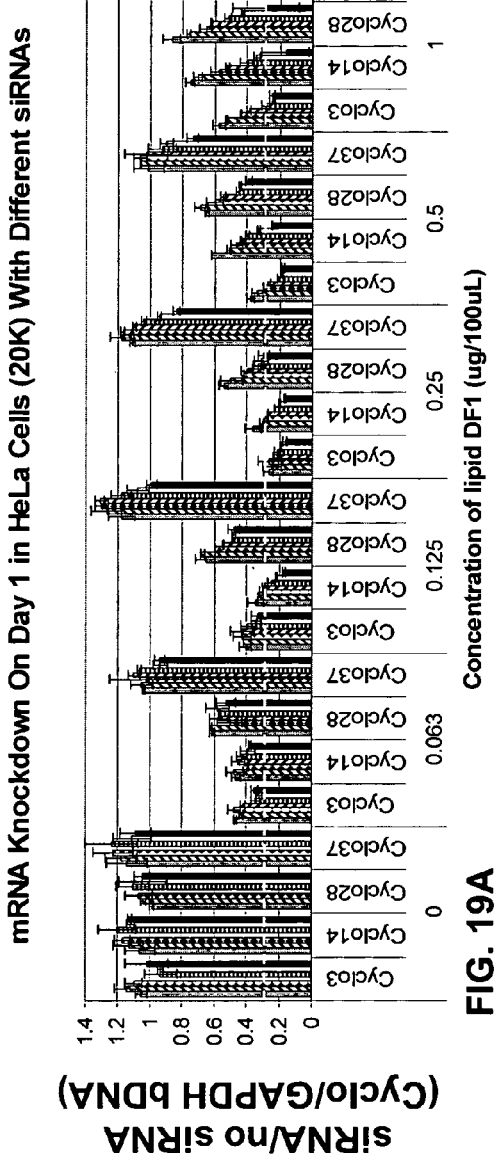

FIG. 19A is a graphical representation of an embodiment of siRNA RTF of variations in DharmaFECT™ 1 ("DF1") concentration and control siRNA concentration on gene silencing in 20,000 HeLa cells per well on day 1 of an experiment.

Figure 19B:
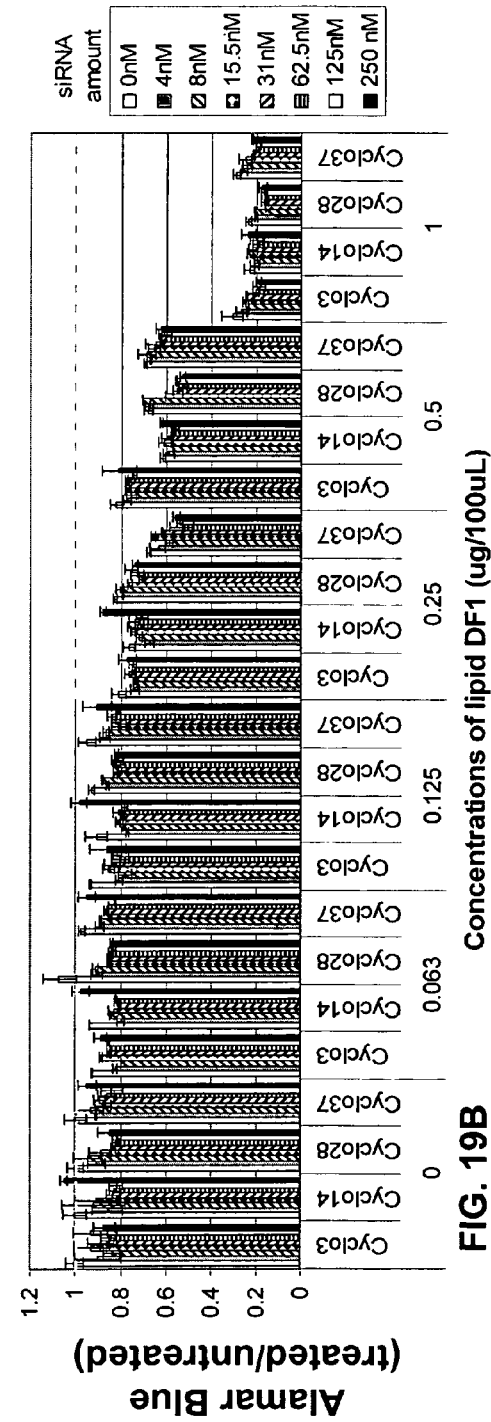

FIG. 19B is a graphical representation of the cell viability of the conditions of FIG. 19A.

Figure 20A:
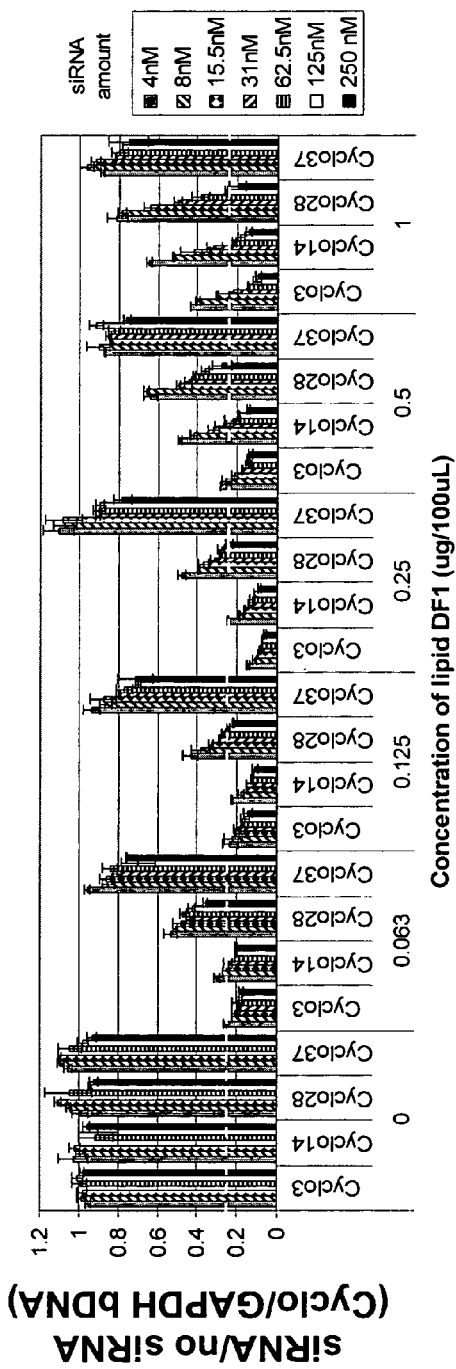

FIG. 20A is a graphical representation of an embodiment of siRNA RTF of variations in DharmaFECT™ 1 ("DF1") concentration and control siRNA concentration on gene silencing in 20,000 HeLa cells per well on day 2 of an experiment.

Figure 20B:
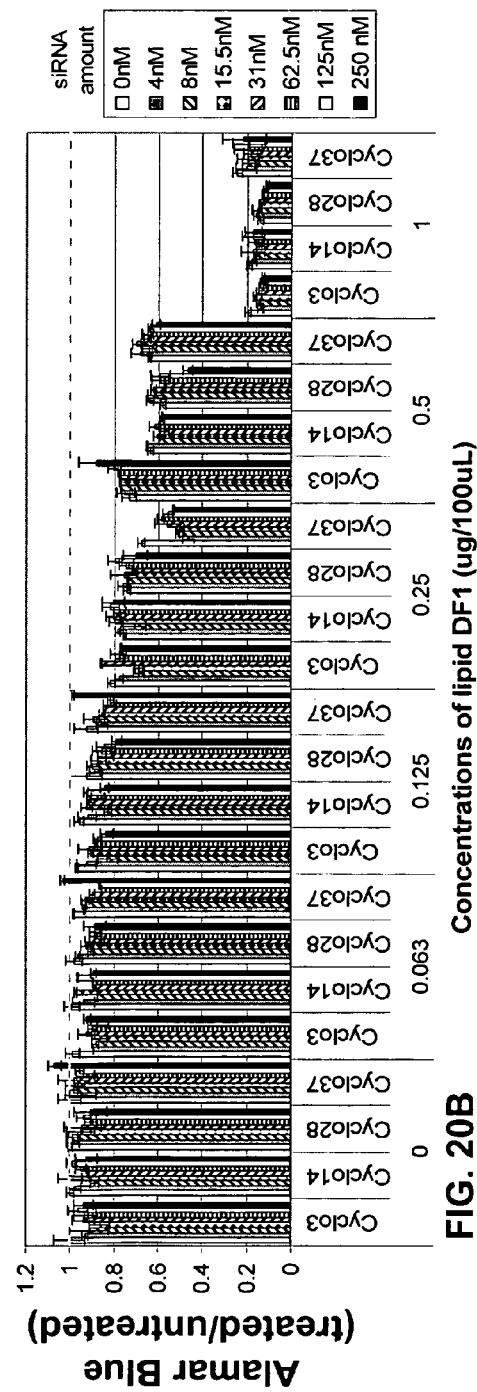

FIG. 20B is a graphical representation of the cell viability of the conditions of FIG. 20A.

Figure 21A:
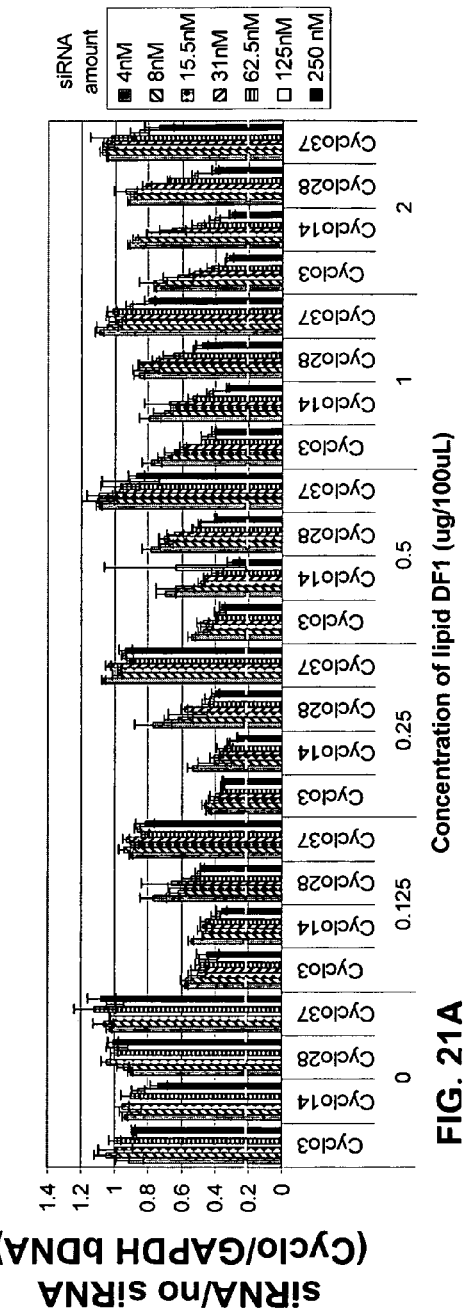

FIG. 21A is a graphical representation of an embodiment of siRNA RTF of variations in DharmaFECT™ 1 ("DF1") concentration and control siRNA concentration on gene silencing in 40,000 HeLa cells per well on day 1 of an experiment.

Figure 21B:
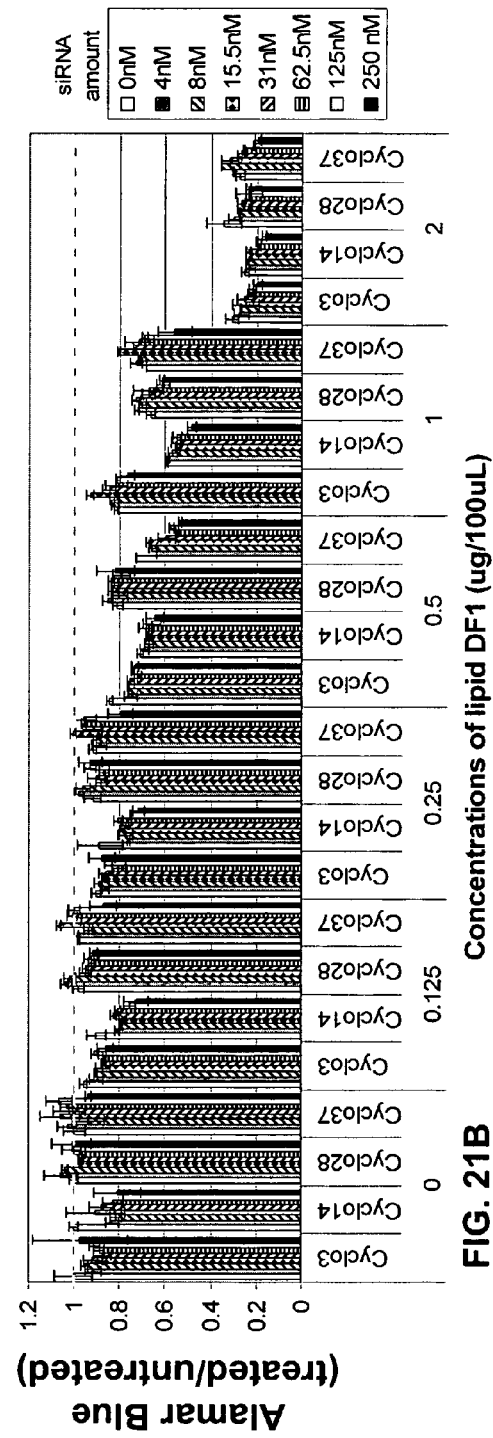

FIG. 21B is a graphical representation of the cell viability of the conditions of FIG. 21A.

Figure 22:
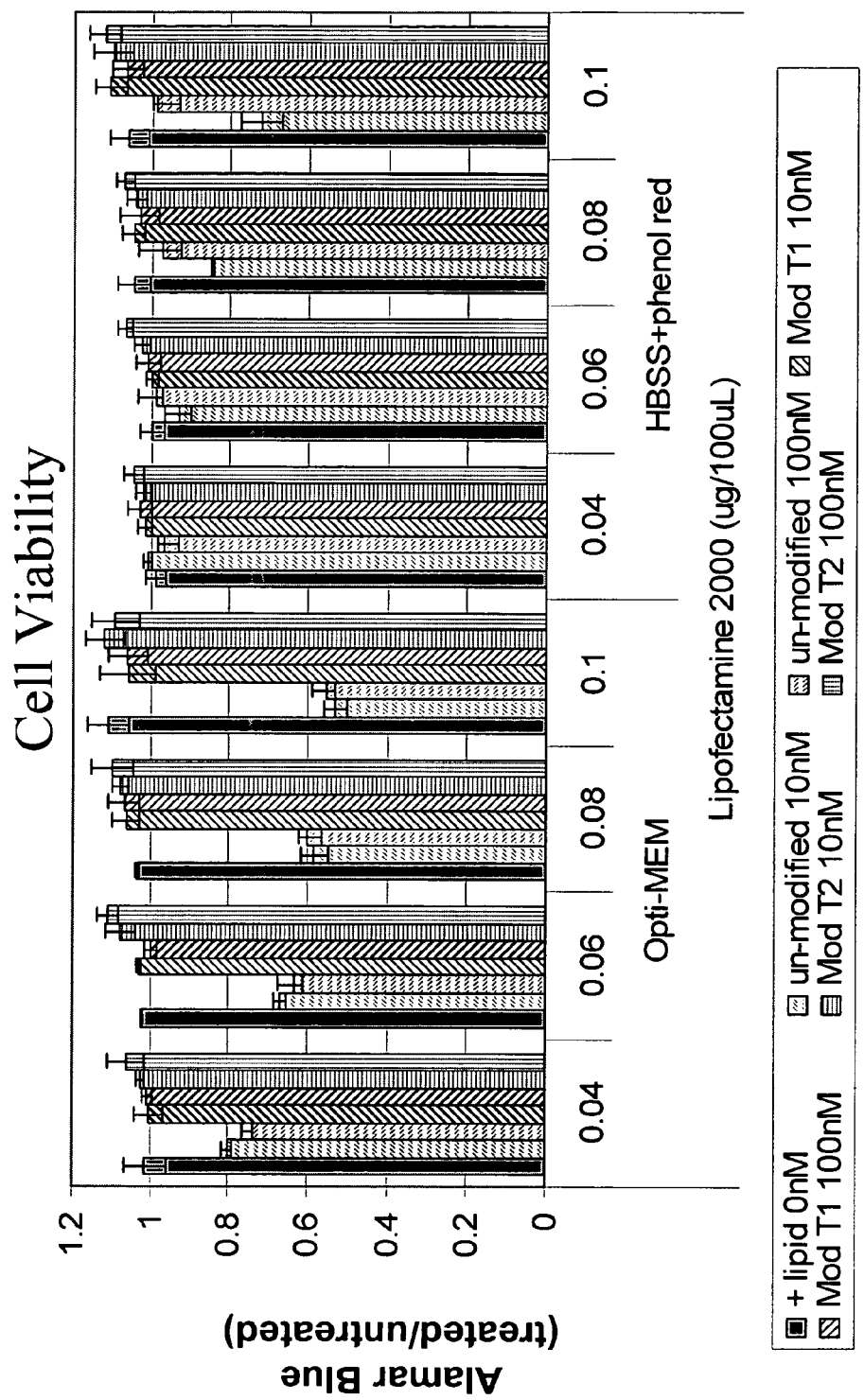

FIG. 22 is a graphical representation of an embodiment of siRNA RTF of cell media compared to buffer with varying LIPOFECTAMINE™ 2000 concentration and control siRNA concentration (e.g. modified siRNA and unmodified siRNA) on cell viability.

Figure 23A:
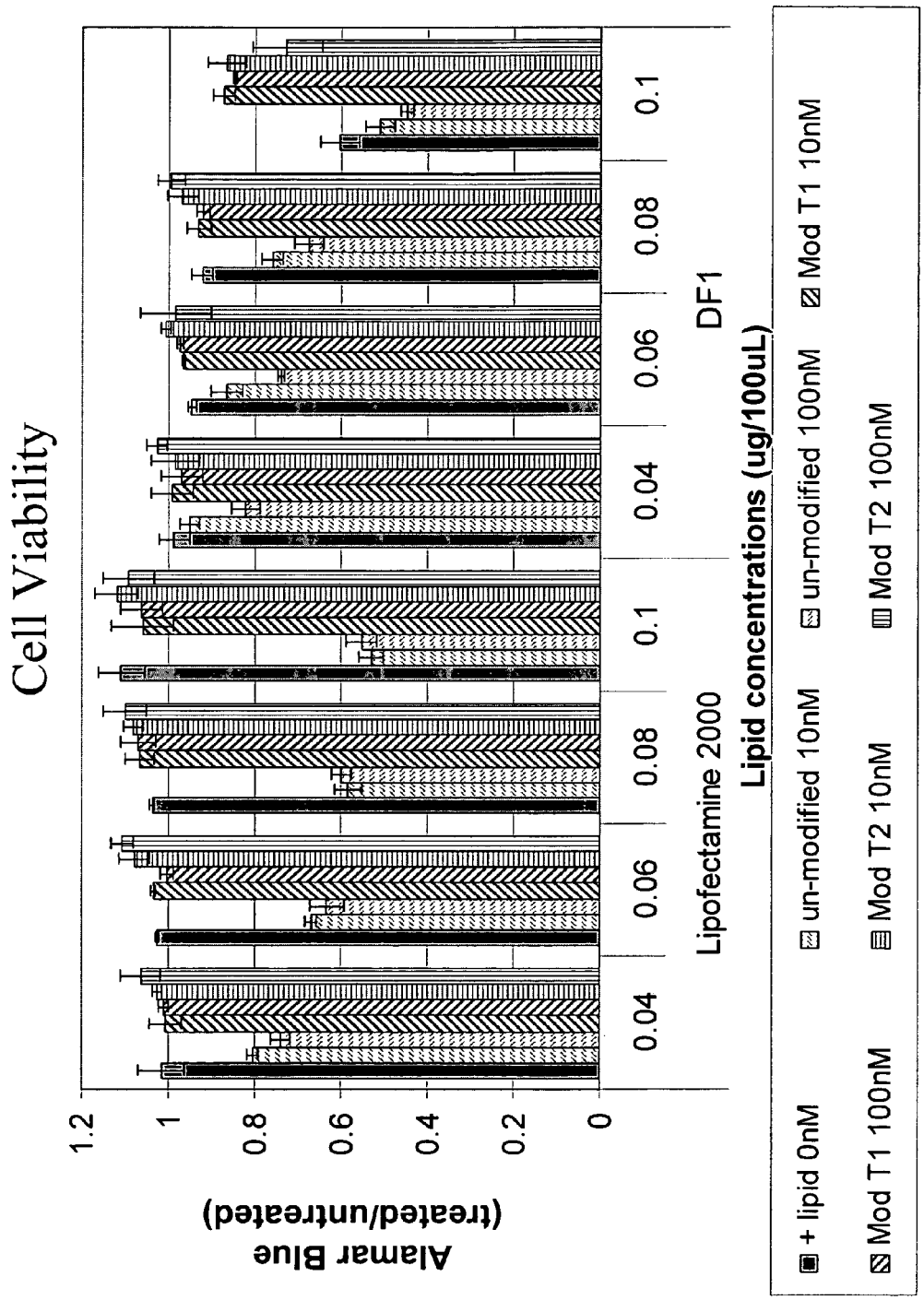

FIG. 23A is a graphical representation of an embodiment of siRNA RTF varying LIPOFECTAMINE™ 2000 and DharmaFECT™ 1 ("DF1") concentration and varying control siRNA concentration (e.g. modified siRNA and unmodified siRNA targeting the SRD5a1 gene) on cell viability.

Figure 23B:
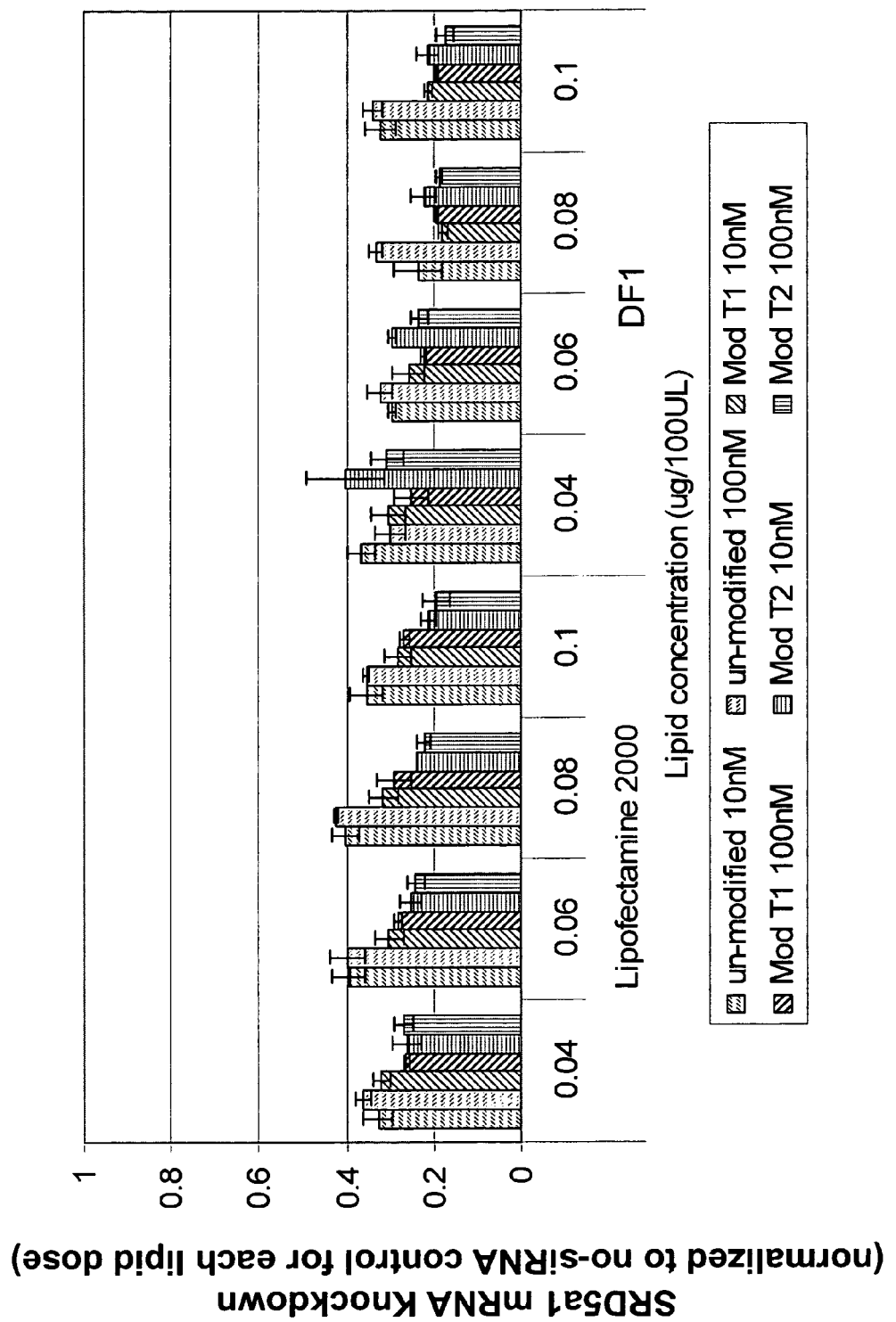

FIG. 23B is a graphical representation of an embodiment of gene silencing of the conditions of FIG. 23A.

Figure 24A:
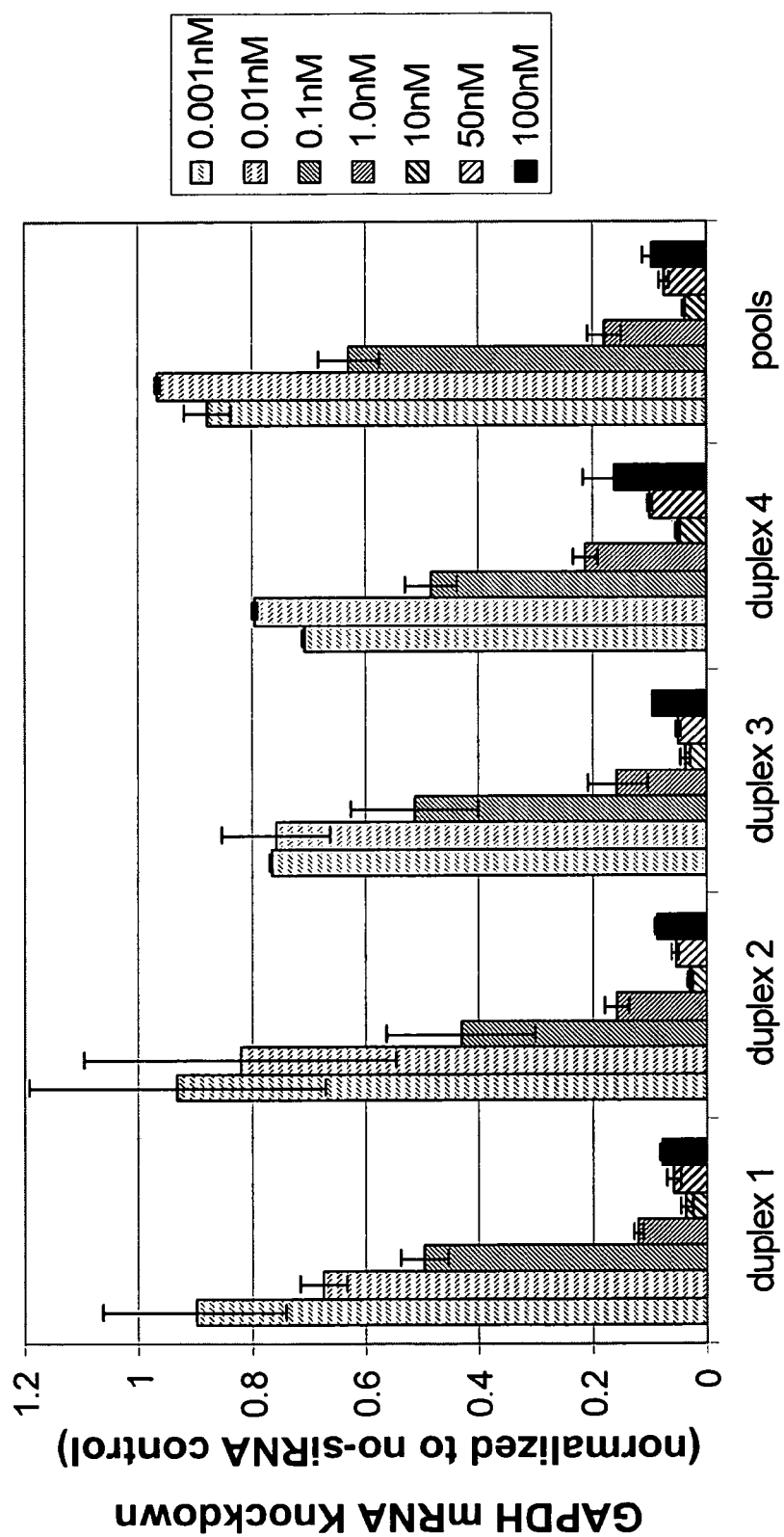
Figure 24B:
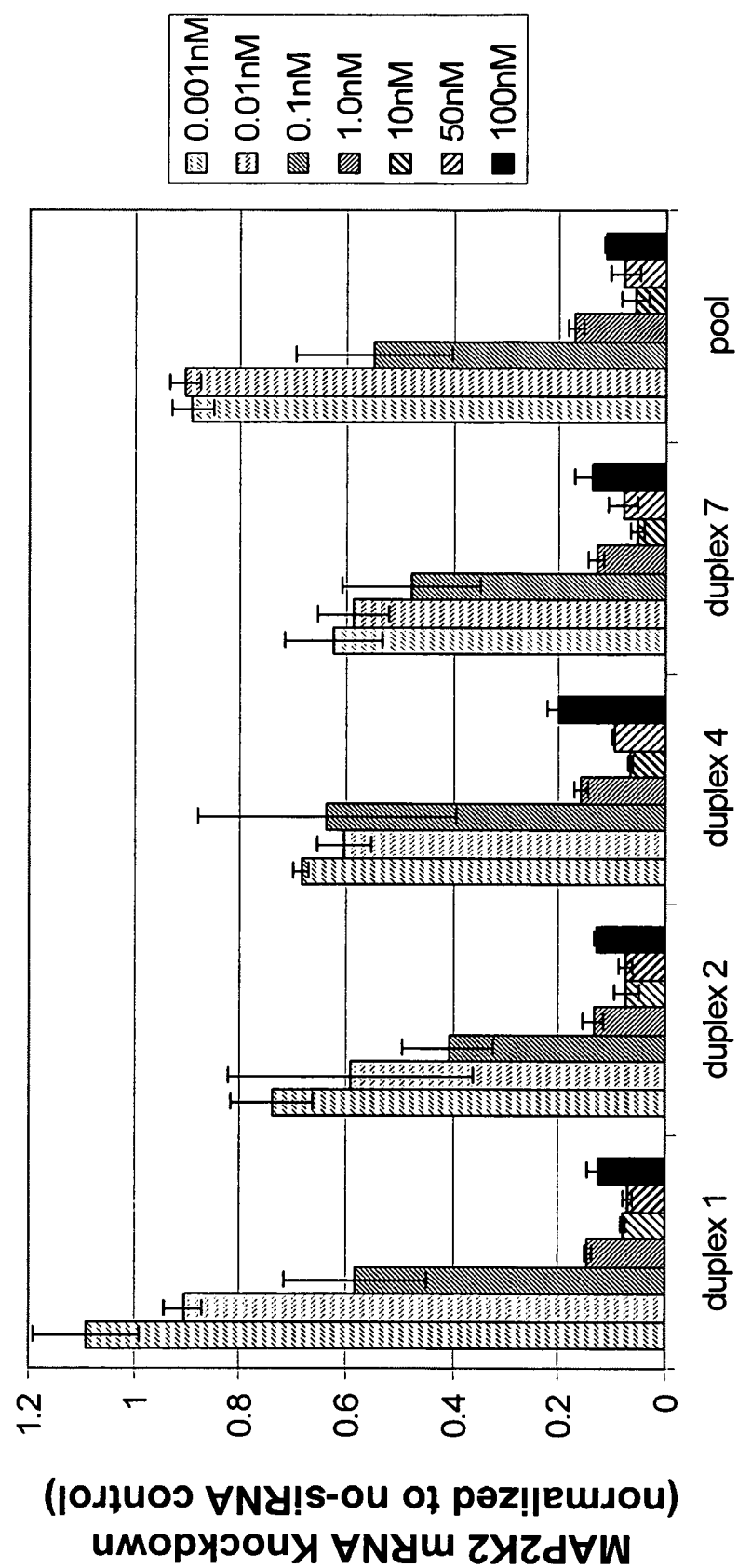
Figure 24C:
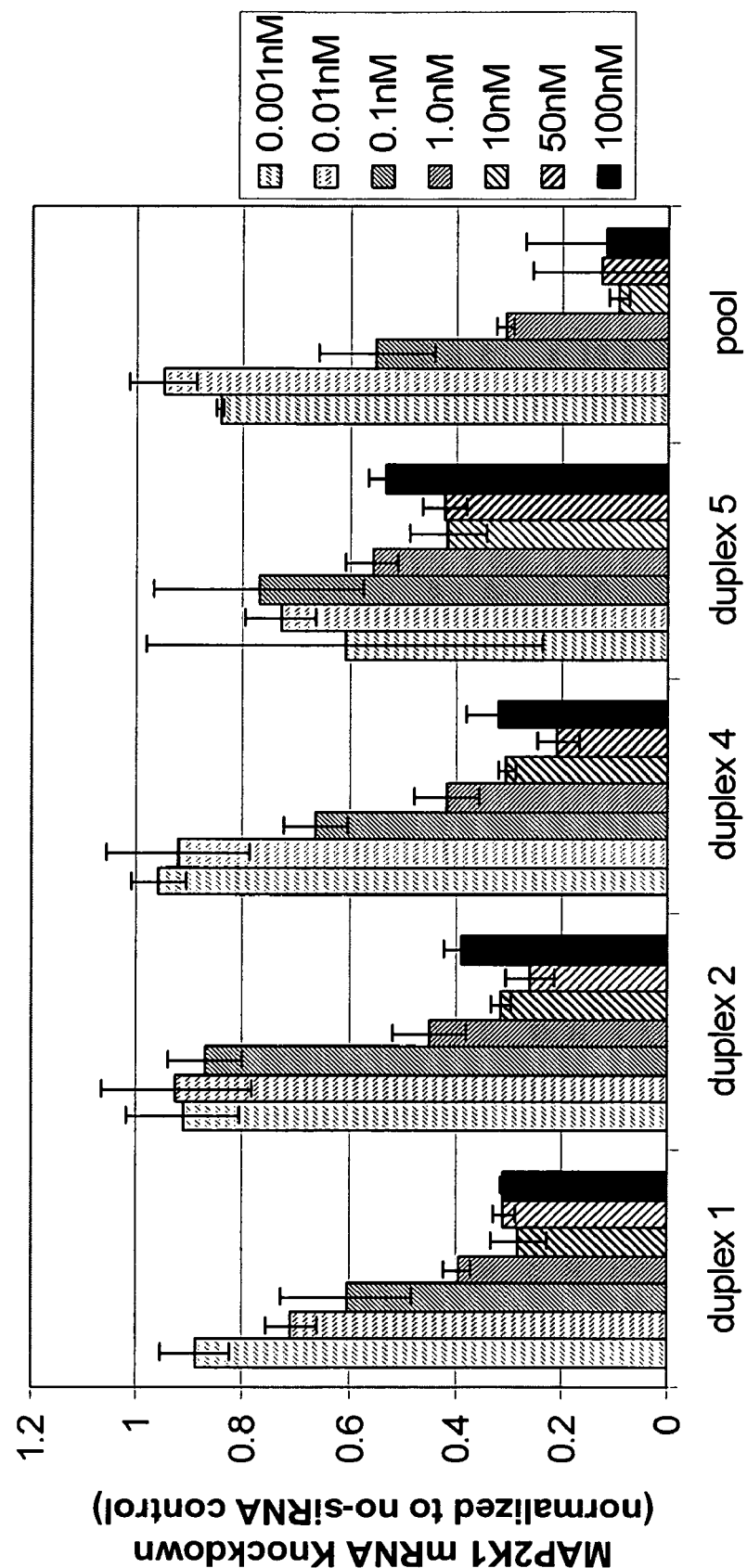

FIGS. 24A-24C are graphical representations of an embodiment of siRNA RTF protocols that compare the effectiveness of individual siRNA and pools of siRNA directed against, GAPDH, MAP2K2, and MAP2K1 at varying concentrations.

Figure 25A:
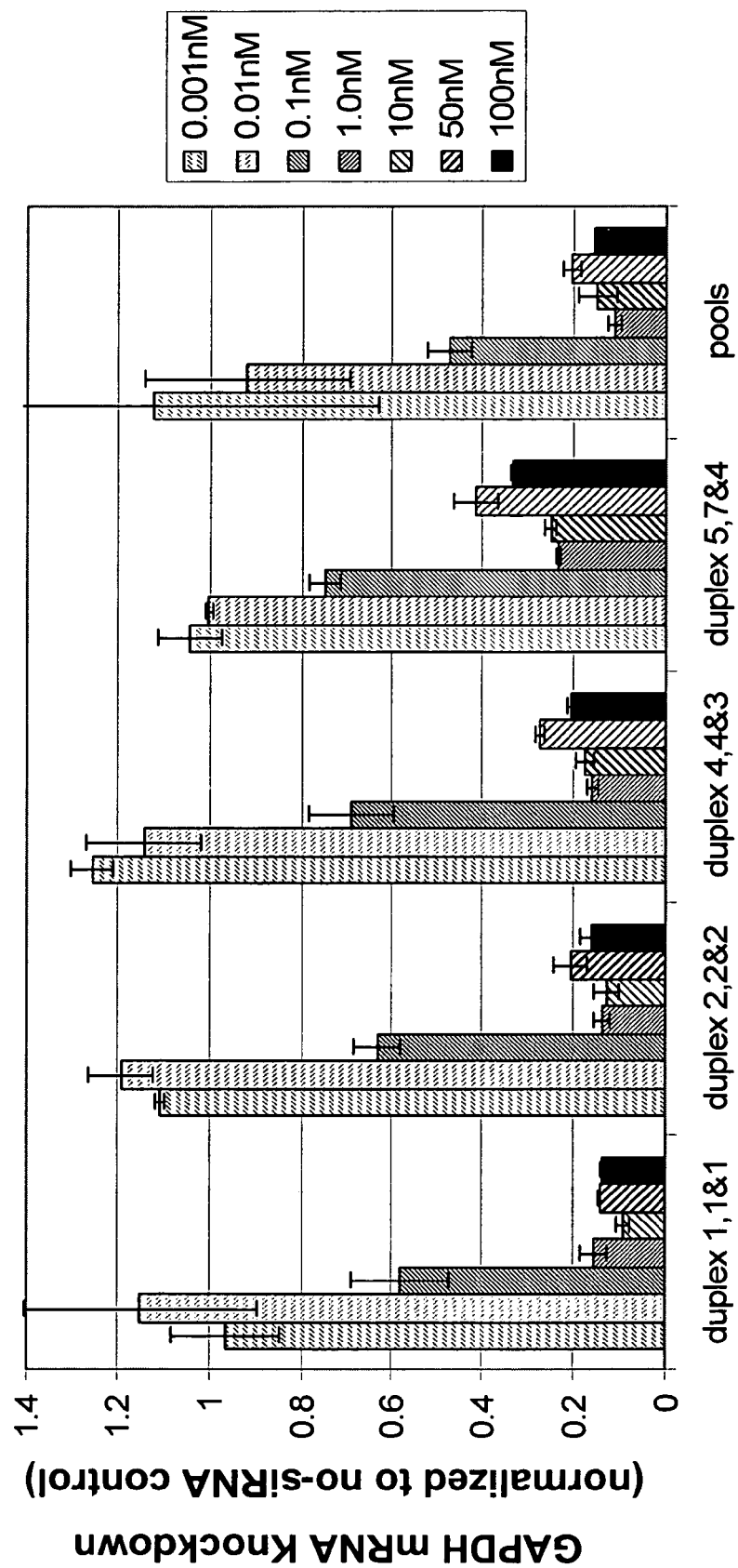
Figure 25B:
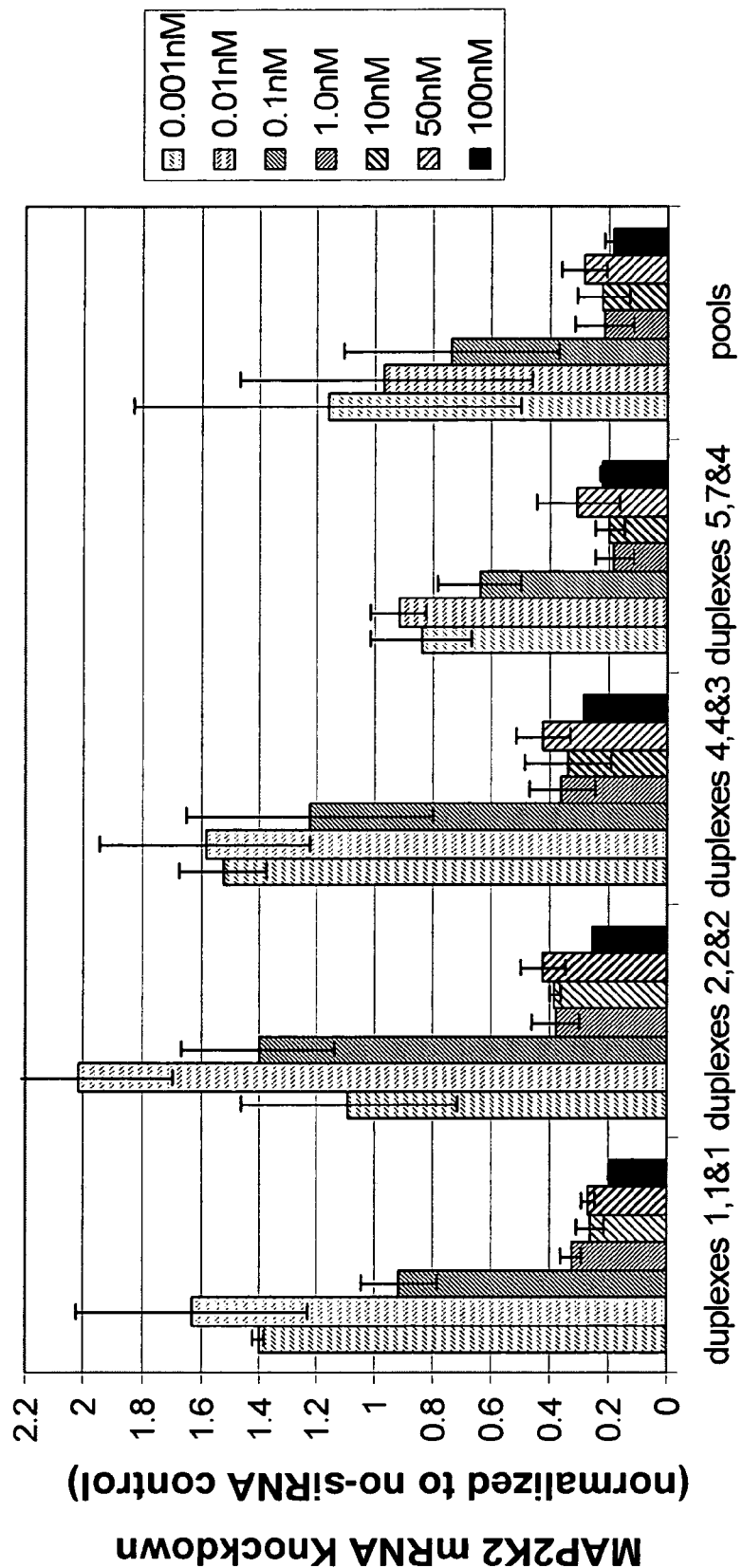
Figure 25C:
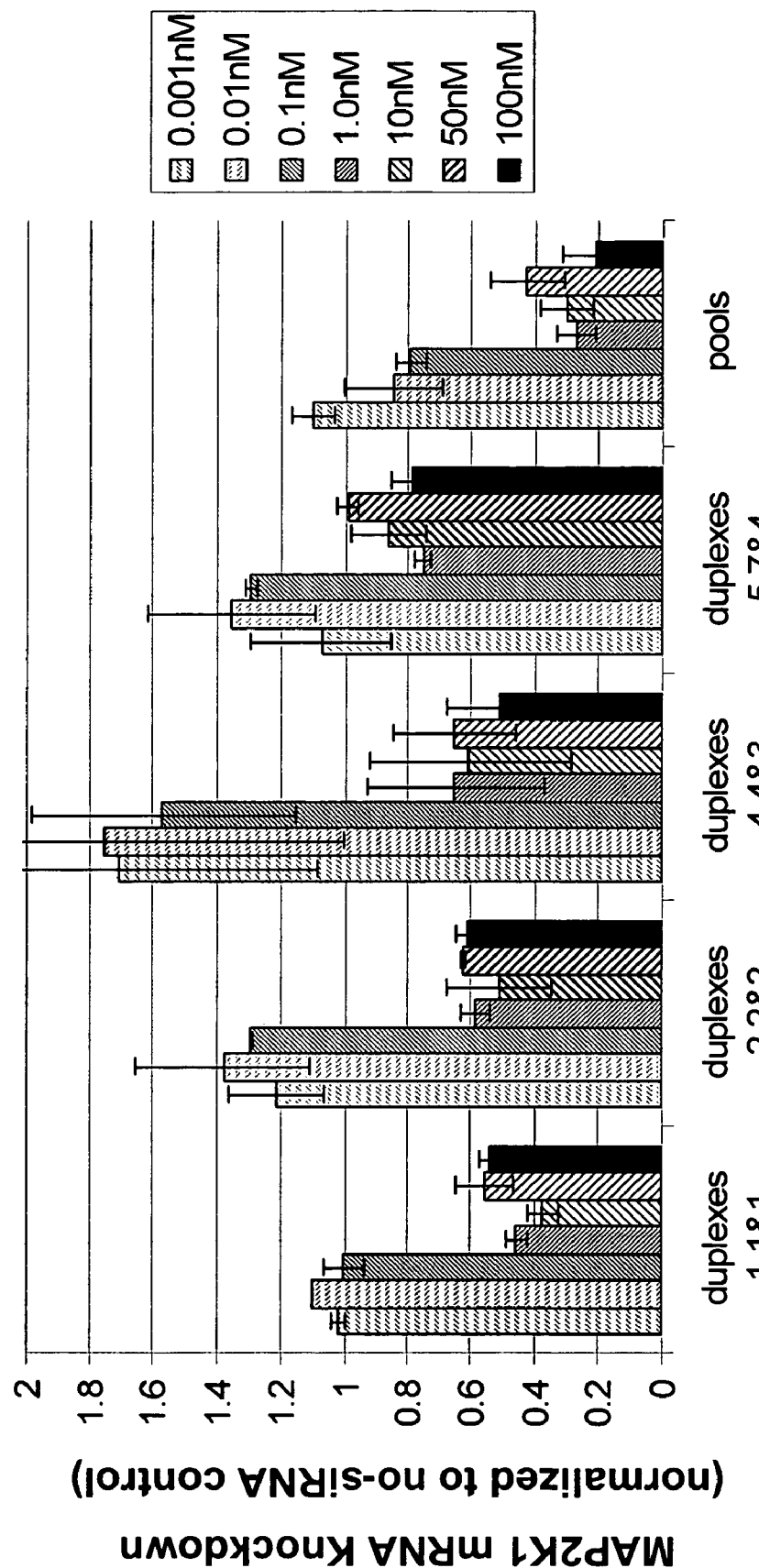

FIGS. 25A-25C are graphical representations of an embodiment of siRNA RTF protocols that compare the effectiveness of individual siRNA and pools of siRNA directed against, GAPDH, MAP2K2, and MAP2K1 at varying concentrations. FIG. 25A shows the GAPDH knockdown in the presence of GAPDH duplex 1, MAP2K2 duplex 1, and MAP2K1 duplex 1 (1, 1&1); and GAPDH knockdown in the presence of GAPDH duplex 2, MAP2K2 duplex 2, and MAP2K1 duplex 2 (2, 2&2); GAPDH knockdown in the presence of GAPDH duplex 4, MAP2K2 duplex 4, and MAP2K1 duplex 3 (4, 4&3); GAPDH knockdown in the presence of GAPDH duplex 5, MAP2K2 duplex 7, and MAP2K1 duplex 4 (5, 7&4); and GAPDH knockdown in the presence of GAPDH, MAP2K2, and MAP2K1 pools consisting of all of the before mentioned duplexes. FIG. 25B shows the MAP2K2 knockdown in the presence of all of the duplex combinations described in FIG. 25A. FIG. 25C shows the MAP2K1 knockdown in the presence of all the duplex combinations described in FIG. 25A.

DETAILED DESCRIPTION OF THE PREFERRED EMBODIMENTS

Generally, the present invention is related to an apparatus and system for use in effecting gene silencing in cells. The apparatus includes plates with wells that have dry gene silencing compositions comprised of siRNA, which can be solubilized or suspended for use in RTF protocols. The systems, which can be provided as kits, include the plates and polynucleotide carriers that can be combined with the siRNA to form a transfection complex capable of entering a cell in order to deliver the siRNA. Additionally, the kits can include an siRNA solubilizing or suspending aqueous medium, polynucleotide carriers in corresponding carrier solutions, cell culture media, and the like.

The well plates, systems, kits, and methods of the present invention can be configured for use in high content screening ("HCS") and high throughput screening ("HTS") applications with or without the use of laboratory automation equipment. Also, the well plates, systems, kits, and methods can also be used with automated systems, such as robotic systems. However, the well plates, systems, kits, and methods can also be used in RTF protocols without the aid of automated delivery systems, or robotics, and thus can provide an efficient alternative to costly robotic delivery systems for laboratories using manual processing. Thus, the well plates, systems, kits, and methods provide versatility in choice such that high throughput screening can be done in a cost effective manner.

The following terminology is defined herein to clarify the terms used in describing embodiments of the present invention and is not intended to be limiting. As such, the following terminology is provided to supplement the understanding of such terms by one of ordinary skill in the relevant art.

As used herein, the term "2' modification" is meant to refer to a chemical modification of a nucleotide that occurs at the second position atom. As such, the 2' modification can include the conjugation of a chemical modification group to the 2' carbon of the ribose ring of a nucleotide, or a nucleotide within an oligonucleotide or polynucleotide. Thus, a 2' modification occurs at the 2' position atom of a nucleotide.

As used herein, the term "aliphatic" is meant to refer to a hydrocarbyl moiety, such as an alkyl group, that can be straight or branched, saturated or unsaturated, and/or substituted or unsubstituted, which has twenty or less carbons or hetero atoms in the backbone. An aliphatic group may comprise moieties that are linear, branched, cyclic and/or heterocyclic, and contain functional groups such as ethers, ketones, aldehydes, carboxylates, and the like. Substitutions within an aliphatic group can include any atom or group that can be tolerated in the aliphatic moiety, including but not limited to halogens, sulfurs, thiols, thioethers, thioesters, amines (primary, secondary, or tertiary), amides, ethers, esters, alcohols, oxygen, and the like. Further, aliphatic groups may also contain hetero substitutions, which are substitutions of carbon atoms, by hetero atoms such as, for example, nitrogen, oxygen, phosphorous, or sulfur.

As used herein, the term "alkyl" is meant to refer to a hydrocarbyl moiety that has both carbons and hydrogens in a chain. Preferably, alkyl moieties consist of hydrogens and carbons only. An alkyl moiety may be linear, branched and/or cyclic. Preferably the alkyl moiety is not branched and not cyclic, is fully saturated, and is unsubstituted.

Exemplary alkyl groups include but are not limited to moieties such as, for example, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and alkyl groups of higher number of carbons, as well as 2-methylpropyl, 2-methyl-4-ethylbutyl, 2,4-diethylpropyl, 3-propylbutyl, 2,8-dibutyldecyl, 6,6-dimethyloctyl, 6-propyl-6-butyloctyl, 2-methylbutyl, 2-methylpentyl, 3-methylpentyl, 2-ethylhexyl, isopropyl, isobutyl, isopentyl, and the like The term alkyl also encompasses alkenyl groups, such as vinyl, allyl, aralkyl and alkynyl groups. Substitutions of alkyl groups can be made, with any suitable atom, as long as such a replacement does not substantially interfere with the function of the molecule wherein the alkyl group is replaced.

As used herein, the term "antisense strand" is meant to refer to a polynucleotide or region of a polynucleotide that is at least substantially (e.g., about 80% or more) or 100% complementary to a target nucleic acid of interest. Also, the antisense strand of a dsRNA is complementary to its sense strand. An antisense strand may be comprised of a polynucleotide region that is RNA, DNA, or chimeric RNA/DNA. Additionally, any nucleotide within an antisense strand can be modified by including substituents coupled thereto, such as in a 2' modification. The antisense strand can be modified with a diverse group of small molecules and/or conjugates. For example, an antisense strand may be complementary, in whole or in part, to a molecule of messenger RNA ("mRNA"), an RNA sequence that is not mRNA inlcuding non-coding RNA (e.g., tRNA and rRNA), or a sequence of DNA that is either coding or non-coding. The terms "antisense strand" and "antisense region" are intended to be equivalent and are used interchangeably.

As used herein, the terms "complementary" and "complementarity" are meant to refer to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine.

Perfect complementarity or 100% complementarity refers to the situation in which each nucleotide unit of one polynucleotide strand can hydrogen bond with a nucleotide unit of an anti-parallel polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. "Substantial complementarity" refers to polynucleotide strands exhibiting 79% or greater complementarity, excluding regions of the polynucleotide strands, such as overhangs, that are selected so as to be non-complementary. Accordingly, complementarity does not consider overhangs that are selected so as not to be similar or complementary to the nucleotides on the anti-parallel strand.

As used herein, the term "conjugate" is meant to refer to a molecule, large molecule, or macromolecular structure that is coupled with either the sense strand or antisense strand of an siRNA. That is, the moiety coupled to the siRNA is considered the conjugate. For clarity purposes, the siRNA can include a conjugate that is coupled thereto by a covalent bond, ionic interaction, and like couplings. Usually, a conjugate is coupled with an siRNA in order to impart a functionality other than increasing the stabilization or targeting specificity. For examples, some conjugates, such as cholesterol, can be used to enhance the ability of the siRNA to enter a cell. Other conjugates can be labels that are used to detect transfection or the presence of the siRNA in the cell. Usually, the conjugate is coupled to the siRNA through a linker group.

As used herein, the term "deoxynucleotide" is meant to refer to a nucleotide that lacks a hydroxyl group (e.g., OH group) at the 2' position of its sugar moiety. Instead, a hydrogen is bonded to the 2' carbon. Thus, an RNA molecule that comprises one or more deoxynucleotides refers to the lack of an OH group at the 2' position of the sugar moiety, and has a hydrogen bonded directly to the 2' carbon. Similarly, the terms "deoxyribonucleotide" and "DNA" include a ribonucleotide or polyribonucleotide comprising at least one sugar moiety that has a hydrogen at its 2' position.

As used herein, the terms "dried" or "dry" as used in connection with gene silencing compositions is meant to refer to a composition that is not fluidic and does not flow. However, this does not exclude small amounts of water or other solvents, and includes amounts of water remaining in an RNA preparation that has equilibrated at standard or ambient conditions, for example, at one atmosphere of pressure, room temperature, and ambient humidity, such that the preparation is not in a substantially liquid form but instead is "dried" in the well. For example, an siRNA preparation is "dried" or substantially "dry" if, at about one atmosphere pressure, at about 20 to 40° C., and at about 50 to about 95% humidity, the preparation is equilibrated and, when the well plate is inverted or tilted to, for example, 90° from horizontal, the RNA preparation does not displace or flow within the well. This is in comparison to a liquid preparation which would flow or run when tilted. In various embodiments, methods for using the dry gene silencing composition in order to perform a transfection can include solubilizing or suspending the dried preparation in a suitable aqueous medium to form a mixture. Additionally, the suitable aqueous medium can include an polynucleotide carrier capable of facilitating introduction of the siRNA into a cell, and exposing the mixture to one or more cells to achieve transfection.

As used herein, the term "duplex region" is meant to refer to the region in two complementary or substantially complementary polynucleotides that form base pairs with one another, either by Watson-Crick base pairing or any other manner that allows for a stabilized duplex between the polynucleotide strands. For example, a polynucleotide strand having 21 nucleotide units can base pair with another polynucleotide of 21 nucleotide units, yet only 19 bases on each strand are complementary such that the "duplex region" has 19 base pairs. The remaining bases may, for example, exist as 5' and/or 3' overhangs. Further, within the duplex region, 100% complementarity is not required, and substantial complementarity is allowable within a duplex region. Substantial complementarity refers to 79% or greater complementarity and can result from mismatches and/or bulges. For example, a single mismatch in a duplex region consisting of 19 base pairs results in 94.7% complementarity, rendering the duplex region substantially complementary.

As used herein, the term "functionality" is meant to refer to the level of gene specific silencing induced by an siRNA. In general, functionality is expressed in terms of percentages of gene silencing. Thus, 90% silencing of a gene (e.g., F90) refers to situations in which only 10% of the normal levels of gene expression are observed. Similarly, 80% silencing of a gene (e.g., F80) refers to situations in which only 20% of the normal levels of gene expression are observed.

As used herein, the term "gene silencing" is meant to refer to a process by which the expression of a specific gene product is inhibited by being lessened, attenuated, and/or terminated. Gene silencing can take place by a variety of pathways. In one instance, gene silencing can refer to a decrease in gene product expression that results from the RNAi pathway, wherein an siRNA acts in concert with host proteins (e.g., RISC) to degrade mRNA in a sequence-dependent manner. Alternatively, gene silencing can refer to a decrease in gene product expression that results from siRNA mediated translation inhibition. In still another alternative, gene silencing can refer to a decrease in gene product expression that results from siRNA mediated transcription inhibition. The level of gene silencing can be measured by a variety of methods, which can include measurement of transcript levels by Northern Blot Analysis, B-DNA techniques, transcription-sensitive reporter constructs, expression profiling (e.g., DNA chips), and related technologies and assays. Alternatively, the level of gene silencing can be measured by assessing the level of the protein encoded by a specific gene that is translated from the corresponding mRNA. This can be accomplished by performing a number of studies including Western Analysis, measuring the levels of expression of a reporter protein, such as colorimetric or fluorescent properties (e.g., GFP), enzymatic activity (e.g., alkaline phosphatases), or other well known analytical procedures.

As used herein, the term "internucleotide linkage" is meant to refer to the type of bond or link that is present between two nucleotide units in a polynucleotide, wherein the linkage may be modified or unmodified. The phrase "modified internucleotide linkage" includes all modified internucleotide linkages now known or later developed. Internucleotide linkages may have associated counterions, and the phrase is meant to include such counterions and any coordination complexes that can form at the internucleotide linkages.

As used herein, the term "mismatch" includes a situation in which Watson-Crick base pairing does not take place between a nucleotide of a sense strand and a nucleotide of an antisense strand, where the non-base paired nucleotides are flanked by a duplex comprising base pairs in the 5' direction of the mismatch beginning directly after (e.g., in the 5' direction) the non-base paired nucleotides and in the 3' direction of the mismatch beginning directly after (e.g., in the 3' direction) the non-base paired nucleotides. An example of a mismatch would be an A across from a G, a C across from an A, a U across from a C, an A across from an A, a G across from a G, a C across from a C, and the like. Mismatches are also meant to include an abasic residue across from a nucleotide or modified nucleotide, an acyclic residue across from a nucleotide or modified nucleotide, a gap, or an unpaired loop. In its broadest sense, a mismatch as used herein includes any alteration at a given position that decreases the thermodynamic stability at or in the vicinity of the position where the alteration appears, such that the thermodynamic stability of the duplex at the particular position is less than the thermodynamic stability of a Watson-Crick base pair at that position.

As used herein, the term "nucleotide" is meant to refer to a ribonucleotide, a deoxyribonucleotide, or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotides are well known in the art. Nucleotide analogs include nucleotides having modifications in the chemical structure of the base, sugar and/or phosphate, including, but not limited to, 5'-position pyrimidine modifications, 8'-position purine modifications, modifications at cytosine exocyclic amines, substitution of 5-bromo-uracil, and 2'-position sugar modifications (e.g., 2' modifications). Such modifications include sugar-modified ribonucleotides in which the 2'-OH is replaced by a group such as an H, OR, R, halo, SH, SR, $NH_2$, NHR, $NR_2$, or CN, wherein R is an alkyl or aliphatic moiety. Nucleotide analogs are also meant to include nucleotides with bases such as inosine, queuosine, xanthine, sugars such as 2'-methyl ribose, non-natural phosphodiester linkages such as methylphosphonates, phosphorothioates, and peptides. Also, reference to a first nucleotide or nucleotide at a first position refers to the nucleotide at the 5'-most position of a duplex region, and the second nucleotide is the next nucleotide toward the 3' end. In instances the duplex region extends to the end of the siRNA, the 5' terminal nucleotide can be the first nucleotide.

As used herein, the term "modified bases" is meant to refer to nucleotide bases such as, for example, adenine, guanine, cytosine, thymine, uracil, xanthine, inosine, and queuosine that have been modified by the replacement or addition of one or more atoms or groups. Some examples of types of modifications to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O— and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

Additionally, the term "nucleotide" is meant to include what are known in the art as universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

As used herein, the terms "off-target" and "off-target effects" are meant to refer to any instance where an siRNA, such as a synthetic siRNA or shRNA, is directed against a given target mRNA, but causes an unintended effect by interacting either directly or indirectly with another mRNA, a DNA, a cellular protein, or other moiety in a manner that reduces non-target protein expression. Often, this can happen when an siRNA interacts with non-target mRNA that has the same or similar polynucleotide sequence as the siRNA. For example, an "off-target effect" may occur when there is a simultaneous degradation of other non-target mRNA due to partial homology or complementarity between that non-target mRNA and the sense and/or antisense strand of the siRNA.

As used herein, the term "on-target" is meant to refer to a set of modifications of an siRNA that increase the likelihood that the siRNA will preferentially target and interact with a target mRNA or DNA so as to inhibit production of the polypeptide encoded thereby. This increases the specificity of the siRNA for silencing the target gene. For example, an on-target modification can include a siRNA where the first and second nucleotide of the sense region each has a 2'-O-methyl moiety, and the antisense strand is phosphorylated at its 5' end, wherein such an on-target modification also refers to a proprietary modification coined On-Target™ (Dharmacon, Inc.). In any event, on-target modifications can be used to help reduce off-target effects. Also, an siRNA can have a sense region that has complementarity to the antisense region of the siRNA, and wherein the antisense region is the region has complementarity to a target mRNA.

As used herein, the term "polynucleotide" is meant to refer to polymers of nucleotides linked together through internucleotide linkages. Also, a polynucleotide includes DNA, RNA, DNA/RNA, hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides. Also, polynucleotides include nucleotides with various modifications or having attachments of various entities or moieties to the nucleotide units at any position.

As used herein, the term "polyribonucleotide" is meant to refer to a polynucleotide comprising two or more modified or unmodified ribonucleotides and/or their analogs. The term "polyribonucleotide" is used interchangeably with the term "oligoribonucleotide."

As used herein, the terms "rational design" and "rationally designed" are meant to refer to the selection or design of one or more siRNA(s) for use in a gene silencing application based upon one or more criteria that are independent of the target sequence. As such, rationally designed siRNA are selected to specifically interact with and inhibit polypeptide translation from a selected mRNA. Thus, for any one target mRNA there may be hundreds of potential siRNA having 18 to 31 base pairs that are 100% complementary to the target mRNA. In part, this is because a single mRNA may have multiple sequences that can be specifically targeted by the siRNA. However, it is likely that not all of the siRNA will have equal functionality. Through empirical studies, a number of other factors including the presence or absence of certain nitrogenous bases at certain positions, the relative GC content, and the like, can affect the functionality of particular siRNA. Additional information regarding rationally designed siRNA can be found in commonly owned U.S. patent application Ser. No. 10/714,333, filed on Nov. 14, 2003, related PCT application PCT/US03/36787, published on Jun. 3, 2004 as WO 2004/045543 A2, U.S. patent application Ser. No. 10/940,892, filed on Sep. 14, 2004, published as U.S. Patent Application Publication 2005/0255487, related PCT application PCT/US04/14885, filed May 12, 2004, and U.S. Patent Application Publication 2005/0246794, wherein each is incorporated herein by reference.

As used herein, the term "reverse transfection" and abbreviation "RTF" are each meant to refer to a process for introducing nucleic acid, such as an siRNA, into a cell. Such an introduction of an siRNA into a cell can be accomplished by combining the nucleic acid and cell in a well, wherein the cell has not yet been previously adhered or maintained on the growth surface. The reverse transfection proceeds by contacting the nucleic acid onto a cellular surface in a manner such that the nucleic acid can enter into the cell. Usually, the siRNA is complexed with a lipid or other polynucleotide carrier prior to being contacted to the cells. Reverse transfection differs from forward transfection because the cells have not been seeded and maintained on the cellular growth surface of a well or other container before addition of the siRNA.

As used herein, the terms "ribonucleotide," "ribonucleic acid," and "RNA" are meant to refer to a modified or unmodified nucleotide or polynucleotide comprising at least one ribonucleotide unit. Typically, all nucleotide units are ribonucleotides. An unmodified ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage. Ribonucleotides, ribonucleic acid, and RNA are well known terms in the art.

As used herein, the term "sense strand" is meant to refer to a polynucleotide or region that has the same nucleotide sequence, in whole or in part, as a target nucleic acid such as a messenger RNA or a sequence of DNA. The term "sense strand" includes the sense region of a polynucleotide that forms a duplex with an antisense region of another polynucleotide. Also, a sense strand can be a first polynucleotide sequence that forms a duplex with a second polynucleotide sequence on the same unimolecular polynucleotide that includes both the first and second polynucleotide sequences. As such, a sense strand can include one portion of a unimolecular siRNA that is capable of forming hairpin structure, such as an shRNA. When a sequence is provided, by convention, unless otherwise indicated, it is the sense strand or region, and the presence of the complementary antisense strand or region is implicit. The phrases "sense strand" and "sense region" are intended to be equivalent and are used interchangeably.

As used herein, the term "siRNA" is meant to refer to a small inhibitory RNA duplex that induces gene silencing by operating within the RNA interference ("RNAi") pathway. These siRNA are dsRNA that can vary in length, and can contain varying degrees of complementarity between the antisense and sense strands, and between the antisense strand and the target sequence. Each siRNA can include between 17 and 31 base pairs, more preferably between 18 and 26 base pairs, and most preferably 19 and 21 base pairs. Some, but not all, siRNA have unpaired overhanging nucleotides on the 5' and/or 3' end of the sense strand and/or the antisense strand. Additionally, the term "siRNA" includes duplexes of two separate strands, as well as single strands that can form hairpin structures comprising a duplex region, which may be referred to as short hairpin RNA ("shRNA").

As used herein, the terms "siRNA library" or "RTF siRNA library" is meant to refer to an array of siRNAs for use in analyzing a particular biological pathway or gene target. An siRNA library comprises various siRNA pool reagents for analyzing a particular pathway or gene target. A pool typically comprises two or more non-identical siRNA directed against a single target gene. Usually, a pool includes four or more non-identical siRNA that are rationally designed. An exemplary list of siRNA libraries is provided in Table 1 below. Sequences used in certain siRNA libraries, including pool reagents, are provided in Table I and Table II of the incorporated provisional application.

As used herein, the terms "siRNA pool," "pool," "pool of siRNAs," and "pool reagents" are meant to refer to two or more siRNA, typically four siRNA, directed against a single target gene, mRNA, and/or translation of a protein. The siRNA of the pool reagent can be rationally designed by being selected according to non-target specific criteria. For example, two nanomoles of each pool reagent can be sufficient for transfecting cells in about 200 wells of multiple 96-well plates, using 100 nM siRNA concentration. Pool reagents can be plated as a pool (i.e., the two or more siRNA of Dharmacon's SMARTpool® Reagent in a single transfection well). The individual siRNAs that comprise the SMARTpool® Reagent, sometimes referred to herein as SMARTselection™ siRNA (Dharmacon, Inc.), can also be plated individually on the same plate as the SMARTpool® Reagent.

As used herein, the term "target" is used in a variety of different forms throughout this document and is defined by the context in which it is used. The term "target gene" is meant to refer to the gene that encodes the protein to be silenced by the siRNA, and encodes for the production of the target mRNA. The term "target mRNA" is meant to refer to an mRNA against which a given siRNA is direct to silence the transcription of the polypeptide product. The term "target sequence" and "target site" are meant to refer to a sequence within the mRNA, miRNA, or DNA coding or promoter region to which the sense strand of an siRNA exhibits varying degrees of homology and the antisense strand exhibits varying degrees of complementarity. The term "target polypeptide" or "target protein" is meant to refer to the gene product encoded by the target gene, target mRNA, and/or target sequence. The term "siRNA target" can refer to the gene, mRNA, or protein against which the siRNA is directed to for silencing. Similarly, "target silencing" can refer to the state of silencing a gene, or the corresponding mRNA or protein.

As used herein, the term "transfection" is meant to refer to a process by which nucleic acids are introduced into a cell. The list of nucleic acids that can be transfected is large and includes, but is not limited to, siRNA, shRNA, sense and/or anti-sense sequences, DNA, RNA, and the like. There are multiple modes for transfecting nucleic acids into a cell including, but not limited to, electroporation, particle bombardment, calcium phosphate delivery, DEAE-dextran delivery, lipid delivery, polymer delivery, molecular conjugate delivery (e.g., polylysine-DNA or -RNA conjugates, antibody-polypeptide conjugates, antibody-polymer conjugates, or peptide conjugates), microinjection, laser- or light-assisted microinjection, optoporation or photoporation with visible and/or nonvisible wavelengths of electromagnetic radiation, and the like. Transfections can be "forward transfections" whereby cells are first plated in wells and then treated with a nucleic acid or they can be "reverse transfections" (RTF) whereby the nucleic acid is combined with the cells before or during being plated and/or attached to the bottom of the well. Any mode of transfecting cells, such as those described above, can be used with the present invention by inducing the nucleic acid to be introduced into a cell after the siRNA is solubilized or suspended in the aqueous medium to implement reverse transfection. Details regarding a mode of reverse transfection are described in more detail below.

As used herein, the term "well plate" is meant to refer to a substrate that is divided into distinct regions that prevent migration from one distinct region to another distinct region, wherein the distinct regions are wells. For example, each well of a multi-well well plate may contain a horizontal base that may be curved or flat, as well as have sidewalls. Alternatively, the sidewalls may come together at a particular angle or curvature such that there is no discrete horizontal base portion. As described below, well plates with a flat or substantially flat horizontal base are preferred in many embodiments of the present invention, especially when used with adherent cells. Regardless of the form, most importantly each well in a well plate is physically separated from other wells. The wells typically are open on the top to allow for easy addition and removal of materials. Common well plates typically comprise 48, 96, 384, or 1356 wells and are composed of polystyrene, polypropylene, polycarbonate, glass or equivalent materials. Wells in plates can be coated with a range of compounds or subjected to a range of physical treatments that may enhance siRNA and/or cell attachment. Wells in plates can also be designed to hold a range of liquid volumes and to provide a range of surface areas, especially along a horizontal base. The wells in the figures herein are schematically shown as squares for the sake of simplicity only, but can be any suitable shape. Additionally, well plates are well known in the art.

The use of units to define measurable quantities of material, such as concentration, weight, and volume, are intended to be those that are routinely employed by those of skill in the art. Additionally, the units are preferably interpreted to correspond with the metric system. Also, the use of "u," as in "ug" or "uL" is meant to refer to "micro" as applied to microgram and microliter, respectively.

Additionally, while the foregoing term definitions are intended to supplement the knowledge of one of ordinary skill in the art, not every term within this document has been defined. As such, the undefined terms are intended to be construed with the knowledge of one of ordinary skill in the art and/or the plain meaning of the term. Additionally, the foregoing terms are not intended to be limited by the examples provided therein, but are intended to be useful in understanding and practicing the invention as described herein.

I. Reverse Transfection

Generally, the present invention provides well plates, systems, kits, and methods for implementing reverse transfection of siRNA. The present invention provides for reverse transfection protocols with siRNA that are improved and more efficient. These improvements are particularly advantageous for manual assays as well as high throughput screenings.

In one embodiment, the present invention includes a method of reverse transfection for introducing siRNA into a cell to effect gene silencing. Such a method can include providing a well plate that includes a well having a substantially dry gene silencing composition. The gene silencing composition can include an siRNA which silences a target gene so that the production of the corresponding gene product is inhibited or stopped. The siRNA is present in the well as part of the dry gene silencing composition so that the plates can be prepared, sealed, stored, and/or shipped long before an RTF protocol is performed. In part, this is because the dry gene silencing composition can stably retain the siRNA in a functional condition within the well, and be resuspended or resolubilized with an aqueous solution during the RTF protocol. Thus, a well plate having the gene silencing composition can be manufactured and hermetically sealed in an inert environment, wherein the plate can include different wells with predefined types of siRNA for specific gene targets. Such types of siRNA and intended gene targets for silencing are described in more detail below.

An aqueous medium can be added to each well that contains a gene silencing composition so as to suspend or solubilize the siRNA into the solution. The aqueous medium is allowed to solubilize the siRNA for a sufficient duration. Optionally, the aqueous medium or an additional medium is comprised of a polynucleotide carrier. As such, a polynucleotide carrier can also be added to each well having the gene silencing composition, and the plate can be maintained for an incubation period sufficient for siRNA-carrier complexes to form. However, polynucleotide carriers are not necessary in some embodiments, and the siRNA can be transfected into the cells using other modes of transfection.

After the siRNA is adequately solubilized or suspended, cells are added to the well under conditions that permit the siRNA to be introduced into the cell. The cells can be added in an amount of about $1 \times 10^3$ to about $3.5 \times 10^4$ cells per about 0.35 $cm^2$ to about 0.35 $cm^2$ of cell growth surface area. The conditions that promote the siRNA entering the cell can be described by typical cell culture techniques used for plating cells that are well known in the art. That is, the cells can be added to the well that contains the siRNA in a manner similar to ordinary plating. The well containing the siRNA and cells can be incubated for a duration sufficient for gene silencing to occur, which is typically less than 72 hours, more preferably less than 48 hours, and most preferably about 24 hours or less.

In one embodiment, the RTF protocol can include adding a polynucleotide carrier to the well so as to form a siRNA-carrier complex, wherein the siRNA-carrier complex is suspended or solubilized in the solution. After the cells are added, the siRNA-carrier complex can be contacted to the cell to induce endocytosis of the complex. As such, the polynucleotide carrier can be added as part of the aqueous solution or in addition thereto. Thus, the polynucleotide carrier can be presented in an aqueous medium as either solubilized or suspended therein. The polynucleotide carrier can be a lipid, cationic polymer, lipopolymer, and the like.

After the cells are combined with the siRNA, the well plate can be maintained under conditions so that cell growth, cell division, and/or gene silencing occurs. Usually, the cells are maintained in the presence of the siRNA for about 6 to about 72 hours before gene silencing is assessed, more preferably about 12 to about 36 hours, and most preferably for about 24 to about 48 hours. However, it should be recognized that the cells are incubated with the siRNA for a time period sufficient for silencing a gene so that the amount corresponding gene product decreases. As such, the production of a target polypeptide can be silenced by at least about 50%, more preferably by at least about 70%, even more preferably by at least about 80%, and most preferably by at least about 90%.

In instances where cells that grow in suspension are the target cell, such cells can be added to the wells at an appropriate cell density and plates can be spun under low gravity forces that are not detrimental to cell viability to bring the cells and lipids into close proximity on the bottom of the well.

In one embodiment, the cells transfected with the siRNA in the RTF format can be assessed for cell viability, gene silencing, and the like. The cell viability studies can be performed in the well plate in accordance with well known procedures. Additionally, the gene silencing can also be assessed with the contents in the well by various techniques well known in the art to assess the presence or absence of target proteins. Alternatively, the amount of gene silencing can be assessed by removing the contents from the well by well known assays. In various embodiments, the well is designed to be compatible with optical detection systems such as, for example, UV, luminescence, fluorescence, or light scattering detection systems. In embodiments compatible with optical detection systems, the walls of the well can be made opaque, or rendered such that light scattering that can interfere with optical detection is reduced or minimized.

In one embodiment, the results of the RTF protocol to induce gene silencing can be detected or monitored using systems for performing high content screening ("HCS") or high throughput screening ("HTS"). An HCS analysis can be used to measure specific translocation and morphology changes, receptor trafficking, cytotoxicity, cell mobility, cell spreading, and the like. HCS studies can be performed on an ArrayScan® HCS Reader, or a KineticScan® HCS Reader (Cellomics, Inc.) Additional information on HCS can be found in U.S. Pat. Nos. 6,902,883, 6,875,578, 6,759,206, 6,716,588, 6,671,624, 6,620,591, 6,573,039, 6,416,959, 5,989,835, wherein each is incorporated herein by reference. HTS analyses can be performed using a variety of available readers, typically of the fluorescence from each well as a single measurement.

In one embodiment, the invention includes a well plate configured for having the contents of a well transferred to a location, device, or system wherein detection of the results of an siRNA RTF protocol is carried out. As such, wet transfer detection systems can be employed that include systems wherein cells are transferred from wells to a substrate such as nitrocellulose. Following the transfer of the well contents to the substrate a detection protocol can be implemented. An example of such a well plate transfer system can include nitrocellulose, wherein the well contents can be treated such that cell membranes are permeabilized or disrupted so as to gain access to intracellular contents. The transfer of the well contents to the nitrocellulose can be achieved by any suitable method including gravity or use of a vacuum manifold. The nitrocellulose containing the well contents can then be further subjected to a detection protocol that uses antibody-based detection systems and the like to detect the presence or level of one or more contents of the cells that comprise a particular well.

II. Optimizing siRNA RTF

Due to the unique and highly sensitive nature of the RNAi pathway, methodologies particularly useful for introducing pools of siRNAs into cells have been developed. Accordingly, new RTF methodologies were developed for use with pools of siRNAs ("siRNA RTF"). As such, recently developed protocols for implementing siRNA RTF were modified by augmenting such protocols with recently developed siRNA technologies based on rationale design, siRNA stabilization, siRNA targeting specificity, and pooling siRNAs. Thus, improved methods for implementing gene silencing with siRNA RTF protocols are presented herein.

In one embodiment, the present invention may be used in connection with a diverse type of cells from a diverse set of species of the plant and animal kingdoms. Preferably, the cells are from mammalian species including cells from humans, other primates, horses, pigs, and mice. For example, cells can be HT-29 cells, LNCaP-FGC cells A549 cells, MDA-MB453 cells, HepG2 cells, THP-1 cells, miMCD-3 cells, HEK293 cells, 3T3 cells, HeLaS3 cells, MCF7 cells, Cos-7 cells, CHO-K1 cells, BxPC-3 cells, DU145 cells, Jurkat cells, PC-3 cells, Capan-1 cells, HuVEC cells, HuASMC cells, and the like. Additionally, any species of plant may be used to determine an effect of gene silencing.

The number of cells per well, which is referred to as the cell density, is an important parameter of successful siRNA RTF. It has been found that siRNA RTF protocols can have more favorable results with lower cell densities compared to RTF protocols using DNA. For example, 96-well plates can include cell densities of about 1,000-35,000 cells per well, more preferably about 2,000-30,000 cells per well, even more preferred are cell densities of about 2,500-20,000 cells per well, still more preferably about 3,000-15,000 cells per well, and most preferable are cell densities of about 3,500-10,000 cells per well. Also, the number of cells per well can be extrapolated to wells having different cell culture areas. One possible equation for calculating the appropriate number of cells that are placed in a given well is based on a 96-well plate having a cell culture area of about 0.3 $cm^2$ to about 0.35 $cm^2$, wherein well # 2 is the 96-well plate, and is described as follows:

$$\text{cells in well \#1} = \left(\frac{\text{area of well \#1}}{\text{area of well \#2}}\right) \times \text{cells in well \#2}$$

Additionally, siRNA RTF protocols can be optimized in order to determine whether a particular mode of transfection can be useful or provide optimal results. Accordingly, any mode of transfection can be employed in the siRNA RTF protocol described herein. Polynucleotide carrier over a wide range of concentrations by using a robust and easily-transfected cell line (e.g., HeLa) with a well-characterized siRNA, such as positive control siRNAs, over commonly used ranges of cell density and total siRNA concentrations. Accordingly, cell viability and transfection efficacy can be assayed with the foregoing concentration gradients. Thus, optimization studies can be performed with a particular mode of transfection or a polynucleotide carrier concentration gradient in order to determine which mode of transfection can produce highly efficient gene silencing without inducing unfavorable cell toxicity.

In one embodiment, the present invention is directed to optimization of siRNA RTF protocols for implementing gene silencing through the RNAi pathway. As such, optimization of siRNA RTF can include any of the following: (1) selecting the type of plate; (2) selecting an appropriate solution to solubilize or suspend the siRNA for being deposited and dried in a well; (3) selecting a particular siRNA to silence specific genes; (4) identifying any modifications or conjugates that can be applied to the individual siRNA in order to enhance siRNA stability and/or specificity; (5) applying and drying the siRNA on a solid surface so that it can be solubilized or suspended in an appropriate aqueous medium; (6) selecting an appropriate mode of transfection; (7) selecting a polynucleotide carrier for siRNA such as a lipid; (8) solubilizing or suspending an siRNA; (9) complexing the siRNA with the polynucleotide carrier to form an siRNA-carrier complex; and (10) combining the siRNA-carrier complex with the cell type or types of choice. Thus, optimizing siRNA RTF protocols can result in a dramatic improvement over previous forward and reverse transfection procedures.

In one embodiment, the present invention can include siRNA RTF protocols to implement along with the foregoing optimizations, which can include any of the following: (a) applying at least one siRNA to two or more wells of a multi-well plate, wherein the siRNA is a control siRNA targeting a standard gene; (b) drying the siRNA on the bottom of each well; (c) adding an aqueous solution such as a media or buffer to the siRNA in each well in order to solubilize or suspend the siRNA, and optionally the solution includes a polynucleotide carrier so that a siRNA-carrier complex can form; (d) adding an appropriate number of cells to each well in which the siRNA is already in solution alone or as an siRNA-carrier complex; (e) after cells have been added, causing the siRNA to enter the cells, which can be by any mode of transfection; and (f) maintaining the plate under conditions in which transfection of the cells by the siRNA can occur. Following transfection, the cells are subjected to conditions, such as liquid media, temperature, gas partial pressures, and the like, in which cell growth and/or cell division will occur and gene silencing may occur. These conditions can be, but not necessarily, the same as the conditions under which transfection occurs, and are well known in the art.

III. Well Plates

In one embodiment, the present invention includes the use of gene silencing solutions dried in the bottom of a well in a well plate. The well plates used in connection with the present invention are preferably formatted and distinct well arrays (e.g., a 48, 96, 384, or 1536-well plate) that can be purchased from any number of commercial sources of cell culture plates and other cell culture surface-containing devices, including products such as NUNC™, NUNCLON™, MICROWELL™ and FLUORONUNC™ plates (e.g., each of which may be obtained from Nalge Nunc International of Rochester, N.Y., and Nunc A/S of Denmark), COSTAR™, COSTAR THERMOWELL™ and CORNING™ plates (e.g., each of which is available from Corning), BD FALCON™ and OPTILUX™ plates (e.g., available from Becton, Dickinson and Company) and GREINER™, CELL COAT™ and CELLSTAR™ plates (e.g., available from Greiner Bio-One).

In one embodiment, the well plate can be characterized by being configured to be suitable for cell growth and propagation. A well plate can be made of glass, polystyrene, other polymeric material or any equivalent materials, and can have rounded and/or flat well floors. However, certain analytical equipment can have enhanced functionality when using flat bottom surfaces. Additionally, wells having substantially flat floors can provide uniform cell spacing and monolayer formation. Thus, it can be preferable for the well floor to have a substantially flat bottom surface. The well floor can have a physical or chemical treatment, such as irradiation, corona discharge, plasma discharge, or microwave plasma discharge of polystyrene. Such treatments can be conventional in tissue culture surfaces upon which adherent eukaryotic cells may adhere and grow. Additionally, the wells may not be modified by any chemical coating, or they can be coated with poly-L-lysine ("PLL"), laminin, collagen, or equivalent substances that improve the adherence of cells.

Additionally, it can be preferable for each plate to have between 6 and 2000 wells, and more preferably having 1536 wells, 384 wells, or 96 wells. Also, it can be preferable for the wells to have a volume that varies between about 5 to about 2000 microliters ("uL"), and the total culture area, which is represented by the well bottom surface or cell floor, to range between about 0.02 $cm^2$ to about 4.2 $cm^2$, and about 0.3 $cm^2$ to about 0.35 $cm^2$ for a 96-well plate.

Furthermore, in some instances it can be preferably that the wells are not coated with materials such as MATRIGEL™ (Beckinson Dickerson), or are not manufactured with methods similar to those used to construct CELLBIND™ plates (Corning). In part, this is because both of these technologies are conventionally used to enhance cell attachment but have been found to reduce or diminish siRNA uptake and/or gene silencing in the RTF protocol.

Furthermore, while multi-well plates formed from a single material, such as treated polystyrene, may be used in the present invention, plates formed from two or more materials may also be used. Such multi-material well plates can be reviewed in U.S. Pat. Nos. 6,514,464, 5,457,527, RE 38,214 and 5,487,872, wherein each is incorporated herein by reference. Accordingly, the multi-material well plates can provide desirable structural characteristics, which include a well floor surface suitable for tissue culture and RNAi deposition, wherein the walls are not suitable. Also, the well floor can have optical characteristics that are suitable for certain downstream assays. For example, the plastic or glass beneath the well floor is transparent to visible and/or UV light, and the plastic surrounding the sidewalls of each well blocking light from passing between adjacent wells.

In one embodiment, the plate comprises a removable bottom. As such, the removable bottom can be favorable in transferring the well contents to a substrate. Also, plates with removable bottoms can be used in conjunction with any of the embodiments described herein. One example of an embodiment of a plate with a removable bottom is a plate with a removable film as the bottom. A removable film can be made of any suitable material, for example, a polyolefin. The removable film can be compatible with optical detection systems (i.e., can be transparent to one or more wavelengths of electromagnetic radiation, such as, for example, transparent to visual or UV light). In embodiments comprising a removable film, the contents of the well can be reduced in volume such that at least some of the contents of the well adhere to the film before the film is removed from the plate. Following removal from the plate, the film includes the contents of the plate adhered to locations on the film that correspond to locations of the wells. The film can then be used in any suitable detection methods. In one example, the film can be used to transfer the well contents to another substrate, such as, for example, nitrocellulose. Also, the cells in each well can be disrupted so as to expose their intracellular contents before the film is removed from the plate. Once transferred to a substrate, the substrate includes the contents of the wells and can be subjected to any suitable detection method. Some examples of detection methods include Western blotting, protein-protein blotting, ligand blotting, and nucleic acid hybridization. One method of adhering contents of a plate to a film is to evaporate the contents of the wells, or reduce the moisture contents of the wells.

In one embodiment, such a film can be made of a material that is selectively permeable, wherein the selective permeability is based on, for example, molecular size. In this embodiment, the film can be a molecular sieve. In one example, the film can comprise a molecular sieve that allows molecules smaller than about 10 kDa to traverse the membrane when positive pressure (e.g., from above the well) or negative pressure (e.g., from below the well) is applied. Where a film comprises a molecular sieve, well contents can be reduced in moisture by drawing permeable liquid through the sieve and leaving behind larger molecules that comprise the well contents.

In one example, a film comprising a sieve can be applied to the top of a plate. The plate can be inverted such that well contents contact the sieve. The bottom of the plate can be punctured or, if a film is present on the plate bottom, the film is removed. Positive pressure can be applied forcing the well contents against the molecular sieve. Alternatively, negative pressure can be applied from below the sieve. In this manner, moisture content of the wells is removed while transferring well contents to the surface of the sieve. The sieve will then contain well contents of the plate at the same relative positions as in the original plate. If desired the sieve can then be used to transfer the well contents, with known positions of well contents, to a suitable substrate such as, for example, nitrocellulose.

In one embodiment, a film can be employed in conjunction with a plate to confer certain optical characteristics. In these embodiments, at least a portion of the top and/or bottom of a plate can be applied to a film that is selectively opaque or selectively transparent to particular wavelengths of electromagnetic radiation. The films are used as film filters for one or more wavelengths or regions of electromagnetic radiation. For example, the film can be opaque to UV light, but transparent to visual light, or vice versa. The film can be placed over the top of the plate, or can be placed on the bottom of the plate. In embodiments where electromagnetic radiation reaches the sample from below, the film filter can be placed on the bottom of the plate. In embodiments where electromagnetic radiation reaches a well from above, the film filter can be placed on top of the plate. The film filter will typically contact the plate substrate. Two more films can be used together. The two or more films can be used by applying them to a plate adjacent to one another (e.g., apply a first film, then apply a second film on the first film).

Films used in any of the embodiments described herein can be made of any suitable material useful for the particular application. The films can be thin and flexible, or thin and rigid. The films can also be made compatible with robotic systems. Typically, films compatible with robotic systems will be relatively rigid so that they can be manipulated without disturbing the pattern or placement of well contents once the film is removed from the plate.

IV. Gene Silencing Plates

In one embodiment of the present invention, a well plate in accordance with the foregoing can be configured to be a gene silencing plate. Accordingly, the well plate can include a gene silencing composition in one or more wells. The gene silencing composition includes at least a first siRNA that targets at least a first gene for silencing. Also, the gene silencing composition can have a single siRNA directed against a family of related genes. Additionally, the well plate can have a well having multiple siRNAs targeting a single gene, or multiple siRNAs targeting multiple genes. The well plates can be gene silencing plates by having an siRNA-containing solution applied to at least one well, which is then dried in a manner that removes the solution and leaves a dried gene silencing composition.

In some instances the siRNA is solubilized in one of several of these types of solutions prior to applying, depositing, and/or spotting the siRNA solution onto the well floor, and drying the material on the plate. Usually, the siRNA is dissolved in distilled water that has been treated by one of any number of art-recognized techniques to eliminate contamination by RNases such as by ultrafiltration. Alternatively, the siRNA may be dissolved in one of several physiologically compatible, RNase-free buffers, including but not limited to phosphate buffer, Hanks BSS, Earl's BSS, or physiological saline. These solutions may contain one or more additional reagents that enhance the stability of the siRNA (e.g., RNase inhibitors) or alter the viscosity of the solution to enhance spotting or drying efficiency (e.g., sucrose) without changing the properties of the siRNA or injuring the cells that are added at subsequent stages in the RTF procedure.

In still other cases, the siRNA may be solubilized in a solution or medium that will enhance spotting, drying, or sticking to the plate of choice. Optionally, volatile solvents can be used that are compatible with siRNA. One example includes the use of alcohols, such as ethanol, which can be mixed with water in order to form a volatile solvent that can be readily dried and leave a dry gene silencing composition on the well floor. In some instances the solution of siRNA does not contain lipids that are easily oxidized over the course of time or can be toxic to cells. In other instances the siRNA is pre-complexed with a polynucleotide carrier in a solution before being deposited and dried to the well floor.

Accordingly, a predefined amount of siRNA can be administered to the well so that when it is dried and then resuspended, a known amount or concentration of control siRNA is available for gene silencing. The volume of siRNA solutions that are deposited on the bottom of each well can depend upon the concentration of the stock solution, functionality of the siRNA, and desired amount or concentration siRNA available for gene silencing. In general, the concentration of siRNA during transfection that is needed to silence a targeted gene effectively is dependent upon the functionality of the siRNA. For example, the concentration of siRNA during transfection can range from picomolar (e.g., 300-900 pM) for highly functional siRNA (e.g., silence>90% of target expression at 50-100 nM), to nanomolar (e.g., 100 nM) for siRNA of intermediate functionality (e.g., 70-90% silencing of target expression at 50-100 nM), and to micromolar (e.g., 1 uM) for low functionality. For example, for a 96-well plate, deposition of 5-50 uL of a 1 uM siRNA-containing solution is sufficient to generate an acceptable concentration of siRNA for RTF protocols. For smaller or larger sized wells, volumes and amounts of siRNA can be adjusted to compensate for the final concentration in each well In one embodiment, the total amount of siRNA in the gene silencing composition can be present in an amount for transfecting cells in only the well in which it is contained. As such, the total concentration of siRNA can be less than about 100 nM when solubilized or suspended in the aqueous medium during RTF. More preferably, the total concentration of siRNA can be less than about 50 nM when solubilized or suspended in the aqueous medium during RTF. Even more preferably the total concentration of siRNA can be less than about 25 nM when solubilized or suspended in the aqueous medium during RTF. In an additional preference, the total concentration of siRNA can be less than about 10 nM when solubilized or suspended in the aqueous medium during RTF. Most preferably, the total concentration of siRNA can be less than about 1 nM when solubilized or suspended in the aqueous medium during RTF. For example, the amount of siRNA in a 96-well plate can be from 0.1 picomoles ("pm") to about 100 pm, more preferably about 1 pm to about 75 pm, and most preferably about 10 pm to about 62.5 pm per well, where corresponding amounts of siRNA can be calculated for plates having other numbers of wells.

Additionally, the amount of siRNA added to each well can be sufficient for use in a single RTF protocol within that well. That is, the siRNA in the gene silencing composition can be present in an amount to only be used with the cells added to the well. As such, the amount of siRNA dried in the well can be insufficient for performing two RTF protocols in two different wells. This is because the amount of siRNA provided in the gene silencing composition is configured for a single RTF protocol in order to produce optimal results. Also, this eliminates the need to make a stock siRNA solution that is transferred into multiple wells, thereby reducing the complexity of the RTF protocol and increasing efficacy.

The siRNA-containing solutions can be deposited into wells using various well known techniques in the art for depositing liquids into wells of well plates, which can include manual and automated processes. Various methods can be used to dry the siRNA-containing solution into a gene silencing composition. In one embodiment, the plates are allowed to dry at room temperature in a sterile setting which allows the deposition solution to evaporate leaving behind the siRNA and any other conditioning compounds, such as salts, sugars, and the like. Dried plates are preferably vacuum-sealed or sealed in the presence of inert gases within a sterile container, and stored at temperatures ranging from −80° C. to 37° C. for extended periods of time without loss of silencing functionality. Thus, the plates having the substantially dry gene silencing compositions in at least one well can be stored at room temperature and shipped via traditional routes and still maintain the integrity and functionality of the siRNA.

In one embodiment, the well plate can have various other wells that can be used for control and calibration functions. As such, the well plate can have at least one well devoid or substantially devoid of siRNA. Also, the well plate can have at least one well that includes at least a first control siRNA, which can be a transfection control, positive control, or a negative control. For example, the control siRNA can include at least one of the following: (a) an siRNA that is capable of silencing a known gene; (b) transfection control siRNA; (c) an siRNA having a fluorescent marker; (d) siRNA having at least one toxic motif; (e) a non-functional siRNA; or (f) an siRNA that inhibits being taken in and processed by RISC.

V. siRNA

In one embodiment, the foregoing dry gene silencing compositions include at least a first siRNA which silences at least a first target gene. The gene silencing composition is configured such that the siRNA is capable of being solubilized or suspended in an aqueous medium in an amount sufficient for transfecting cells in the well. Optionally, the total amount of siRNA in the well is sufficient for implementing reverse transfection only for that well. Additionally, it is optional for the siRNA to have at least one of a hairpin structure with a loop, a modification or a conjugate. Also, the siRNA can be rationally designed to target the gene. Furthermore, the gene silencing composition can include a pool of siRNAs.

In one embodiment, the siRNA is selected to optimize functionality in silencing the target gene. Preferably, the siRNA has between 50% and 100% gene silencing functionality. More preferably the siRNA has a gene silencing functionality between 70% and 100%. Even more preferably, the siRNA has a gene silencing functionality between 80% and 100%. Most preferably, the siRNA has a gene silencing functionality between 90% and 100%. The design of functional genes can be based on providing modifications that increase on-targeting, decrease off-targeting, increase stability, are rationally designed for particular mRNA targets, and combinations thereof.

Additionally, the siRNA antisense strand can have varying levels of complementarity with the target sequence (e.g., mRNA). That is, the antisense strand is functional for inducing gene silencing of the target sequence. As such, the sense strand can be substantially homologous with the target sequence. Preferably, the antisense strand can have 50-100% complementarity with the target sequence. More preferably, the antisense strand can have 70-100% complementarity with the target sequence. Even more preferably, the antisense strand can have 80-100% complementarity with the target sequence. Still even more preferably, the antisense strand can have 90-100% complementarity with the target sequence. Most preferably, the antisense strand can have 100% complementarity with the target sequence.

Sequences having less than 100% complementarity can have bulges of one or more nucleotides, overhangs, or contain one or more mismatches. In addition, the siRNA can have overhangs of one to six nucleotides associated with the 3' and/or 5' end of the sense or antisense strands. Additionally, it should be recognized that overhangs are excluded from the calculation of complementarity, but can have homology or complementarity to the target sequence. Chemical modifications, bulges, or mismatches can direct the RNase-III Dicer to cleave the siRNA or shRNA at a particular position. A two nucleotide 3' overhangs can mimic natural siRNAs and are commonly used, but are not essential. Preferably, the overhangs can include two nucleotides, most preferably dTdT or UU. Also, the overhangs can include two nucleotides at the 3' end of the sense and/or antisense strand having complementarity or homology with the target sequence. The siRNA can have two nucleotide overhangs, wherein the hierarchy of C>U>G>A for the internal position and A>G>U>C for the terminal position are preferred. Additional information on siRNA structure and Dicer specificity can be found in Vermeulen A, et. al; The contributions of dsRNA structure to Dicer specificity and efficiency; *RNA* (2005), 11:674-682.

In one embodiment, it can be preferably to select siRNA from a list that have been identified from being rationally designed. As such, the siRNA can be selected from Table I of incorporated U.S. Provisional Application Ser. No. 60/678, 165. Table I is entitled "siGENOME Sequences for Human siRNA," and consists of columns "Gene Name," "Accession No.," "Sequence," and "SEQ. ID NO." Table I lists about 92,448 19-mer siRNA sense strand sequences, where antisense strand sequences were omitted for clarity. The siRNA sequences listed in Table I of the includes SEQ. ID NOs. 1 to about 92,448, wherein each preferably can also include a 3' UU overhang on the sense strand and/or on the antisense strand. Each of the about 92,448 sequences of Table I can also comprise a 5' phosphate on the antisense strand. Of the about 92,448 sequences listed in Table I of the incorporated provisional application, about 19,559 have an on-targeting set of modifications. A list of sequences, identified by SEQ. ID NO., that have on-target modifications is presented in Table II, entitled "List of Table I Sequences Having On-Target Modifications Identified by SEQ. ID NO." On-target modifications are on SEQ. ID NOs. 1-22,300. The siRNA in the gene silencing compositions may be used individually (e.g., one siRNA sequence per well) or as part of a pool.

In one embodiment, the siRNA can be configured as a short hairpin siRNA ("shRNA"). This because shRNA are a form of siRNA that includes a loop structure connecting the sense region with the antisense region to form a hairpin structure. Also, shRNA can have a substantially similar functionality compared to other types of siRNA. Additionally, an shRNA is not considered a modified siRNA unless the nucleotides include modifications as described in more detail below. In cases in which the siRNA is presented as a hairpin shRNA, the size and orientation of the strands can vary. Preferably, the shRNA present in the gene silencing composition have a sense strand or region and an antisense strand or region. The sense region and antisense region of the shRNA are part of a longer unimolecular structure that is organized in a stem of about 18-31 base pairs. The sense region and antisense region are connected via a loop structure that can be comprised of a polynucleotide or other linking group, as well as a combination thereof. Preferably the polynucleotide loop is comprised from between 4 and 10 nucleotides. More preferably, the stem is between 26 and 31 base pairs and the loop is derived from human miRNA hsa-mir-17 (sequence 5'→3': -AUAUGUG-, SEQ ID No: 1). The shRNA can also contain 3' and/or 5' overhangs similar to other types of siRNA. The overhangs, if present, can be dTdT, UU, or can have homology or complementarity to the target sequence.

The shRNA can include hairpins that are either right-handed or left-handed, as well as fractured hairpins. A right-handed shRNA is meant to refer to a unimolecular sequence that in its 5'→3' orientation has a sense region, a loop region, and then an antisense sense region. Similarly, a left-handed shRNA is meant to refer to a unimolecular sequence that in its 5'→3' orientation has an antisense region, a loop region, and then a sense region. Most preferably, the shRNA is: (1) organized in an antisense-loop-sense organization; (2) has a stem length of 26-31 nucleotides; and (3) has a loop that is derived from human miRNA hsa-mir-17. A description and further examples of siRNA having hairpin structures can be found in U.S. Provisional Patent Application No. 60/666,474, entitled "Hairpin Constructs," filed Mar. 29, 2005, and U.S Application 2004/0058886, which are incorporated herein by reference.

A. Chemical Modifications

In one embodiment, the siRNA in the gene silencing composition can be generated by one of several art-recognized means including chemical synthesis (e.g., 2'-ACE chemistry of U.S. Pat. No. 5,889,136, which is incorporated herein by reference), synthesis using enzymatic procedures (e.g., in vitro Dicer digestion of long dsRNA), or expression from plasmid or vector constructs. In the instance ACE chemistry is used to prepare siRNA, it is preferred that the solutions used to solubilize the siRNA have pHs that are compatible with the preservation of the 2'-ACE protecting group. Thus, it can be preferable for the solution to have a pH above 6.0, more preferably, between about 7.0 and about 8.0, and most preferably between about 7.5 and about 8.0. In the absence of ACE groups, but in the presence of the other chemical modifications, the pH can be between about pH 7.0 and about 7.3.

As briefly described, the siRNA in the gene silencing composition can be modified into increase specificity and/or stability. Accordingly, specificity modifications can be incorporated into any siRNA in order to decrease off-targeting. Such specificity modifications can be an aspect of on-targeting. Additionally, an siRNA can have both specificity and stability modifications. Further descriptions of modifications that enhance specificity include those described in PCT patent application number PCT/US04/10343, filed Apr. 1, 2004, PCT application with publication number WO 2005/097992, and U.S. Provisional patent application Ser. Nos. 60/542,668 and 60/543,661, the disclosures of which are incorporated by reference herein.

Examples of chemical modifications that can reduce off-target effects include various 2' modifications on the ribose groups of the siRNA, and can also include 5' phosphoryl modifications, which can include a phosphate group. Examples of such chemical modifications can include 2' modifications on the nucleotides at positions one and two of the sense strand, which are the first 5' sense nucleotide and the second 5' sense nucleotide of the duplex region, respectively. Additionally, the chemical modifications can include 2' modifications on the nucleotides at position one and/or position two of the antisense strand, which are the first 5' antisense nucleotide and/or the second 5' antisense nucleotide of the duplex region, respectively. The chemical modifications can also include a phosphoryl moiety, such as a phosphate group, on the 5' carbon at the 5' terminal nucleotide of the antisense strand. Also, the modification can replace a 5'-OH group with hydrogen to inhibit kinase phosphorylation.

An example of a specificity enhancing chemical modification can include 2' modifications at the first and second sense nucleotides and can include a phosphoryl moiety on the 5' carbon at the antisense 5' terminal nucleotide. A second example can include 2' modifications at the first and second sense nucleotides and at the first and second antisense nucleotides, and can include a phosphoryl moiety on the 5' carbon at the antisense 5' terminal nucleotide. A third example can include 2' modifications at the first and second sense nucleotides and at the second antisense nucleotide, and can include a phosphoryl moiety on the 5' carbon at the antisense 5' terminal nucleotide. A fourth example can include a 5' deoxy group modification on the sense 5' terminal nucleotide, and 2' modifications at the first and/or second antisense nucleotides with or without 2' modifications at the first and second sense nucleotides, as well as a phosphoryl moiety on the 5' carbon at the antisense 5' terminal nucleotide. Furthermore, including the modification of the phosphate group on the 5' carbon of the first antisense nucleotide in the absence of any 2' modifications can impart some benefit for reducing off-targeting. In some instances it can be preferable for the 5' carbon at the sense 5' terminal nucleotide to not have a phosphate group.

For example, on-target modifications can include 2'-O-methyl on nucleotide positions one and two (e.g., first position and second nucleotide at the 5' end) of the sense strand and a 5' phosphate on the antisense strand. Additionally, the on-target modifications can include a 2' modification on the nucleotide at position one and/or two of the antisense strand (i.e., the second nucleotide from the 5' end of the antisense strand), and a phosphate moiety at the 5' position of the 5' terminal nucleotide of the antisense strand. A preferred modification includes a 2' modification at the first and second sense nucleotides and at the second antisense nucleotide, and a phosphate on the antisense 5' terminal nucleotide.

In one embodiment, the present invention includes siRNA having stability enhancing modifications. As such, the stability modifications can be use in addition or alternatively to the specificity modifications. Additionally, siRNA having stability modifications can be advantageous because they can prevent degradation by nucleases. Accordingly, the stability modifications can increase the potential shelf life of siRNA, and increase the ability to manufacture and store plates having dry gene silencing compositions for extended periods of time. Furthermore, stability modifications can be used to induce target silencing for extended periods of time. Such stability modifications are described in U.S. Patent Application Ser. Nos. 60/542,646, 60/543,640, and 60/572,270, U.S Application Nos. 2004/0266707 and 2004/0198640, and International Publication Nos. WO 2005/097992, and WO 2004/090105 wherein each is incorporated herein by reference. Extended gene silencing in cells can be advantageous for several reasons. In some instances, the protein of the targeted gene can have a long half-life (e.g., greater than 24-48 hours), which can require extended gene silencing in order for the amount of the protein to be decreased.

In one embodiment, the present invention includes siRNA containing chemical modification patterns designed to enhance the stability of the sense strand, antisense strand, and/or the siRNA duplex. For example, the stabilized siRNA can contain 2' modifications on the first and second sense nucleotides, 2' modifications on at least one through all pyrimidine sense nucleotides, 2' modifications on the first and/or second antisense nucleotides, 2' modifications on at least one through all pyrimidine antisense nucleotides, and/or a 5' carbon having a phosphate modification at the sense or antisense 5' terminal nucleotide. The 2' modifications can be 2'-O-aliphatic modifications or 2'-halogen modifications. Stability modifications can also include internucleotide modifications with phosphorothioates or methylphosphonates.

In a first example, the stabilized siRNA can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, and a 5' carbon phosphoryl modification at the antisense 5' terminal nucleotide. A second example can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, a 5' carbon phosphoryl modification at the antisense 5' terminal nucleotide, and a cholesterol conjugate on the 5' carbon of the first sense nucleotide. A third example can include a 2'-O-aliphatic modification on the first sense and second sense nucleotides, a 2'-O-aliphatic modification on none or at least one through all of the sense pyrimidine nucleotides, a 2'-halogen modification on at least one through all of the antisense pyrimidine nucleotides, a 5' carbon phosphoryl modification at the antisense 5' terminal nucleotide, and a fluorescent tag conjugate on the 5' carbon of the first sense nucleotide, wherein the fluorescent tag can by any well known fluorescent group such as Cy3. A fourth example can include a 2'-O-aliphatic modification on the first sense and second sense nucleotides, a 2'-O-aliphatic modification on none or at least one through all of the sense pyrimidine nucleotides, a 2'-O-aliphatic modification on the first and/or second antisense nucleotides, a 2'-O-aliphatic modification on none or at least one through all of the antisense pyrimidine nucleotides, and a fluorescent tag conjugate on the 5' carbon of the first sense nucleotide. A fifth example can include a 2'-O-aliphatic modification on the first sense and second sense nucleotides, a 2'-O-aliphatic modification on none or at least one through all of the sense pyrimidine nucleotides, a 2'-O-aliphatic modification on the first and/or second antisense nucleotides, a 2'-halogen modification on none or at least one through all of the antisense pyrimidine nucleotides, and a 5' carbon phosphoryl modification at the antisense 5' terminal nucleotide. Additionally, any of the 2'-halogens can be replaced with a phosphorothioate group at the 2' or 3' atom. Also, any of the siRNA can include an overhang at the 3' end of the antisense strand. Optionally, the second antisense nucleotide can comprise a 2'-O-alkyl group such as 2'-O-methyl, and the first antisense nucleotide can comprise a 2'-OH or 2'-O-methyl. In another option, an overhang nucleotide can include a 2' modification.

In accordance with the foregoing, the 2' modifications can be 2'-O-aliphatic modifications. Also, the 2'-O-aliphatic modification can be present on any of the nucleotides of the sense strand and/or antisense strand. The aliphatic group can include a saturated or unsaturated, substituted or unsubstituted, and branched or unbranched chain having from 1 to 20 carbon or hetero atoms. More preferably, the aliphatic group has less than 10 carbon or hetero atoms, most preferably less than 5 carbon or hetero atoms, or is an alkyl group. In one option, the 2-O-aliphatic modification can be replaced with a 2'-O-aromatic substitution, or include an aromatic group. In another option, the aliphatic group can be cyclic. For example, the 2'-O-alkyl can be selected from the group consisting of 2'-O-methyl, 2'-O-ethyl, 2'-O-propyl, 2'-O-isopropyl, 2'-O-butyl, 2'-O-isobutyl, 2'-O-ethyl-O-methyl (i.e., —$CH_2CH_2OCH_3$), 2'-O-ethyl-OH (i.e., —$OCH_2CH_2OH$), 2'-orthoester, 2'-ACE group orthoester, and combinations thereof. Most preferably, the 2'-O-alkyl modification is a 2'-O-methyl moiety. Additionally, when the siRNA includes multiple nucleotides having modifications, there is no requirement that the modification be the same on each of the modified nucleotides. However, as a matter of practicality with respect to synthesizing the molecules of the present invention, it may be desirable to use the same modification throughout.

In one embodiment, it can be preferable for the 2' modification to be an orthoester. As such, the 2' modification can be a 2'-ACE group. The 2'-ACE group modifications can be reviewed in U.S. Pat. Nos. 6,590,093, 6,008,400, and 5,889,136, wherein each is incorporated herein by reference.

Additionally, the 2'-halogen modifications can be selected from the group consisting fluorine, chlorine, bromine, or iodine; however, fluorine is preferred. Similar to the specificity modifications, it may be desirable to use the same 2' modification throughout each respective strand. For example, 2'-O-methyl can be used on the sense strand, and 2'-F can be used on the antisense strand. However, different 2' modifications can be used on different nucleotides within the same strand.

B. Conjugates

In one embodiment of the present invention, the siRNA can include a conjugate coupled to the sense and/or antisense strands. The conjugate can perform a variety of functions or provide additional functionalities to the siRNA. For example, the conjugate can increase the penetration of the siRNA through a cell membrane with or without being complexed with a carrier. Additionally, the conjugates can be labels that can be monitored or identified in order to determine whether or not a labeled siRNA entered a cell.

For example, conjugates can include amino acids, peptides, polypeptides, proteins, antibodies, antigens, toxins, hormones, lipids, nucleotides, nucleosides, polynucleotides, sugars, steroids, carbohydrates, polysaccharides, polyalkylene glycols such as polyethylene glycol and polypropylene glycol, cholesterol, phospholipids, di-and tri-acylglycerols, fatty acids, aliphatics, enzyme substrates, biotin, digoxigenin, thioethers such as hexyl-S-tritylthiol, thiocholesterol, acyl chains such as dodecandiol or undecyl groups, di-hexadecyl-rac-glycerol, triethylammonium 1,2-di-O-hexadecyl-rac-glycero-3-H-phosphonate, polyamines such as polylysine and polyethylenimine, adamantane acetic acid, palmityl moieties, octadecylamine moieties, hexylaminocarbonyl-oxycholesterol, farnesyl, geranyl geranylgeranyl moieties, fluorescent label moieties such as rhodamines and fluoresciens, radioactive labels, enzymatic labels, and the like. Preferred conjugates include cholesterol and fluorescent labels.

Conjugates, such as cholesterol, polyethylene glycol, or polypeptides can facilitate delivery of the siRNA into a cell. Preferably, when the conjugate is a lipid, the lipid does not induce cellular toxicity when associated with the siRNA. Additionally, it is possible for a polypeptide or lipid conjugate, such as a fatty acid or cholesterol, to eliminate the need for forming a siRNA-carrier complex (e.g., lipoplex). In part, this is because the polypeptide or lipid can serve to transport the siRNA across the cell membrane.

For example, a cholesterol conjugate can be employed for improving of the potency of an siRNA as a silencing agent. This improvement can be obtained with modified and unmodified siRNA, as well as shRNA. Coupling cholesterol to the sense strand can alleviate negative effects due to 2' modifications to the sense strand. In some cases, cholesterol can enable passive delivery of the siRNA into the cell without using a polynucleotide carrier; however, polynucleotide carriers, such as lipids, can be used along with cholesterol conjugates. Accordingly, the siRNA-cholesterol can be delivered by forming a pore through which the siRNA can pass, or by being incorporated into the membrane and subsequently being delivered into the cell by an endocytosis pathways or membrane recycling.

Additionally, a label, such as a fluorescent conjugate, can be used in order to monitor the delivery of an siRNA into a cell. The fluorescent label can be used in order to photometrically monitor the delivery of the control siRNA into a cell. Preferably, the fluorescent label is a rhodamine or a fluorescien; however, other fluorescent molecules that can be coupled with an siRNA can be used. Specific examples of fluorescent labels include Cy3™, Cy5™ (Amersham), other cyanine derivatives, FITC, one of the ALEXA™ or BODIPY™ dyes (Molecular Probes, Eugene, Oreg.), a dabsyl moiety and the like. It is also possible to use fluorescent microparticles, such as inorganic fluorescent particles as long as the particle has a size that does not affect transfection efficiencies. The labels may be used to visualize the distribution of the labeled siRNA within a transfected cell. In addition, the label can be used to distinguish between transfected cells from non-transfected cells. As such, a population of cells can be transfected with the labeled siRNA and sorted by FACS. Moreover, the fluorescent labels can be particularly well suited for HCS and HTC analytical techniques. For example, cells that have been transfected can be identified, and then be further examined using HCS analysis.

The use of labeled nucleotides is well known to persons of ordinary skill, and labels other than fluorescent labels, such as enzymatic, mass, or radioactive labels, may be used in applications in which such types of labels would be advantageous. Further descriptions of labeled molecules that are applicable for siRNA reverse transfection are found in U.S. Provisional Patent Application Nos. 60/542,646, 60/543,640, and 60/572,270 and PCT Application Serial No. PCT/US04/10343, wherein each is incorporated herein by reference.

A conjugate can be attached directly to the siRNA or through a linker. The conjugate can be attached to any sense or antisense nucleotide within the siRNA, but it can be preferably for the coupling to be through the 3' terminal nucleotide and/or 5' terminal nucleotide. An internal conjugate may be attached directly or indirectly through a linker to a nucleotide at a 2' position of the ribose group, or to another suitable position. For example, the conjugate can be coupled to a 5-aminoallyl uridine. Preferably, the conjugate can be attached to the sense 3' terminal nucleotide, the antisense 3' terminal nucleotide, and the antisense 5' terminal nucleotide.

For example, linkers can comprise modified or unmodified nucleotides, nucleosides, polymers, sugars, carbohydrates, polyalkylenes such as polyethylene glycols and polypropylene glycols, polyalcohols, polypropylenes, mixtures of ethylene and propylene glycols, polyalkylamines, polyamines such as polylysine and spermidine, polyesters such as poly (ethyl acrylate), polyphosphodiesters, aliphatics, and alkylenes. An example of a conjugate and its linker is cholesterol-TEG-phosphoramidite, wherein the cholesterol is the conjugate and the tetraethylene glycol ("TEG") and phosphate serve as linkers.

Additionally, examples illustrating conjugates, uses of conjugates, and methods of making dsRNAs comprising a conjugate are disclosed in the following references: U.S. patent application Ser. No. 10/406,908, filed Apr. 2, 2003, published as U.S. Patent Application No. 2004/0198640; U.S. patent application Ser. No. 10/613,077, filed Jul. 1, 2003, published as U.S. Patent Application No. 2004/0266707 A1 on Dec. 30, 2004; and in PCT/US04/10343, international filing date Apr. 1, 2004, published as WO 2004/090105 A2 on Oct. 21, 2004, wherein each of the aforementioned applications is incorporated herein by reference. However, an siRNA comprising a conjugate can be synthesized by any suitable method known in the art.

VI. Reducing Off-Targeting

Off-targeting occurs when an siRNA designed to target and silence one gene unintentionally targets and silences one or more additional genes. Such off-targeting can occur due to varying levels of complementarity between the sense and/or antisense strand of the siRNA and the unintended target mRNA. The consequences that arise from off-targeting can include the silencing of critical genes, and can give rise to a variety of phenotypes (e.g., cell death, cell differentiation). Also, off-targeting can generate false positives in various phenotypic screens. As such, the consequences of off-targeting represent a challenging obstacle to the implementation of large scale, genome-wide siRNA-based phenotypic screens. Accordingly, it is advantageous to reduce and eliminate any off-target gene silencing.

In one embodiment, the consequences of off-targeting can be minimized or inhibited by using pools of siRNAs. Pools of siRNAs have been shown to generate fewer off-target effects as compared to single siRNA. As noted above, the pools may comprise two or more siRNAs that are substantially complementary to different subsequences of one target mRNA or they may be substantially complementary to subsequences of different target mRNAs. For example, a first siRNA and a second siRNA can contain antisense sequences that are substantially complementary to first and second subsequences of one target mRNA. The first and second subsequences can be mutually exclusive or overlapping. The gene silencing composition can include pools that have two, three, four, five, or more different siRNAs. The benefit of reducing off-target effects due to pools of siRNAs is particularly noticeable when at least two siRNA are directed against the same target. Also, pools of modified siRNA, pools of siRNA having hairpin structures, or pools of siRNA having conjugates can be advantagous. The benefits of using pools of siRNA are described in U.S. patent application Ser. No. 10/714,333, filed Nov. 14, 2003, related PCT application PCT/US03/36787, published on Jun. 3, 2004 as WO 2004/045543 A2, U.S. patent application Ser. No. 10/940,892 filed Sep. 14, 2004, published as U.S. Patent Application Publication 2005/0255487 and U.S. Patent Application Publication 2005/0246794 wherein each is incorporated herein by reference.

The reduction of off-targeting or increased specificity can also be achieved by using siRNA concentrations that are below the level that induces off-target effects. As an example, transfection of a single siRNA at 100 nM can induce 90% silencing, yet the high concentration of the siRNA may also induce off-target effects. In contrast, a pool of four siRNAs (e.g., total concentration of 100 nM, 25 nM each) can similarly induce 90% silencing. Since each siRNA is at a four-fold lower concentration, the total number of off-targets is fewer. Thus, in order to obtain silencing with inhibited or no off-target effects, a highly functional siRNA can be used at low concentrations, or pools of siRNA targeting the same gene can be used with each siRNA of the pool having a concentration that is sufficiently low to minimize off-target effects. Preferably, the total amount of siRNAs can be delivered at concentrations that are less than or equal to 100 nM. More preferably, the total amount of siRNAs can be delivered at concentrations that are less than or equal to 50 nM. Even more preferably, the total amount of siRNAs can be delivered at concentrations that are less than or equal to 25 nM. Even more preferably, the total amount of siRNAs can be delivered at concentrations that are less than or equal to 10 nM. Most preferably, the total amount of siRNAs are delivered at concentrations that are less than or equal to 1 nM.

In another embodiment, another way to inhibit or stop off-target effects is to introduce thermodynamic instability into the duplex base pairing at the second antisense nucleotide. For example, this can be achieved through a mismatch between that siRNA antisense nucleotide and the nucleotide located where the complement should be in the target mRNA. Alternatively, an insertion or deletion of a nucleotide in the siRNA antisense strand or sense strand can generate a bulge in the duplex that forms between the siRNA antisense strand or sense strand and the target mRNA or off-targeted sequence. Additionally, thermodynamic instability can also be introduced at the third, fourth, fifth, sixth, and/or seventh antisense nucleotides from the 5' end. However, the resulting thermodynamic instability can lead to silencing of other sequences (i.e., other or secondary off-target effects), but can be avoided by using rationally designed thermodynamic instabilities.

VII. Polynucleotide Carriers

In one embodiment, the present invention includes polynucleotide carriers that can interact with an siRNA, and transport the siRNA across a cell membrane. However, in other embodiments of the invention modes of transfection can be implemented without carriers, such as by electrophoresis, precipitation, particle bombardment, optoporation, and microinjection. Usually, polynucleotide carriers include a positive charge that interacts with the negatively charged phosphates on the polynucleotide backbone. Polynucleotide carriers are well known in the art of cellular nucleic acid delivery. Preferred polynucleotide carriers include polymers, lipids, lipopolymers, lipid-peptide mixtures, and the like that are capable of complexing with an siRNA and delivering the siRNA into a cell in a manner that retains the gene silencing functionality without being overly toxic. As such, routine experimentation can be implemented with procedures described herein with respect to optimizing RTF in order to identify the optimal polynucleotide carrier for a certain system or cell.

In one embodiment, lipids or lipid-peptide mixtures are preferable for introducing siRNA into a target cell. Typically, the lipid is a cationic lipid. Cationic lipids that can be used to introduce siRNA into cells can be characterized by having little or no toxicity (e.g., defined as less than 15-20% toxicity), which can be measured by AlamarBlue or equivalent cell viability assays. Additionally, the lipids can deliver sufficient amounts of siRNA into cells in order to induce gene silencing. Lipids are available from a variety of commercial resources including but not limited to Invitrogen (LIPO-FECTAMINE™, LIPOFECTAMINE™ 2000), Ambion (si-PORT™), B-Bridge International (siFECTOR™), Mirus (TransIT-TKO™), and Qiagen (RNAiFECT™). However, not all lipids are functionally equivalent and certain lipids can perform better with specific cell lines. Thus, the foregoing optimization procedures can be employed to determine an appropriate lipid and lipid concentration for delivering siRNA for a specific cell line. Also, lipid-peptide mixtures can provide enhanced delivery of the siRNA into cells. Peptides that have affinity to one or more proteins, lipids, lipid-polysaccharide, or other components of the cell membrane can be conjugated to the siRNA and used independent of lipids or advantageously combined with one or more lipids to form a polynucleotide carrier. Such lipid-peptide mixtures can enhance RTF of siRNA. Cholesterol conjugates can be similarly coupled to the siRNA and be used independent of polynucleotide carriers or advantageously combined therewith.

Briefly, in order to identify whether a given lipid is acceptable for siRNA RTF, two or more well characterized siRNAs can be tested under a variety of lipid, media, and siRNA concentrations using the optimizing RTF methods described herein. Subsequently, the level of silencing of the targeted gene and the level of cell death are quantified using art-accepted techniques. Suitable lipids for siRNA RTF include but are not limited to OLIGOFECTAMINE™, TransIT-TKO™, or TBIO Lipid 6™ (Transgenomic part # 24-1001-05). More preferably, the invention uses LIPO-FECTAMINE™ 2000 (Invitrogen). And most preferably, the invention uses lipids DharmaFECT™ 1, DharmaFECT™ 2, DharmaFECT™ 3, DharmaFECT™ 4 (Dharmacon, Inc.) that have been specifically designed for the delivery of siRNA. The term "DharmaFECT™" (followed by any of the numerals 1, 2, 3, or 4) or the phrase "DharmaFECT™ transfection reagent," refers to one or more lipid-based transfection reagents that have been optimized to transfect siRNA rather than larger nucleic acids (e.g., plasmids).

The formation of a functional siRNA-lipid complex can be prepared by combining siRNA and the lipid. As such, an appropriate volume of lipid at a selected concentration can be combined with a volume of media and/or buffer to form a lipid-media or lipid-buffer having a suitable concentration of lipid. For example, a volume of lipid media ranging from about 5-50 microliter ("uL") can include about 0.03-2 micrograms ("ug") of lipid to be introduced into each well of a 96-well plate, and the amount of lipid can be changed to correspond with other well sizes. The choice of media and/or buffer for siRNA RTF can improve the efficiency of the RTF protocol. Some media contain one or more additives that induce cell toxicity and/or non-specific gene modulation during RTF. Examples of preferred media or buffers include Opti-MEM™ (GIBCO, Cat. # 31985-070), HyQ-MEM-RS™ (HyClone, Cat. # SH30564.01), Hanks Balanced Salt Solution™, or equivalent media. A suitable media can be identified by employing the optimization protocol described herein.

The lipid-media or lipid-buffer can be introduced into a well by a variety of methods including hand-held single and multi-channel pipettes, or more advanced and automated delivery systems that can inject measured volumes of the lipid solution into a well. The lipid solution can be incubated in the well that contains the dried gene silencing composition for a period of time that is sufficient to solubilize or suspend the siRNA, and to form siRNA-lipid complexes (e.g., lipoplexes). In general, the process of siRNA solubilization and lipoplex formation can require about 20 minutes, but usually not more than 120 minutes. The complex formation process is generally performed at room temperature, but can be performed at temperatures ranging from 4-37° C. In some instances, the lipid and siRNA can be mixed by agitating the plate (e.g., swirl, vortex, sonicate) for brief periods (e.g., seconds-minutes) to enhance the rate of siRNA solubilization and complex formation.

VIII. Well Arrangements

In one embodiment, the siRNA RTF plates that include multiple wells having different dry gene silencing compositions can have the wells organized into predefined arrangements. Such arrangements can correspond to the type of assay being employed with the siRNA RTF plate. That is, when a family of genes are being studied, the siRNA that target the same gene can be organized in one column or row while the siRNA targeting a different gene can be organized in a different column or row. Thus, the wells can be organized into a pre-selected arrangement so that particular siRNAs are in a pre-selected pattern on a plate. The pre-selected pattern can include control wells, such as those that include one or more negative and/or positive siRNA controls, and transfection controls. Also, the pre-selected pattern can include wells that are empty or substantially devoid of siRNA, which can be used as controls and for calibrations.

It can be beneficial to have siRNA that is pre-dried in the wells of different well plates so that multiple plates can be prepared simultaneously. This can allow for well plates to have gene silencing compositions at standardized positions and amounts of siRNA, which is beneficial for using standardized well plates in multiple experiments that can be conducted over time without introducing variability between the plates. The use of standardized plate arrangements can provide a series of plates that can be used over time and provide data that can be analyzed together.

For example, a plate comprising a plurality of columns of wells can include a transfection control in the first column, positive controls for RNAi in the second column, negative controls for RNAi in a third column, a pool of siRNAs directed against a single target in a fourth column, and individual members of the siRNA pool that comprise the fourth column are in subsequent columns, such as the fifth through twelfth columns. Alternatively, the fifth through twelfth columns can comprise different concentrations of each siRNA in the pool of the fourth column, with the amount of siRNA increasing from well to well or decreasing from well to well. Each well can include one concentration of each siRNA in the pool, or two, three, four, five, or more concentrations of each siRNA in the pool can be in different wells. The number of concentrations of siRNA that can be used is limited only by the number of wells on the plate; however, multiple plates can be configured to be used together with a predefined pattern that spreads across all the plates.

Accordingly, the pre-selected patterns of siRNA concentration gradients can be used as a pattern that can be observed so that the optimal amount of each siRNA in a pool can be determined by observing the level of silencing by a particular siRNA at a number of concentrations of that particular siRNA. For example, sequential rows in the fourth column can have sequentially increasing or decreasing amounts of total pool siRNA. Additionally, sequential columns can include sequentially increasing or decreasing amounts of individual siRNA of the pool.

Figure 1A:
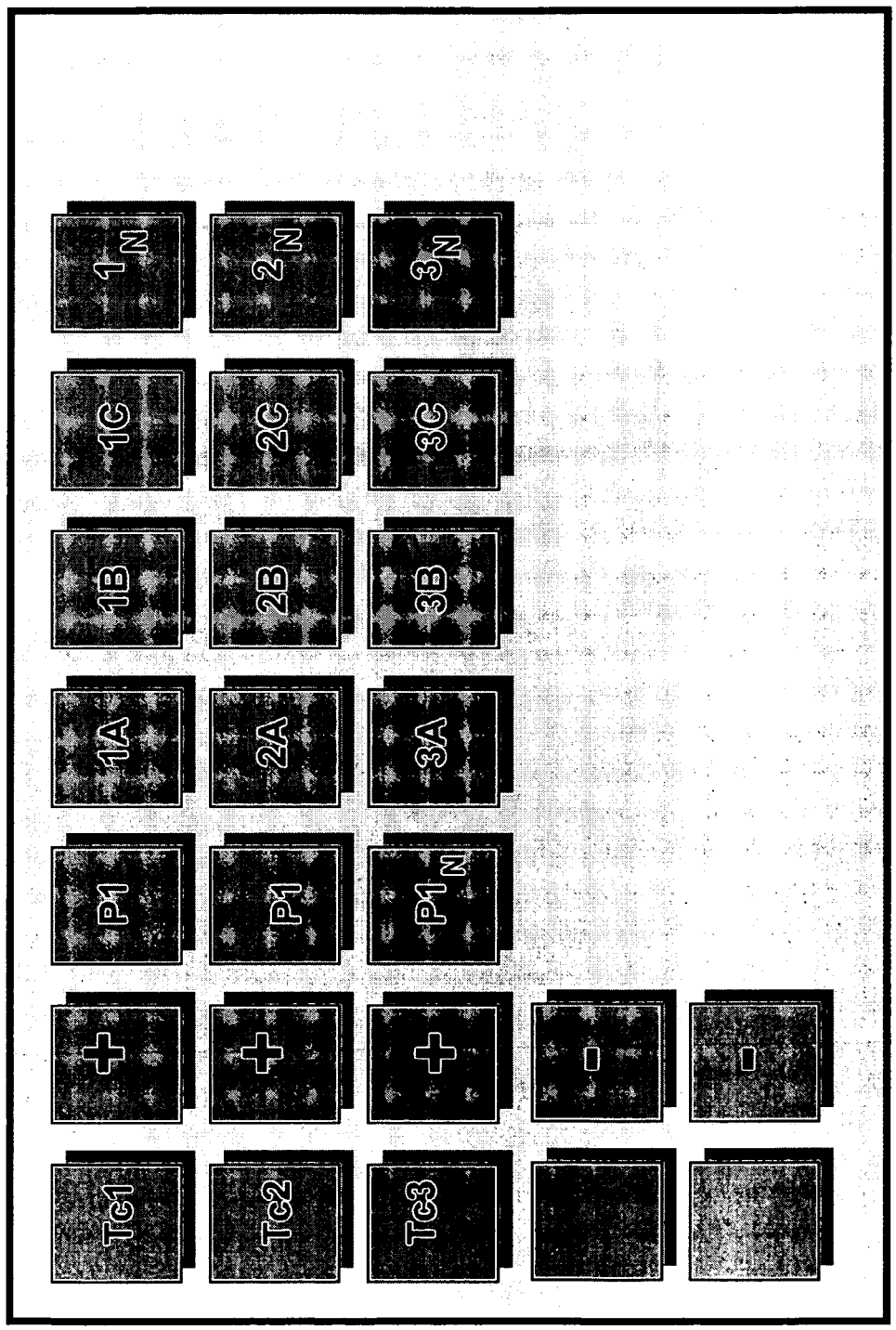
FIG. 1A is a schematic diagram that illustrates an embodiment of an arrangement of siRNA on a multi-well plate, wherein a pool of siRNA ("P1") is positioned with individual siRNA that comprise the pool (e.g., $1A-1_N$, $2A-2_N$, $3A-3_N$).
Figure 1B:
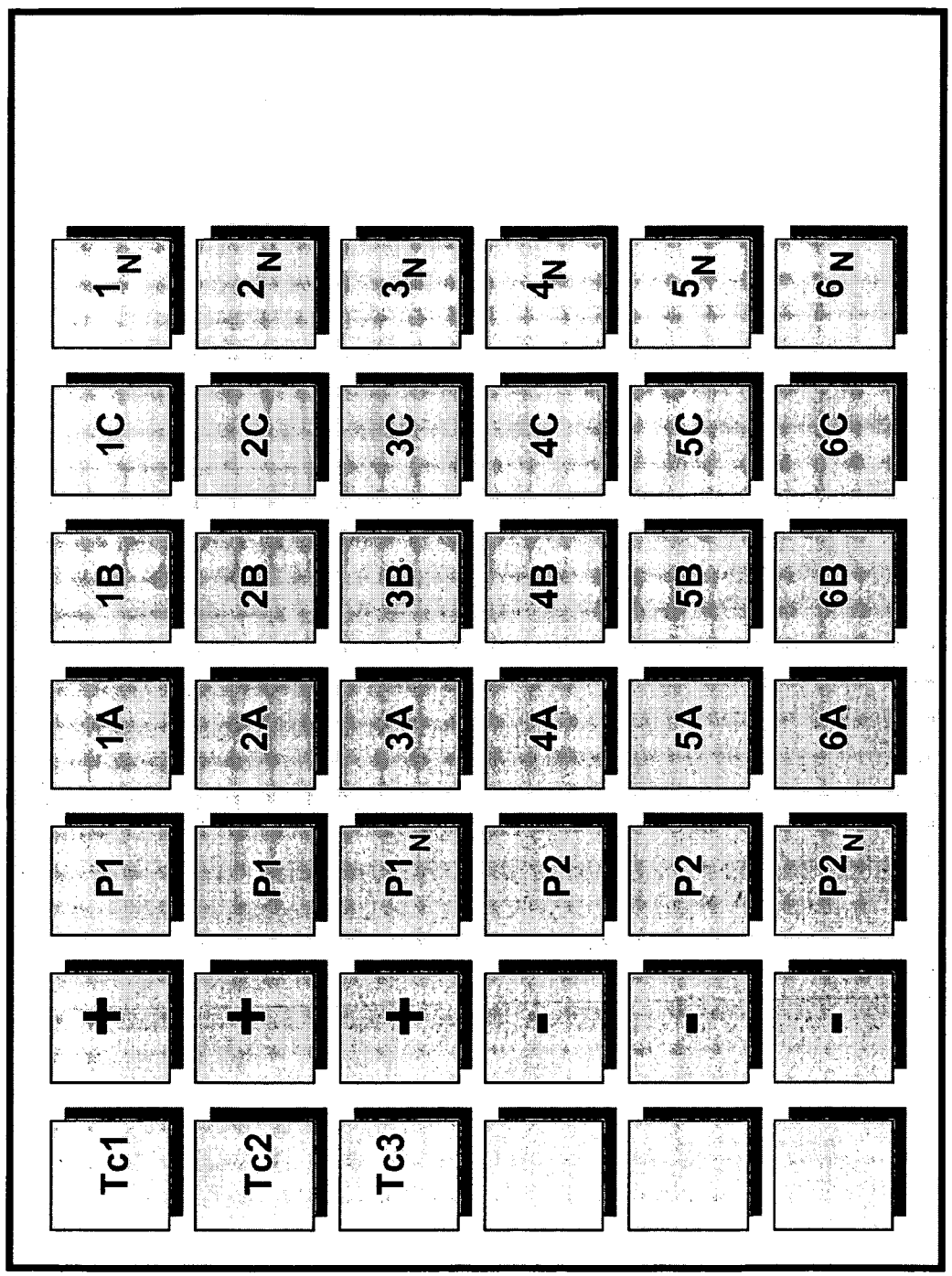
FIG. 1B is a schematic diagram that illustrates an embodiment of an arrangement of siRNA on a multi-well plate, wherein more than one pool (P1 and P2) are positioned with individual siRNA that comprise the pools (e.g., $1A-1_N$, $2A-2_N$, etc.), and controls (e.g., Tc1, Tc2, and Tc3).
Figure 2C:
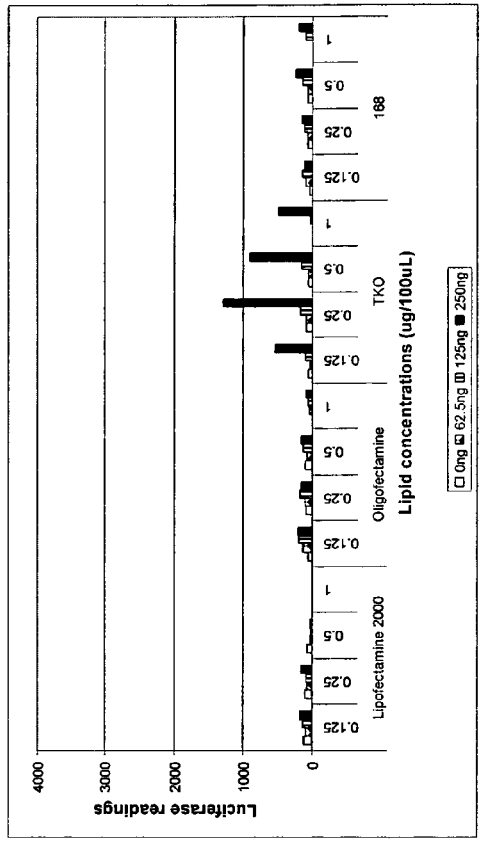
FIGS. 2A-2F are graphical representations of embodiments of a comparison of RTF of DNA and RNA by cell viability and gene silencing efficacy.
Figure 2D:
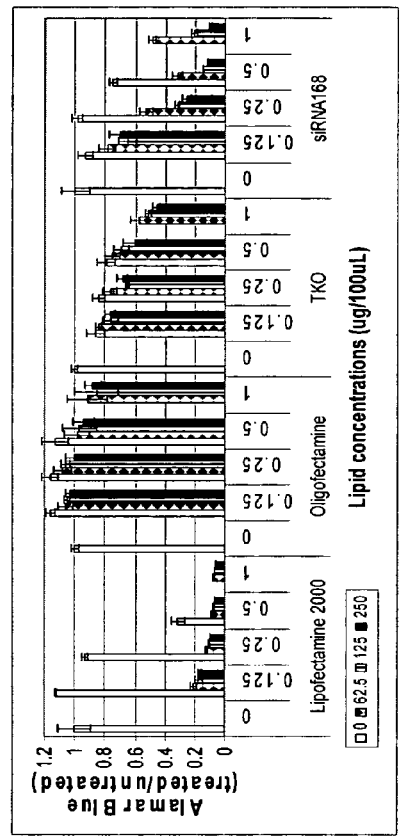
Figure 2A:
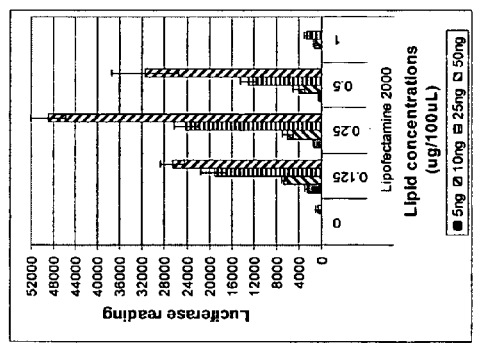
Figure 2B:
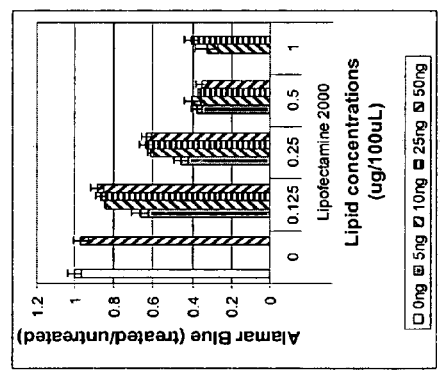
Figure 2E:
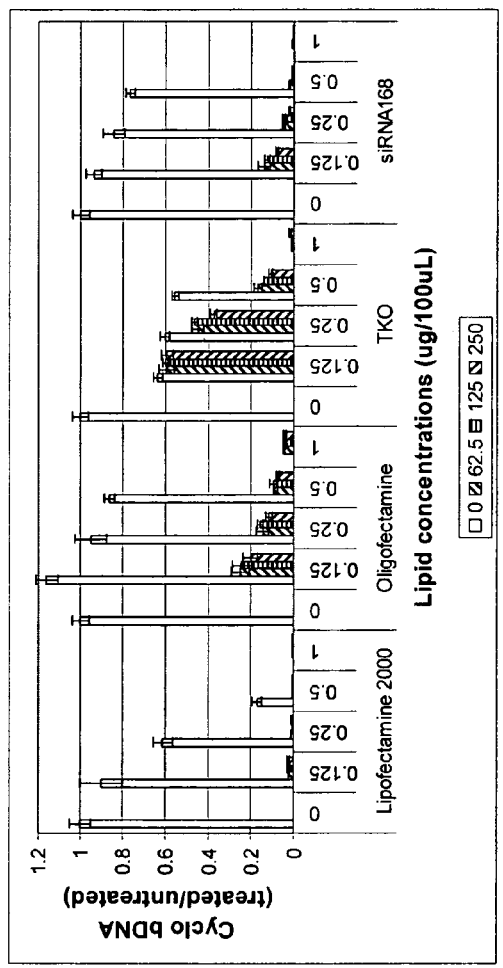
Figure 2F:
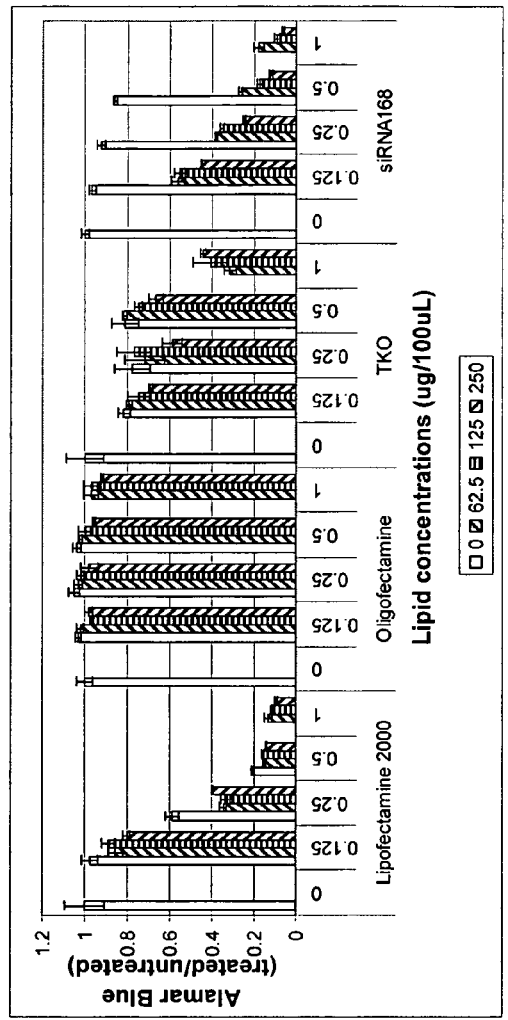
Figure 3A:
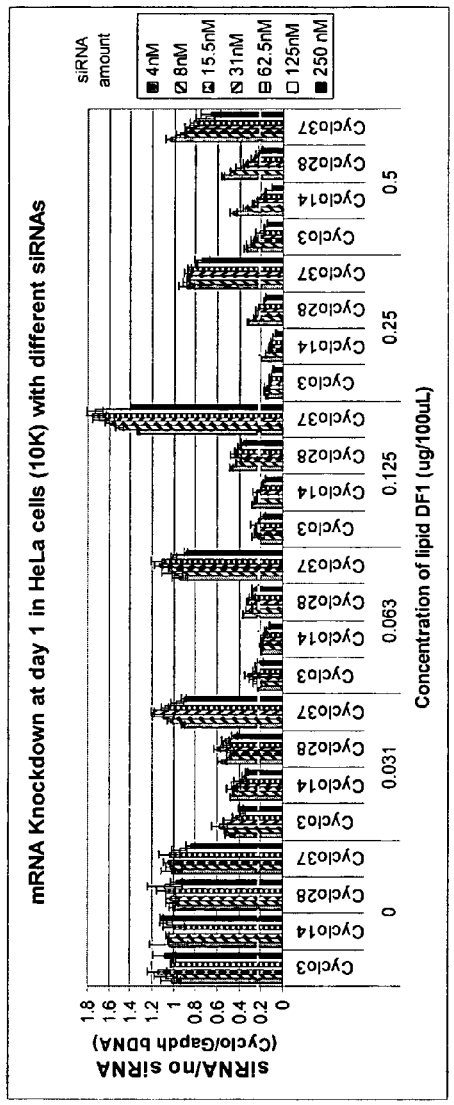
FIGS. 3A-3F are graphical representations of an embodiment of the effects of siRNA functionality in siRNA RTF. Four different siRNA (e.g., cyclo 3, 14, 28, and 37) having different silencing functionalities (e.g, 95, 90, 75, and <50% silencing, respectively) were plated for RTF at varying concentrations. Varying amounts of DharmaFECT™ 1 lipid were added such that 0-0.5 microgram ("ug") of lipid were delivered per 100 microliter ("uL"). Following the solubilization and complexing of the siRNA, HeLa cells at 10,000 cells per well were added and cultured (e.g., 1, 2, or 4 days). The effects of siRNA functionality in the RTF format were evaluated by assaying cyclophilin B silencing in FIGS. 3A, 3C, and 3E, and cell viability in FIGS. 3B, 3D, and 3F. For cell survival measurements, the Y-axis represents relative levels of survival with 1.0 being 100% viability. For gene silencing, the Y-axis represents the level of gene expression compared to controls with 1.0 being 100% expression.
Figure 3B:
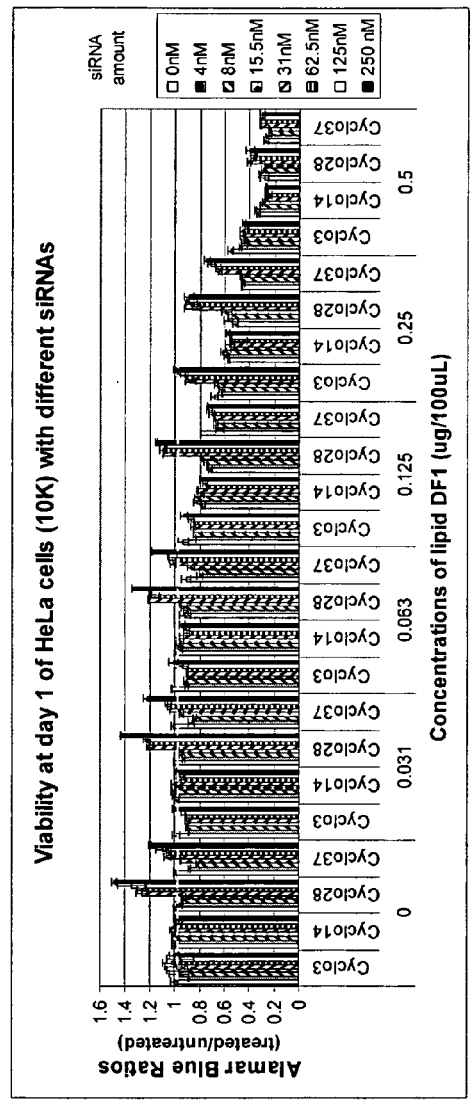
Figure 3C:
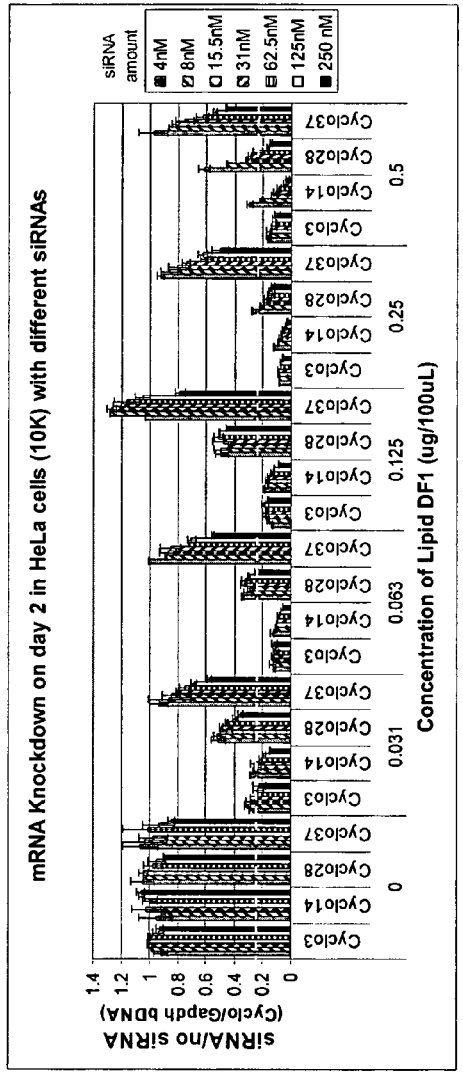
Figure 3D:
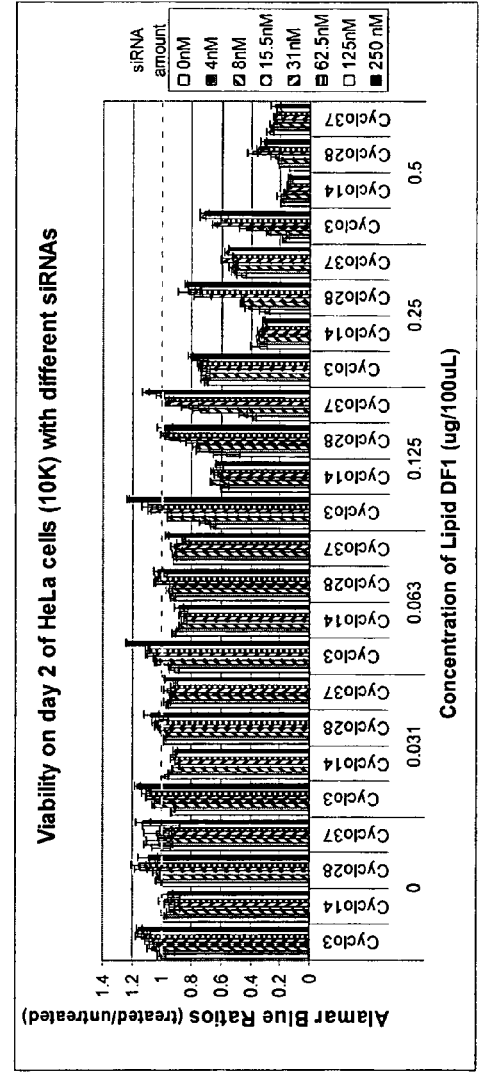
Figure 3E:
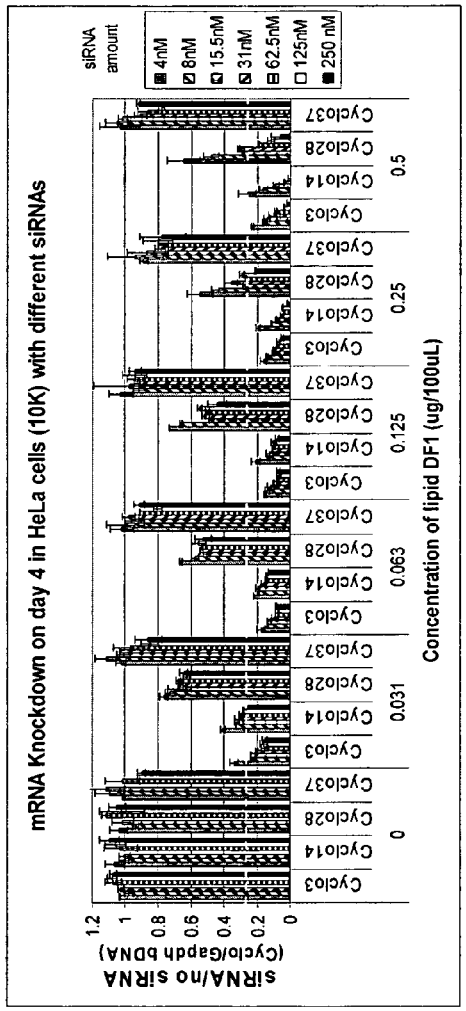
Figure 3F:
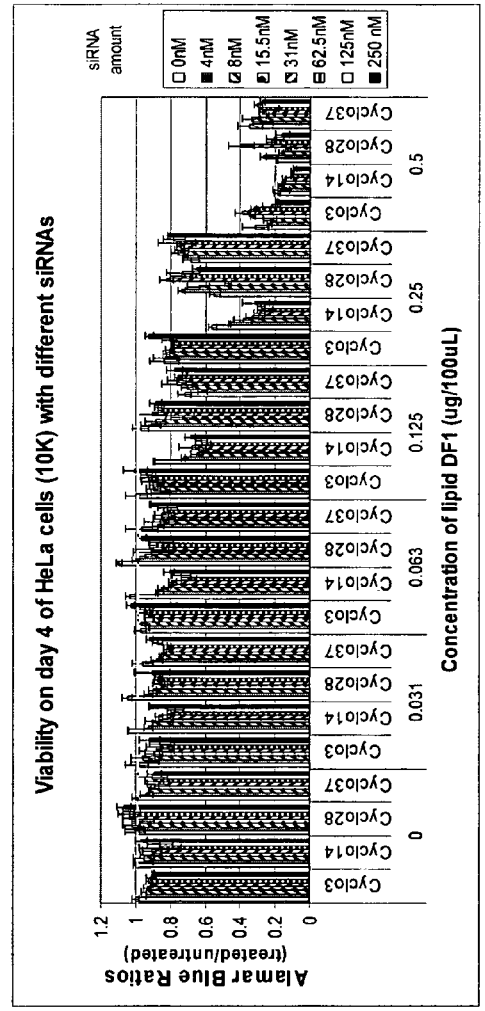

FIGS. 1A and 1B illustrate embodiments of plate arrangements similar with the foregoing concentrations arrangements. While the wells are shown to be square, it should be recognized that they can be any shape. Also, the well plate can include any number of wells, and the number of wells depicted is merely for example. In the figures the wells are defined as follows: "Tc" indicates a transfection control well, wherein the increasing corresponding numbers identify different transfection controls; blank wells indicate wells devoid or substantially devoid of any siRNA; "+" indicates a positive control; "−" indicates negative controls; "P1" through "P1$_N$" indicate a first pool which silences a first gene at a concentration gradient; "P2" through "P2$_N$" indicate a second pool which silences a second gene at a concentration gradient; "1A" through "1$_N$" indicate a first individual siRNA of the first pool at a concentration gradient; "2A" through "2$_N$" indicate a second individual siRNA of the first pool at a concentration gradient; "3A" through "3$_N$" indicate a third individual siRNA of the first pool at a concentration gradient; "4A" through "4$_N$" indicate a first individual siRNA of the second pool at a concentration gradient; "5A" through "5$_N$" indicate a second individual siRNA of the second pool at a concentration gradient; and "6A" through "6$_N$" indicate a third individual siRNA of the second pool at a concentration gradient. Thus, FIG. 1A illustrates a well plate assaying a single pool, and FIG. 1B illustrates a well plate assaying multiple pools. Additionally, a well plate can include more than two pools. Also, the pools and single siRNA can be rationally designed, and/or have modifications or conjugates.

Additionally, embodiments of plate arraignments can be organized such that the plate comprises siRNA directed against a single biologically relevant pathway, a cellular process, cellular event, regulatory proteins, embryonic processes, specific loci in a chromosome, the cell cycle, development of an organism or organ, differentiation of a cell, an inflammatory process, a proliferative process, angiogenesis, and the like. In another embodiment, a plate can be arraigned with siRNAs targeting genes that are known and/or suspected to be implicated in a disease or disorder, or biological process preceding a disease or disorder. In another embodiment, a well plate can include siRNA that function as miRNA inhibitors. In another embodiment, the principle of a plate arrangement for studying a biological pathway with siRNA associated with known or suspected upstream and downstream effects can be applied to proteins that are not kinases. Additional descriptions of these and other plate arrangements for various studies can be reviewed in the incorporated U.S. Provisional Application Ser. No. 60/678,165.

In another embodiment, a well plate can be arranged with siRNA that target genes that have one or more single nucleotide polymorphisms ("SNP"). Such well plates can be prepared in order to assess the contribution of a particular SNP to a phenotype, a biological function, disease state, or other event. For example, an SNP plate may comprise wells that have different siRNA(s), including the following: (i) a first siRNA directed against a first target; (ii) and second siRNA that differs by one base pair from the first siRNA, which includes a SNP; (iii) an siRNA pool comprised of the first siRNA and the second siRNA; and (iv) control siRNA. Also, the first target and the second target can code for potentially lethal pairs.

In yet another embodiment, a well plate can contain an arrangement of siRNA that are directed against a gene or genes whose knockdown is known to induce a particular disease state. Such wells can be organized so as to facilitate study of that particular disease with sequential siRNA targeting such genes. In this way, researchers can study a variety of disease states including those associated with cancer, neurological diseases, diabetes, metabolic diseases, diseases of the bone, cartilage, muscle, heart, kidneys, liver, prostate, gastrointestinal tract, and more. The wells of these plates may comprise individual or pools of siRNA.

Additionally, a well plate can be arraigned to include a number of different siRNAs that are modified and/or unmodified in different wells. For example, a 96-well plate may contain the following: 10-12 wells of a first siRNA that is unmodified; 10-12 wells of the first siRNA that is modified; 10-12 wells of a second siRNA that is unmodified; 10-12 wells of the second siRNA that is modified; 10-12 wells of a third siRNA that is unmodified; 10-12 wells of the third siRNA that is modified; 10-12 wells of a fourth siRNA that is unmodified; and 10-12 wells of the fourth siRNA that is modified. The first, second, third and fourth siRNAs may be directed to different regions of the same target mRNA such that may or may not overlap, or they may be directed to different mRNA that code for unrelated proteins, or proteins that have similar functions or act in the same biological pathway.

In another embodiment, a well plate can be arranged so that some of the wells comprise pools, and some of the wells comprise single types of siRNA. Thus, the well plate may have different wells that comprise the following: (i) a first siRNA, a second siRNA, a third siRNA, a fourth siRNA, and a fifth siRNA, any of which may be modified or unmodified; (ii) the first siRNA, the second siRNA, the third siRNA, and the fourth siRNA, any of which may be modified or unmodified; (iii) the first siRNA, the second siRNA, the third siRNA, and the fifth siRNA, any of which may be modified or unmodified; (iv) the first siRNA, the second siRNA, the fourth siRNA, and the fifth siRNA, any of which may be modified or unmodified; (v) the first siRNA, the third siRNA, the fourth siRNA, and the fifth siRNA, any of which may be modified or unmodified; (vi) the second siRNA, the third siRNA, the fourth siRNA, and the fifth siRNA, any of which may be modified or unmodified; (vii) the fifth siRNA, which may be modified or unmodified; (vii) a sixth siRNA, which may be modified or unmodified; (viii) a seventh siRNA, which may be modified or unmodified; (ix) an eighth siRNA, which may be modified or unmodified; (x) a ninth siRNA, which may be modified or unmodified; and/or (xi) a control siRNA.

Additionally, the well plate arrangements can be organized in order to study libraries of siRNAs, which can be provided in an array format. Preferably, the array comprises an RTF siRNA library. An RTF siRNA library can be used to study entire gene families or regulatory pathways. These siRNA libraries contain pre-selected groups of rationally designed pools of siRNA reagents targeting genes confirmed to be relevant to a particular pathway or to be phylogenetically related to the indicated gene family. Additionally, examples of such siRNA libraries can be reviewed in Table 1.

TABLE 1

SIRNA LIBRARIES

| Plate(s)/Pathway | Number of Genes |
| --- | --- |
| Human Genome | ~22,000 |
| Human Druggable Set | 7309 |
| Protein Kinases | 779 |
| Tyrosine Kinases | 85 |
| Calcium/Calmodulin Protein Kinase (CaMK) | 71 |
| CMGC Kinases | 60 |
| AGC Kinases | 59 |
| Mitogen-Activated Protein Kinase (MAPK) | 58 |
| S-T Kinases | 54 |
| Proteases | 514 |
| Serine Proteases | 128 |
| Metallo Proteases | 128 |
| Cysteine Proteases | 74 |
| G-Protein Coupled Receptors | 518 |
| Apoptosis | 318 |
| Ion Channels | 286 |

TABLE 1-continued

SIRNA LIBRARIES

| Plate(s)/Pathway | Number of Genes |
| --- | --- |
| Phosphatases | 193 |
| Cytokine Receptors | 166 |
| Membrane Trafficking/Remodeling | 122 |
| Cell Cycle Regulation | 111 |
| Deubiquinating Enzyme | 106 |
| Undifferentiated Cancer | 69 |
| Neoplastic Tissue | 67 |
| Nuclear Receptor | 49 |
| Insulin Signaling Pathway | 31 |
| Protein Hydroxylase | 24 |

Descriptions of siRNAs comprising the siRNA libraries in Table 1, more complete descriptions of the use of gene silencing to study the pathways identified in Table 1, and additional descriptions of plate arrangements and the types of genes that can be studied using pools of siRNA are provided in U.S. Provisional Application Ser. No. 60/678,165.

EXAMPLES

The following examples are provided to describe some embodiments of the present invention in a manner that can be use by one of skill in the art to practice the present invention. Additionally, the following examples include experiments that were actually performed as well as prophetic experiments. Additional examples and supplementary information for the following examples can be reviewed in the incorporated references having Ser. No. 11/283,482, entitled APPARATUS AND SYSTEM HAVING DRY GENE SILENCING POOLS, with Barbara Robertson, Ph.D., et al. as inventors, Ser. No. 11/283,482, entitled APPARATUS AND SYSTEM HAVING DRY CONTROL GENE SILENCING COMPOSITIONS, with Barbara Robertson, Ph.D., et al. as inventors, and U.S. Provisional Application Ser. No. 60/678,165. The polynucleotide sequences that were used in the examples can be found in Tables I-IV of U.S. Provisional Application Ser. No. 60/678,165.

Example 1

The polynucleotides of the present invention can be synthesized by any method that is now known or developed in the future that can be used to prepare polynucleotides that form siRNA. A single strand of an siRNA duplex that includes a modification, as described herein, may be chemically synthesized using compositions of matter and methods described in Scaringe, S. A. (2000) Advanced 5'-silyl-2'-orthoester Approach to RNA Oligonucleotide Synthesis, *Methods Enzymol.*, 317, 3-18; Scaringe, S. A. (2001) RNA Oligonucleotide Synthesis via 5'-silyl-2'-orthoester Chemistry, *Methods*, 23, 206-217; U.S. Pat. Nos. 5,889,136; 6,008,400; 6,111,086; and 6,590,093; each of which is incorporated herein by reference. Briefly, the synthesis methods can utilize nucleoside base-protected 5'-O-silyl-2'-O-orthoester-3'-O-phosphoramidites or other blocking groups in order to incorporate modified or unmodified nucleotides into a polynucleotide having a specific siRNA sequence. The synthesis is typically performed so that the polynucleotides extend from a solid support in the 3' to 5' direction.

Example 2

The sense strand and antisense strand of an siRNA duplex are chemically synthesized in separate reaction procedures, as described in Example 1. Briefly, each synthesis procedure is similar and initiates with nucleotides being sequentially extended from a solid polystyrene support to which a 3'-most nucleoside has been covalently tethered, wherein the sense nucleoside $X_{21}$ and antisense nucleoside $Y_{21}$ are tethered to the support. The nucleosides are then added sequentially in a sequence-specific manner, which is from the 3' to 5' direction, to the support-bound species using repetitive cycles. The reaction cycles are performed as follows: the first cycle adds the sense nucleoside $X_{20}$ to $X_{21}$ or antisense nucleoside $Y_{20}$ to $Y_{21}$; the second cycle adds sense nucleoside $X_{19}$ to $X_{20}X_{21}$ or antisense nucleoside $Y_{19}$ to $Y_{20}Y_{21}$; and continues until the complete sense or antisense strand is complete. Each cycle consists of four steps: deprotection of the 5'-hydroxyl group of the support-bound species; coupling of a reactive coupling group on the incoming nucleoside to the 5'-hydroxyl group of the support-bound species; capping of unreacted 5'-hydroxyl groups; and oxidation of the internucleotide linkage. Typically, the reactive coupling group is a 5'-silyl-2'-orthoester-3'-phosphoramidite such as a 5'-O-benzhydroxy-bis(trimethylsilyloxy)silyl-2'-O-bis(2-acetoxyethyl)orthoformyl-3'-O-(N,N-diisopropyl)methyl phosphoramidite (e.g., Structure 1). The sense strand can be synthesized to have 2'-O-methyl nucleosides in positions 1 and 2 (e.g., $mX_q$, q=1 and 2). These modified nucleosides are incorporated using the sequence-appropriate 5'-silyl-2'-O-methyl-3'-phosphoramidites, in particular, 5'-O-benzhydroxy-bis(trimethylsilyloxy)-silyl-2'-O-methyl-3'-O-(N,N-diisopropyl)methyl phosphoramidites (e.g. Structure 2). Structures 1 and 2 are characterized by the following: B is a nucleoside base such as adenosine, guanosine, cytidine or uridine; and Z is a protecting group for the exocyclic amine (e.g., isobutyryl for A and G, acetyl for C). The antisense strand is synthesized to have a phosphate group on the 5'-terminal nucleotide (e.g., position 1). This phosphate group is introduced chemically using N,N-diisopropylamino-bis(2-cyanoethyl) phosphoramidite (e.g., Structure 3). The complete sense strand is as follows: 5'> HO-$mX_1mX_2X_3X_4X_5X_6X_7X_8X_9X_{10}X_{11}X_{12}X_{13}X_{14}X_{15}X_{16}X_{17}X_{18}X_{19}X_{20}X_{21}$—OH <3'. The complete antisense strand is as follows: 3'> HO—$Y_{21}Y_{20}Y_{19}Y_{18}Y_{17}Y_{16}Y_{15}Y_{14}Y_{13}Y_{12}Y_{11}Y_{10}Y_9Y_8Y_7X_6Y_5Y_4Y_3Y_2Y_1$—$PO_4$ <5'. The $X_q$ and $Y_q$ nucleosides include A, C, G, or U. The $mX_q$ nucleosides are 2'-O-methyl nucleosides including 2'-O-methyl-A, 2'-O-methyl-C, 2'-O-methyl-G, and 2'-O-methyl-U. The sense strand and antisense strands can form a duplex siRNA.

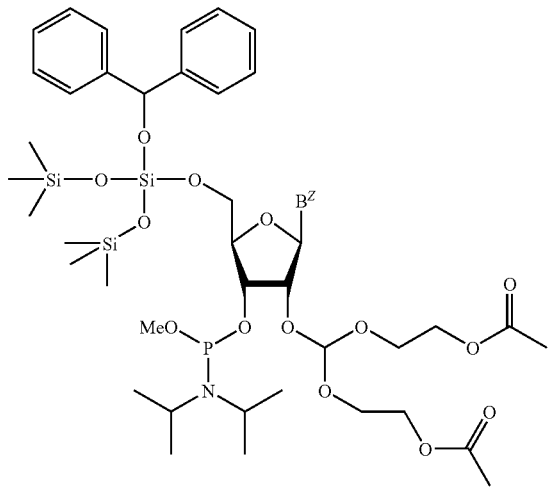

STRUCTURE 1

37

-continued

STRUCTURE 2

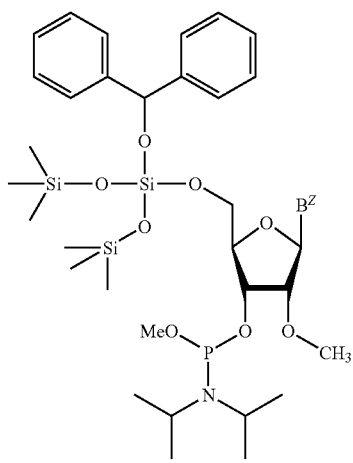

STRUCTURE 3

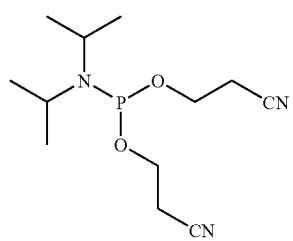

Example 3

Another siRNA duplex is prepared with substantially the same synthesis procedure as described in Example 2. More particularly, the sense strand is prepared as described in Example 2, and the antisense strand is prepared similarly except that nucleosides $mY_1$ and $mY_2$ include the 2'-O-methyl nucleosides. Accordingly, the 2'-O-methyl nucleosides on the antisense strand are incorporated as described in Example 2 for the sense strand. The completed sense strand is as follows: 5'> HO-$mX_1mX_2X_3X_4X_5X_6X_7X_8X_9X_{10}X_{11}X_{12}X_{13}X_{14}X_{15}X_{16}X_{17}X_{18}X_{19}X_{20}X_{21}$—OH <3'. The completed antisense strand is as follows: 3'> HO—$Y_{21}Y_{20}Y_{19}Y_{18}Y_{17}Y_{16}Y_{15}Y_{14}Y_{13}Y_{12}Y_{11}Y_{10}Y_9Y_8Y_7X_6Y_5Y_4Y_3mY_2mY_1$—$PO_4$ <5'. The $X_q$ and $Y_q$ nucleosides include A, C, G, or U. The $mX_q$ and $mY_q$ nucleosides are 2'-O-methyl nucleosides including 2'-O-methyl-A, 2'-O-methyl-C, 2'-O-methyl-G, and 2'-O-methyl-U. The sense strand and antisense strands can form a duplex siRNA as described in Example 2.

Example 4

Another siRNA duplex is prepared with substantially the same synthesis procedure as described in Example 2. More particularly, the sense strand is prepared as described in Example 2, and the antisense strand is prepared similarly except that nucleoside $mY_2$ includes the 2'-O-methyl nucleoside. Accordingly, the 2'-O-methyl nucleosides on the antisense strand are incorporated as described in Example 2 for the sense strand. The completed sense strand is as follows: 5'> HO-$mX_1mX_2X_3X_4X_5X_6X_7X_8X_9X_{10}X_{11}X_{12}X_{13}X_{14}X_{15}X_{16}X_{17}X_{18}X_{19}X_{20}X_{21}$—OH<3'. The completed antisense strand is as follows: 3'> HO—$Y_{21}Y_{20}Y_{19}Y_{18}Y_{17}Y_{16}Y_{15}Y_{14}Y_{13}Y_{12}Y_{11}Y_{10}Y_9Y_8Y_7X_6Y_5Y_4Y_3mY_2mY_1$—$PO_4$ <5'. The $X_q$ and $Y_q$ nucleosides include A, C, G, or U. The $mX_q$ and $mY_q$ nucleosides are 2'-O-methyl nucleosides including 2'-O-methyl-A, 2'-O-methyl-C, 2'-O-methyl-G, and 2'-O-methyl-U. The sense strand and antisense strands can form a duplex siRNA as described in Example 2.

Example 5

In the following examples, cell cultures are used in order to study gene silencing, mRNA detection, cell toxicity, transfection efficacy, and the like. Accordingly, the cell cultures can be maintained and cultivated by techniques well know in the art. The level of expression and gene silencing can be studied by a branched DNA ("B-DNA") assay (Genospectra, Fremont, Calif.) or equivalent, art-recognized techniques. Cell toxicity can be assessed for the gene silencing studies using AlamarBlue assays (Biosource International, Camarillo Calif.), which were performed to assess the degree of cell death resulting from experimental procedures.

Example 6

Reverse transfection ("RTF") protocols were conducted with DNA and siRNA in order to determine whether an RTF procedure configured for DNA can be applied straight across for siRNA. Accordingly, the DNA and siRNA were reverse transfected into cells using a variety of lipids, lipid concentrations, and plasmid or siRNA concentrations. RTF of plasmid DNA was conducted using 96-well poly-L-lysine plates, where solutions of 62.5-250 ng of the pCMV-Luc (e.g., well known luciferase expression plasmid) in a volume of 50 uL ("uL") were deposited and dried into the wells. Subsequently, the pCMV-Luc was solubilized and complexed with LIPOFECTAMINE™ 2000-media, OLIGOFECTAMINE™-media, and TRANSIT-TKO™-media (Opti-MEM™) in different wells, wherein the lipid was added at 0.125-1 micrograms ("ug") per well in a total volume of 30 uL. The complexes were allowed to form for 30-60 minutes before 10,000 HeLa cells in 70 uL of media were added to obtain a total of 100 uL. The plates were incubated for 48 hours and tested for luciferase expression using the STEADYGLOW™ kit (Promega).

As a control, pCMV-Luc was introduced into cells using a forward transfection procedure. Specifically, HeLa cells were plated at a density of 10,000 cells per well in a 96-well plate. On the following day, varying amounts of pCMV-Luc were complexed with LIPOFECTAMINE™ 2000 for 20 minutes at room temperature, and mixed with Opti-MEM™ (e.g. 80 uL of Opti-MEM™ for each 20 uL of LIPOFECTAMINE™ 2000-plasmid mixture). The culture media was removed from each well, and 50 uL of Opti-MEM™, and 50 uL of the lipid-CMV-Luc plasmid-media complex, were added in succession. As a result of these procedures, the final amount of CMV-Luc plasmid and lipid was between 5-50 ng, and 0.125-1.0 ug per well, respectively.

A control siRNA was reverse transfected into the same cell line in order to be compared with the DNA RTF. About 62.5-250 nanograms of cyclophilin B siRNA (e.g., cyclo 3) in a volume of 25 uL were deposited and dried on 96-well poly-L-lysine plates. The siRNA was solubilized and complexed with LIPOFECTAMINE™ 2000-media, OLIGOFECTAMINE™-media, Transit-TKO-media, or "siRNA168"-media (Opti-MEM™) in different wells, wherein the lipid was delivered at about 0.156-1.25 ug per well in a total volume of 25 uL. The siRNA168 is a lipid formulated for siRNA delivery. The complexes were allowed to form for 30-60 minutes before 10,000 HeLa cells in 75 uL of media were added for a total volume of 100 uL. The plates were then incubated for 48 hours and assessed for the level of down-regulation of the human cyclophilin B mRNA using a B-DNA assay.

The results to these studies are provided in FIGS. 2A-2F, which are graphs illustrating the efficacy of the RTF procedures. The graphs depict the RTF procedures have disproportionate levels of delivery between the DNA and siRNA. While pCMV-Luc is easily transfected and expressed in cells using the forward transfection protocol, the RTF protocol showed poor delivery. In contrast, conditions were identified where RTF of the cyclo 3 siRNA using LIPOFECTAMINE™ 2000 was successful and provided excellent gene silencing. These results demonstrate the disparate nature of DNA and siRNA in RTF protocols. In addition, the data show that the effectiveness of lipids in siRNA RTF varies considerably.

Example 7

The ability of RTF protocols to achieve gene silencing was studied in relation to siRNA functionality. Varying siRNAs functionalities (e.g., F50-F95) were reverse transfected at a single cell density or 10,000 cells per well using lipid concentrations of 0.031-0.5 ug of lipid per 100 mL. Specifically, cyclo 3, cyclo 14, cyclo 28, and cyclo 37, which have silencing functionalities of 95, 90, 75, and 50, respectively, were suspended in RNase-free H$_2$O at varying concentrations and deposited and dried on the well floors 96-well plates. About 25 uL of a DharmaFECT™ 1-OptiMEM™ were added to each well to achieve final lipid concentrations of 0.031-0.5 ug per 100 uL to solubilize and complex the siRNA for 30-60 minutes at room temperature before 10,000 HeLa cells were added to each well. The gene silencing was studied over four days.

FIGS. 3A-3F are graphical representations of the results obtained from the gene silencing assay. As depicted in the graphs, highly functional siRNAs (e.g., cyclo 3 and 14) exhibited silencing for longer periods of time (e.g., 4 days) in comparison with moderately functional siRNA (e.g., cyclo 28, 2 days) or poorly functional siRNA (e.g., cyclo 37, 0 days). Thus, the selection of functional siRNA by rational design can greatly improve the longevity of gene silencing.

Example 8

The ability of siRNA to induce off-targeting effects were assayed using forward transfection protocols. Specifically, modified and unmodified IGF1R-73 siRNAs were transfected into cells in a forward transfection format, and the mRNA were purified from cell lysates and analyzed using Agilent microArrays. The modifications included addition of 2' O-methyl groups to the first and second sense nucleotides, plus addition of 2'-O-methyl groups to the second antisense nucleotide, plus addition of a phosphate group to the 5' position of the antisense 5' terminal nucleotide. Briefly, 1 ug of total RNA isolated from untreated or siRNA-treated cells was amplified, and labeled with Cy5™ or Cy3™ (Perkin Elmer) using Agilent's Low Input RNA Fluorescent Linear Amplification Kit. Hybridizations were performed using Agilent's Human 1A (V2) Oligo Microarrays (e.g., 22,000 sequences) according to standard protocol, with 750 nanograms each of Cy-3™ and Cy-5™ labeled material loaded onto each array. Slides were washed using 6x and 0.06xSSPE each with 0.025% N-lauroylsarcosine, and dried using Agilent's non-aqueous drying and stabilization solution. Biological replicates of each sample array were scanned on an Agilent Microarray Scanner (model G2505B), and the raw image was processed using Feature Extraction software (v6.1.1 or v7.5.1). Further analysis was performed using Spotfire Decision Site 7.2 software and the Spotfire Functional Genomics Module. Low signal genes having less than 2.8 in a self-self hybridization calculated from the log base 10 of the green and red processed signal sum were removed from the analysis. A 2-fold cutoff (e.g., Log Ratio of >0.3 or <−0.3) was applied to genes used in comparative analysis. Outlier flagging was not used.

Figure 4:
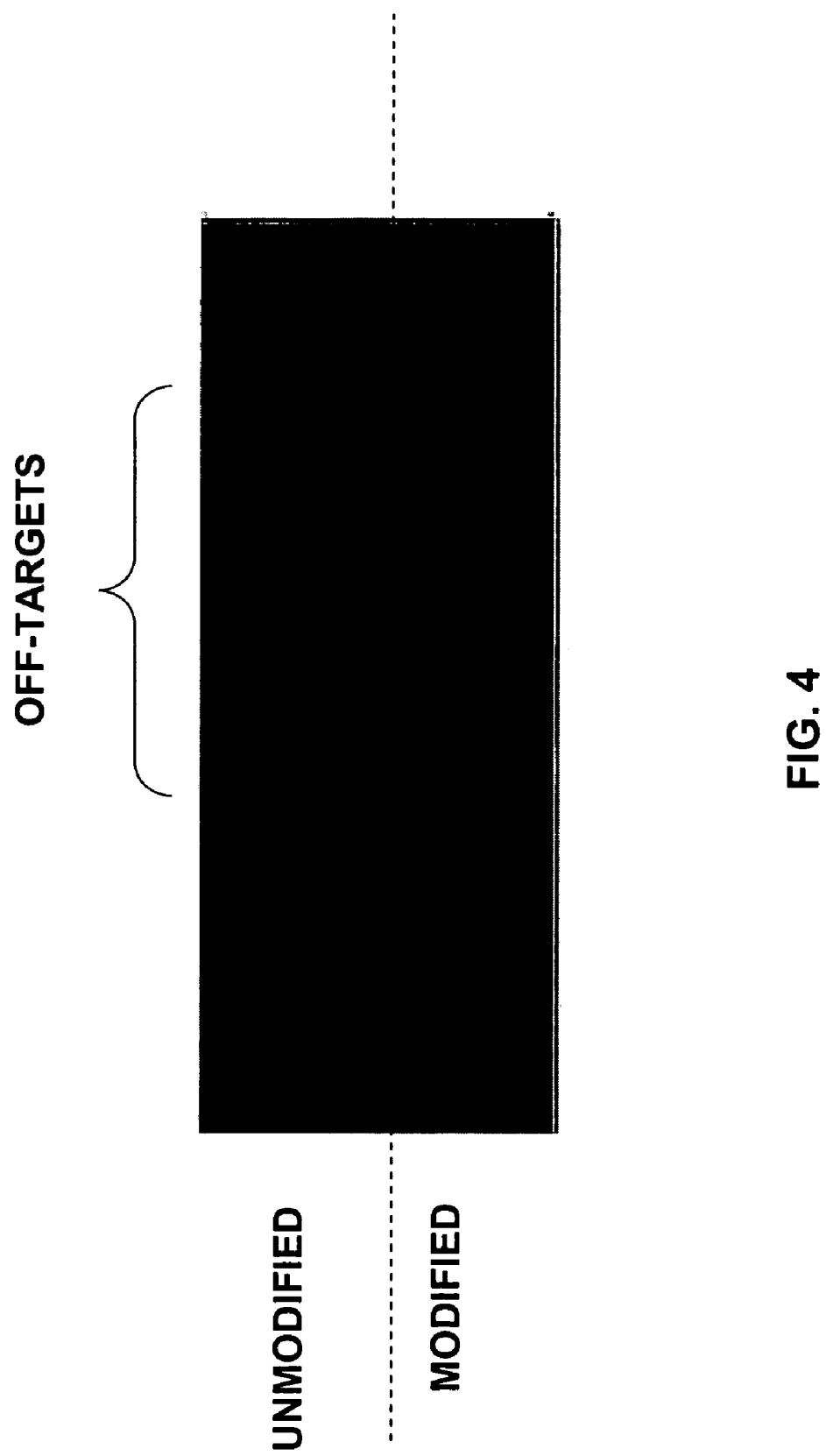
FIG. 4 is an image of a heatmap of an embodiment of siRNA-induced off-target silencing by microarray analysis. The top light lines highlighted by the bracketed region represent down-regulated genes that were off-targeted by unmodified IGFR1-73 siRNA. The bottom lines show that the number of off-targets is substantially reduced when IGFR1-73 siRNA is chemically modified.

FIG. 4 is an image that depicts the results of these experiments, and show that siRNA IGF1R-73 down-regulates a wide array of genes. In FIG. 4, the off-targets are shown as lighter colored lines at the top right side of the image, which were the unmodified siRNA. On the other hand, the modified siRNA did not show substantial off-targeting. These off-target effects are highly detrimental in that they can generate false positives during genome wide siRNA screens.

Example 9

The ability of modified siRNA to reduce off-target effects and to reduce off-target generated phenotypes was studied with siRNA having toxic motifs. The toxic siRNA were modified by the addition of 2' O-methyl groups to the first and second sense nucleotides, plus addition of 2'-O-methyl groups to the second antisense nucleotide, plus addition of a phosphate group to the 5' position of the antisense 5' terminal nucleotide. This modification significantly reduces off-target effects generated by the duplexes.

Figure 5:
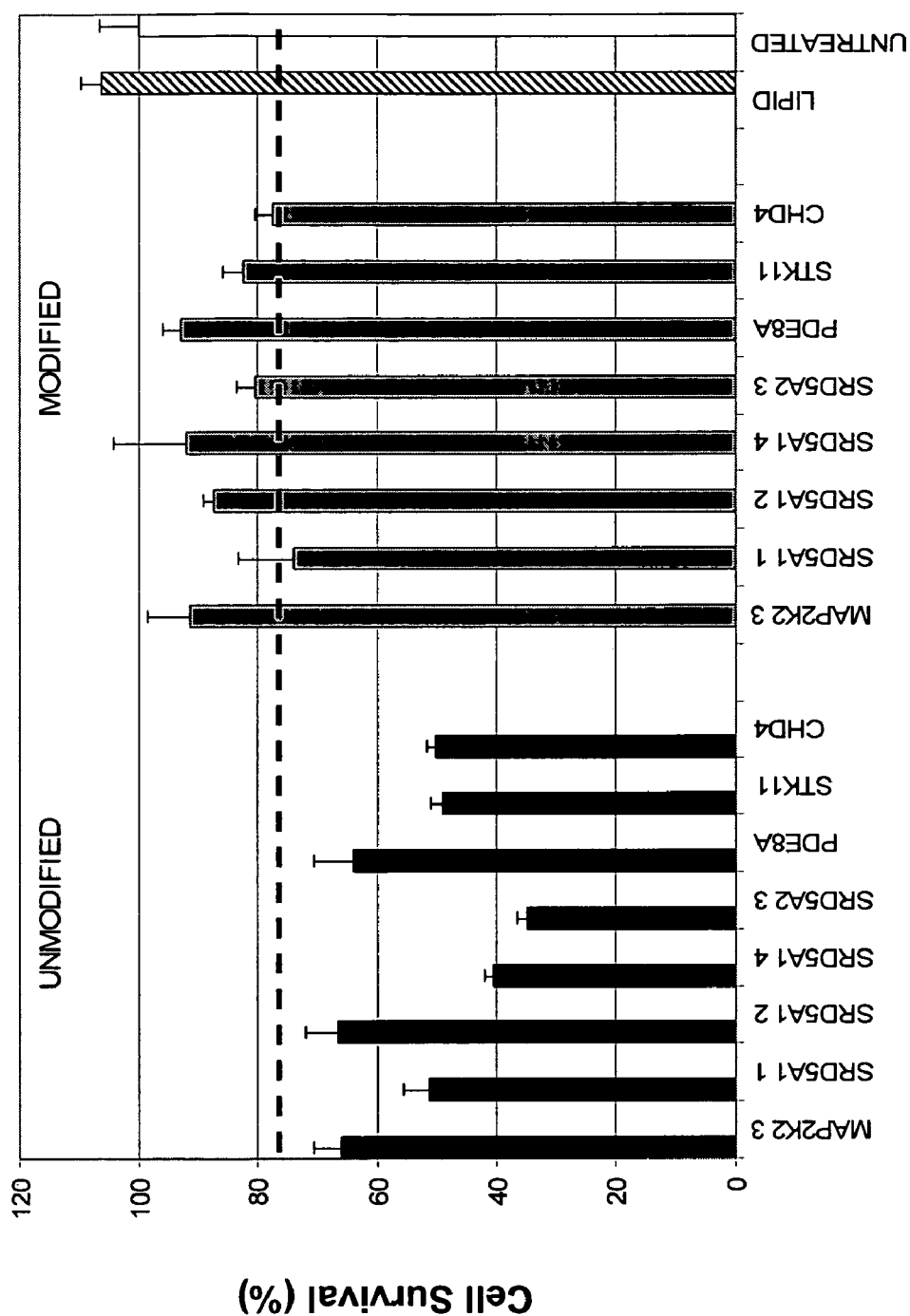
FIG. 5 is a graphical representation of an embodiment of the effects of chemically modified siRNA on cell viability.

FIG. 5 is a graphical representation of the cell toxicity that arises when toxic siRNA are modified. The graph shows that the eight separate unmodified toxic siRNA (e.g., MAP2K2 d3, SRD5A1 d1, SRD5A1 d2, SRD5A1 d4, SRD5A2 d3, PDE8A, STK11, and CHD4) all decreased cell viability below 75%. In contrast, chemical modification of all eight duplexes markedly decreased siRNA-induced toxicity without significantly altering target specific silencing. These findings demonstrate that addition of the chemical modifications to siRNA can eliminate off-target generated phenotypes.

Example 10

Figure 6:
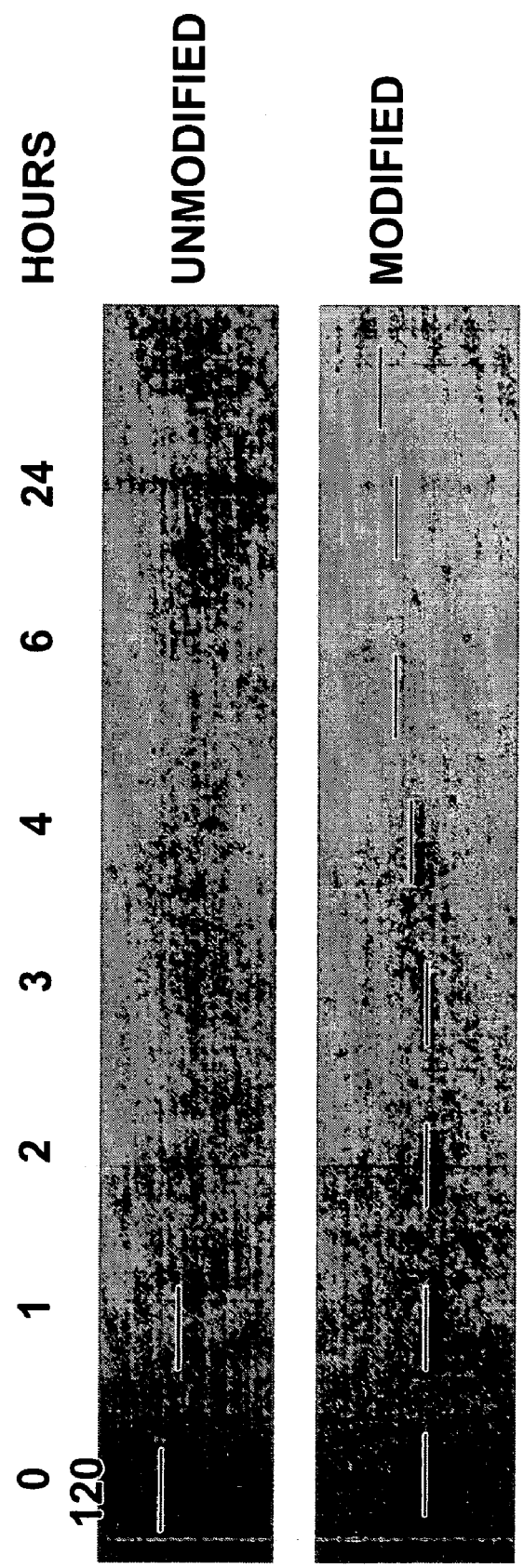
FIG. 6 is an image of an embodiment of an EtBr stained gel showing the rate of degradation of modified and unmodified siRNA, wherein the overlaid lines have been included to better depict the presence of non-degraded siRNA.

The stability of siRNA resistance to nucleases was investigated by incubating siRNA with 100% human serum. The siRNA was then examined on agarose gels stained with ethidium bromide. FIG. 6 is an image of the gel, which shows that unmodified siRNA degraded quickly in the presence of RNases and had a half-life that is measured in minutes. As shown, lines were added over the visible polynucleotide bands for clarity purposes. Accordingly, the modified siRNA were able to maintain their integrity over the course of the study. Thus, the results indicate that modified siRNA may be capable of maintaining their integrity for longer durations. This can be important because plates in accordance with the present invention include dry siRNA, and these plates may need a shelf-life that extends for weeks to months where there is a potential for RNase contamination and siRNA degradation.

Example 11

The ability of stabilization modified siRNA to resist degradation by an RNase was studied. The stabilized siRNA were modified with the following: 2'-O-methyl groups on the first and second sense nucleotides; 2'-O-methyl groups on all sense pyrimidine nucleotides (e.g., C and U); 2'-F modification on all antisense pyrimidine nucleotides; and a phosphate group on the 5' carbon of the antisense 5' terminal nucleotide.

Figure 7:
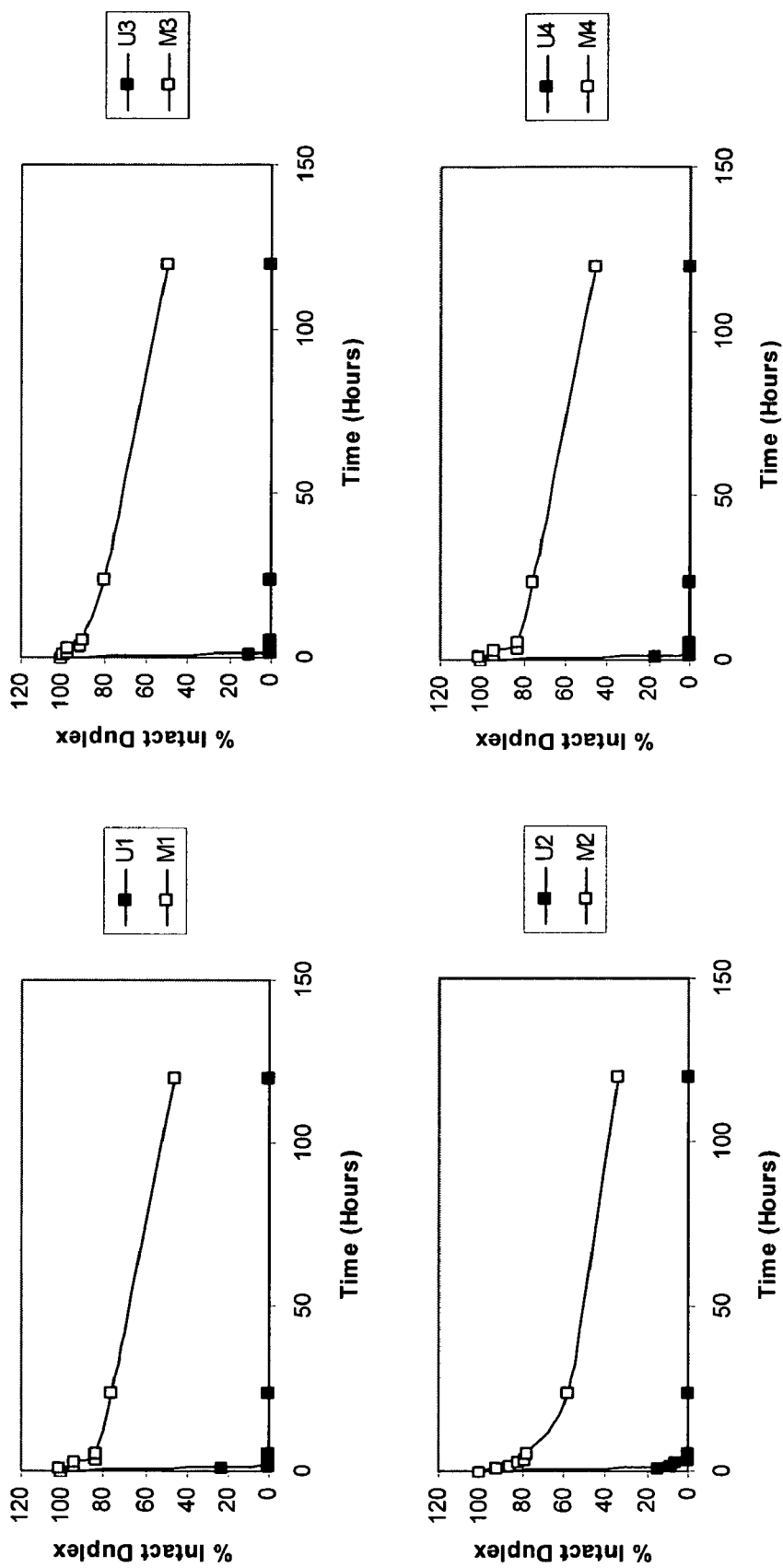
FIG. 7 provides graphical representations of an embodiment of the ability and inability of RNases present in serum to degrade unmodified and modified siRNA by showing the kinetics of degradation of four different modified and unmodified siRNA.

FIG. 7 includes graphical representations of four modified siRNA (e.g., M1-M4) and four unmodified siRNA (e.g., U1-U4). The graphs show that the modified siRNA significantly resist degradation in comparison to the unmodified siRNA. The modification pattern increased the serum half-life of siRNA from minutes to greater than 100 hours.

Example 12

Figure 8:
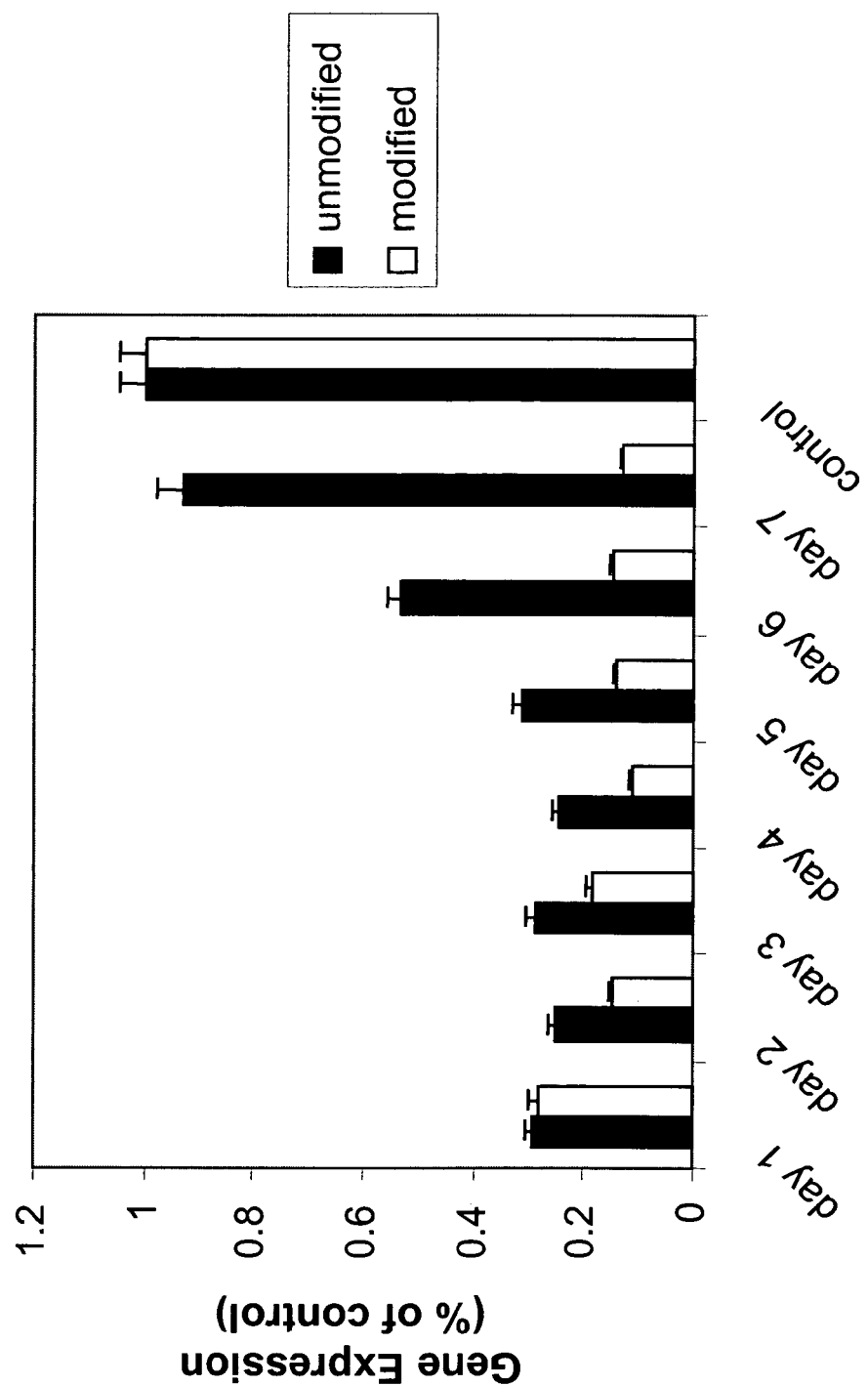
FIG. 8 is a graphical representation of an embodiment of the longevity of silencing with unmodified and stabilization modified siRNA, where DF1 is DharmaFECT™ 1.

The ability of stabilization modified siRNA subjected to degradation by an RNase to retain functionality was studied. The functionality tests were performed with siRNA modified as described in Example 11 by forward transfection and compared to unmodified siRNA. FIG. 8 graphically shows the chemical modification pattern to preserved functional silencing of the intended target over a longer period of time. While silencing by unmodified siRNA lasted 4-5 days, modified siRNA silenced the prescribed targeted for greater than 7 days. Thus, the chemical modification should also be able to enhance the efficacy of silencing using the RTF format.

Example 13

The ability to use stabilization modified siRNA in an RTF protocol was studied in comparison with unmodified siRNA. The stabilization modified siRNA had the same modification as described in Example 11 on siRNA targeting human cyclophilin B (cyclo 3). The siRNA in an aqueous solution were dried in wells of 96-well poly-L-lysine treated plates to produce 61.5, 125, or 250 nM concentrations when 125 uL of lipid-media and cells were added. Lipid solutions of LIPOFECTAMINE™ 2000-Opti-MEM™, TKO-Opti-MEM™, or DharmaFECT™ 1-Opti-MEM™ were added to the wells at 0.125, 0.25, or 0.5 total ug of lipid per 100 uL to solubilize and complex the siRNA for 30-60 minutes. About 10,000 HeLa cells were added to each well and maintained for 48 hours prior to assaying for toxicity, and cyclophilin B mRNA silencing.

Figure 9A:
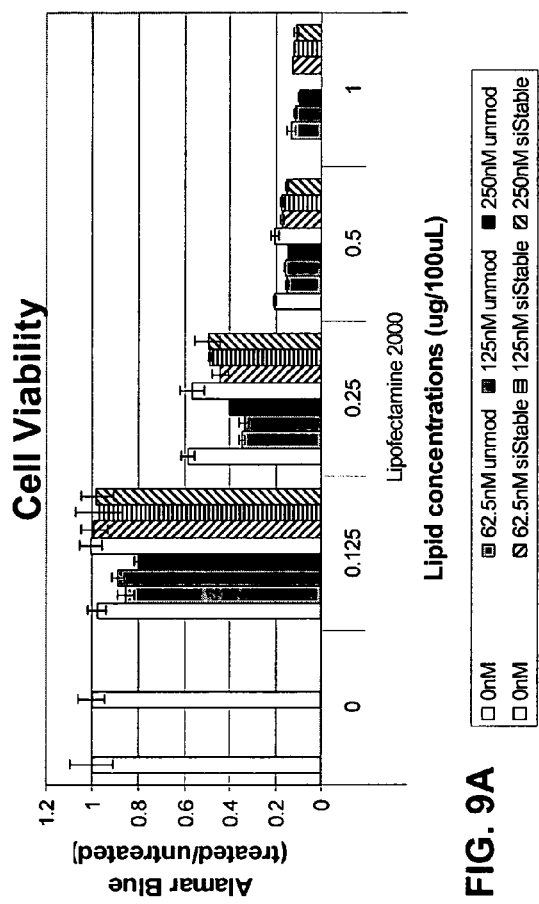
FIG. 9A is a graphical representation of an embodiment of cell viability with LIPOFECTAMNE™ 2000 and stabilized and unstabilized siRNA.
Figure 9B:
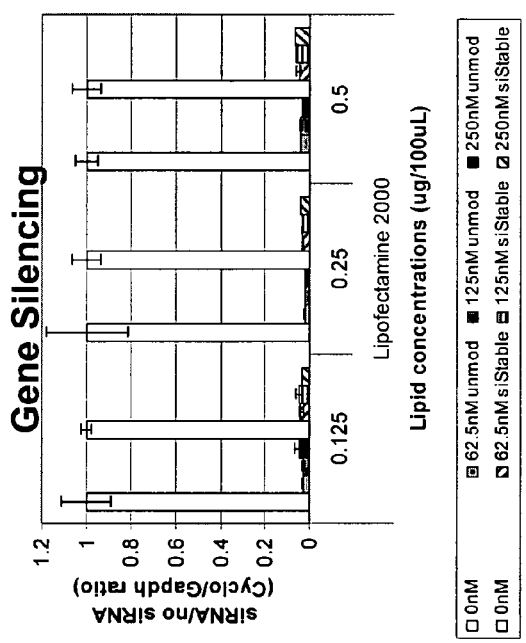
FIG. 9B is a graphical representation of an embodiment of the gene silencing of the conditions of FIG. 9A.

FIG. 9A graphically illustrates the modified and unmodified siRNA to performed similarly, and only 0.125 ug per 100 uL of LIPOFECTAMINE™ 2000 resulted in acceptable levels of cell viability. While higher levels of lipid generated unacceptable levels of cell death, it was observed that under conditions of 0.25 ug of lipid per 100 uL, modified duplexes induced less toxicity than unmodified duplexes. This observation suggests that the modification pattern has an added benefit of limiting cellular toxicity of siRNA introduced by RTF. FIG. 9B graphically illustrates that the gene silencing induced by modified and unmodified duplexes using LIPOFECTAMINE™ 2000 was nearly identical.

Figure 10A:
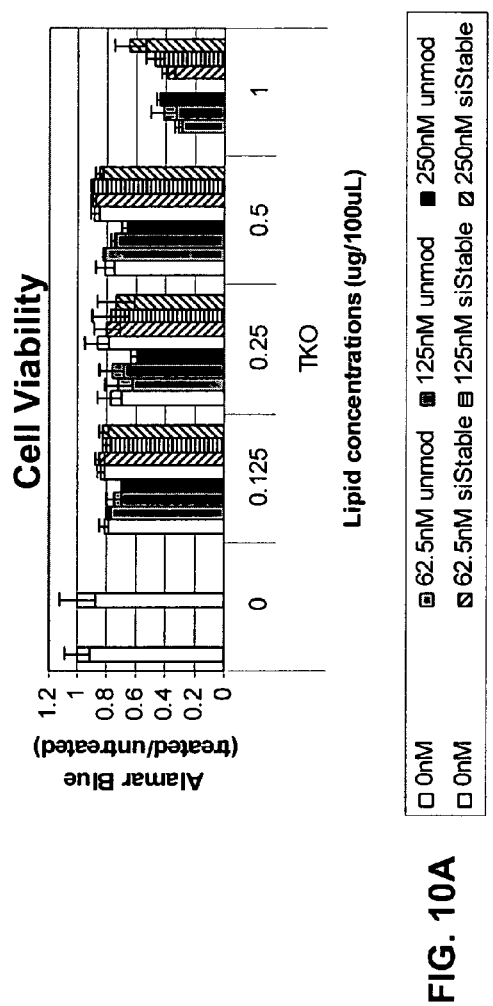
FIG. 10A is a graphical representation of an embodiment of cell viability with TKO and stabilized and unstabilized siRNA.
Figure 10B:
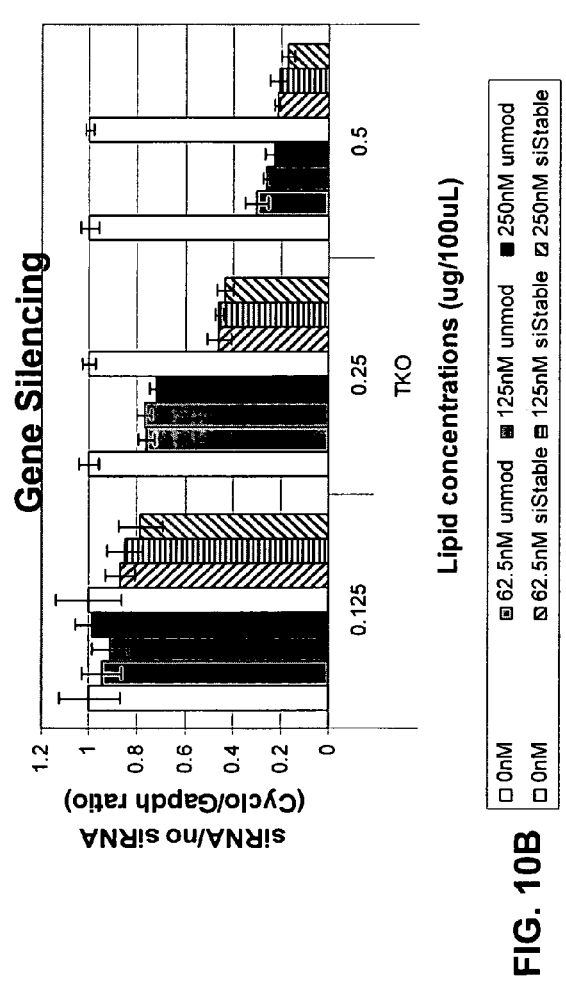
FIG. 10B is a graphical representation of an embodiment of the gene silencing of the conditions of FIG. 10A.

FIG. 10A graphically illustrates TKO lipid concentrations between 0.125-0.5 ug of lipid per 100 uL did not alter cell viability below about 80% of that observed in controls. Unfortunately, the silencing proficiency of siRNA under these conditions is more limited, as shown in FIG. 10B, wherein nearly all concentrations of siRNA silenced cyclophilin B by only 40% at 0.125 ug of lipid per 100 uL, by about 50-70% at 0.25 ug of lipid per 100 uL, and by 80-90% at 0.5 ug per 100 uL. These results demonstrate the chemical modifications did not appreciably alter the toxicity or silencing efficiency of the siRNA. Furthermore, this shows that not all lipids provided equivalent delivery in the RTF format.

FIG. 11A graphically illustrates that the toxicity of DharmaFECT™ 1 was similar for modified and unmodified siRNA at 0.125 ug per 100 uL, and were less toxic compared to LIPOFECTAMINE™ 2000 and TKO studies. Additionally, DharmaFECT™ 1 was less toxic with modified siRNA compared to unmodified siRNA. FIG. 11B graphically represents the gene silencing efficiency to be comparable at 0.125 ug per 100 uL. Thus, under these conditions, addition of the described chemical modifications to siRNA did not alter silencing efficiency of the duplex.

Example 14

Figure 12:
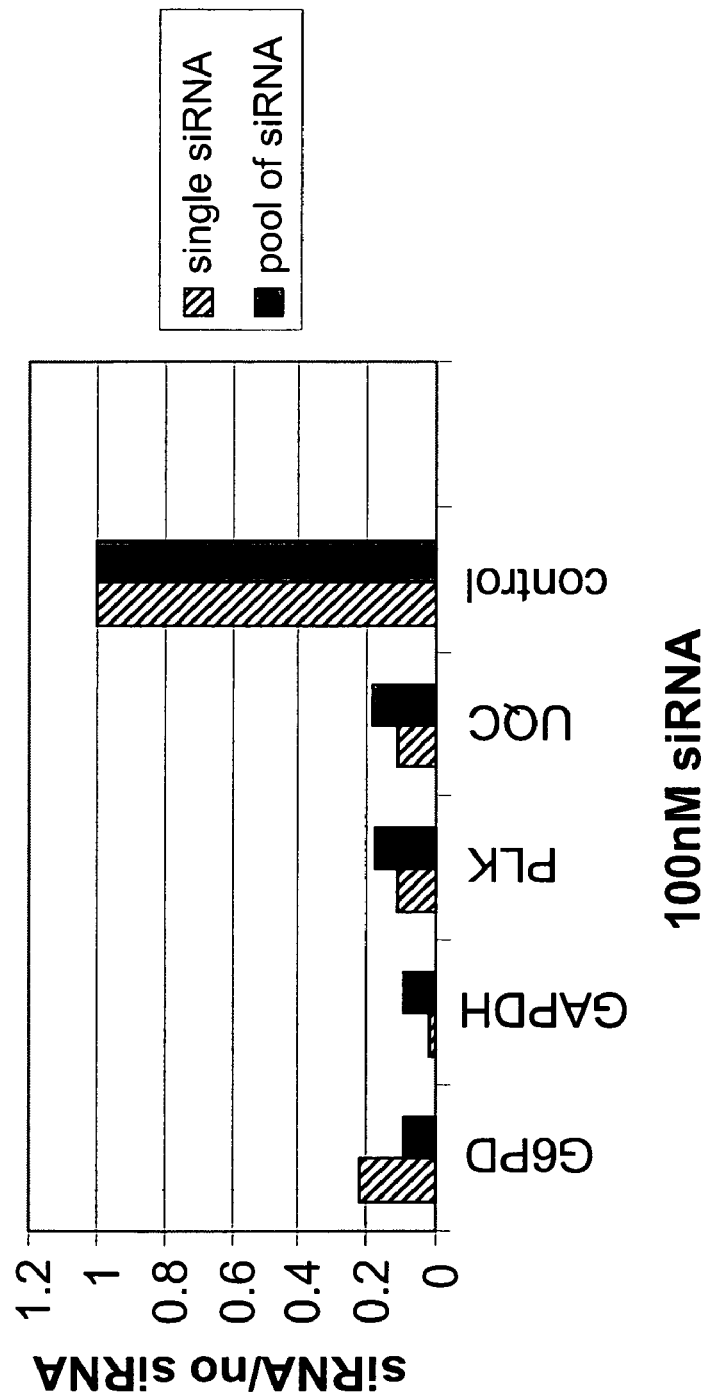
FIG. 12 is a graphical representation of an embodiment of multi-gene silencing using single and pooled siRNA.

The ability of rationally designed pools of siRNA to silence four separate genes was studied with siRNA targeting G6PD, GAPDH, PLK, and UQC. Pools of siRNA (e.g., 4 siRNA per gene) were forward transfected into cells at a total siRNA concentration of 100 nM, 6.25 nM per siRNA, using LIPOFECTAMINE™ 2000, and assayed twenty-four hours later by B-DNA. FIG. 12 is a graphical representation of the results which demonstrated that pools of rationally designed molecules are capable of simultaneously silencing four different genes. The ability to target multiple genes in an RTF format will significantly simplify the ability to use RTF for screening large (e.g., genome-sized) collections of siRNA.

Example 15

The importance of cell density in RTF protocols was studied. Solutions of cyclo 3, cyclo 14, cyclo 28, and cyclo 37 siRNA were deposited and dried on the bottom of poly-L-lysine coated 96-well plates for final concentrations of 4 nM, 8 nM, 15.5 nM, 31 nM, 62.5 nM, 125 nM, and 250 nM. Lipid solutions of DharmaFECT™ 1-Opti-MEM™ were added to each well at 25 uL for final concentrations of 0.015 ug, 0.031 ug, 0.063 ug, 0.125 ug, or 0.25 ug of lipid per 100 uL were obtained. The DharmaFECT™ 1-Opti-MEM™ mixtures were allowed to solubilize and complex the dried siRNA for 30-60 minutes before the addition of HeLa cells at 5,000, 10,000, 20,000, or 40,000 cells per well. "Acceptable viability" is defined as about 80% viability or greater. "Acceptable silencing" is defined as about 80% silencing or greater."

FIG. 13A is a graphical illustration of the gene silencing on day 2 with a cell density of 5,000 cells per well. The graph shows that up to 0.031 ug of lipid per 100 uL and 125-250 nM siRNA provided acceptable levels of silencing by three (e.g., cyclo 3 and cyclo 14, and cyclo 28) out of the four siRNA tested. FIG. 13B is a corresponding graphical representation of toxicity, which shows minimal levels of toxicity until the lipid increased to 0.125 ug of lipid per 100 uL. All other conditions produced either unacceptable levels of silencing and/or cell death across the collection of siRNA tested.

FIG. 14A is a graphical illustration of the gene silencing on day 4 with a cell density of 5,000 cells per well. The graph shows that up to 0.063 ug of lipid per 100 uL and 15.5 nM-62.5 nM siRNA provided acceptable levels of silencing by two (e.g., cyclo 3 and cyclo 14) out of the four siRNA tested. FIG. 14B is a corresponding graphical representation of toxicity, which shows 0.063 ug of lipid per 100 uL and 15.5 nM-62.5 nM siRNA provided acceptable toxicity, except for cyco37. All other conditions produced either unacceptable levels of silencing and/or cell death across the collection of siRNA tested.

FIG. 15A is a graphical illustration of the gene silencing on day 8 with a cell density of 5,000 cells per well. The graph shows none of the test levels were sufficient. FIG. 15B is a graphical illustration of the toxicity, which show all conditions were overly toxic, which may be more of a function of the duration rather than actual toxicity of the conditions.

FIG. 16A is a graphical illustration of the gene silencing on day 1 with a cell density of 10,000 cells per well. The graph shows that up to 0.063 ug of lipid per 100 uL provided acceptable levels of silencing by two (e.g., cyclo 3 and cyclo 14) out of the four siRNA tested. FIG. 16B is the graphical illustration of toxicity, which was minimal under the optimal silencing conditions. All other conditions produced either unacceptable levels of silencing and/or cell death across the collection of siRNA tested.

FIG. 17A is a graphical illustration of the gene silencing on day 2 with a cell density of 10,000 cells per well. The graph shows that up to 0.063 ug of lipid per 100 uL provided acceptable levels of silencing by two (e.g., cyclo 3 and cyclo 14) out of the four siRNA tested. FIG. 17B is the graphical illustration of toxicity, which was minimal under the optimal silencing conditions. All other conditions produced either unacceptable levels of silencing and/or cell death across the collection of siRNA tested.

FIG. 18A is a graphical illustration of the gene silencing on day 4 with a cell density of 10,000 cells per well. The graph shows that up to 0.063 ug of lipid per 100 uL and 4-31 nM of siRNA provided acceptable levels of silencing by two (e.g., cyclo 3 and cyclo 14) out of the four siRNA tested. FIG. 18B is the graphical illustration of toxicity, which was minimal under the optimal silencing conditions. All other conditions produced either unacceptable levels of silencing and/or cell death across the collection of siRNA tested.

FIG. 19A is a graphical illustration of the gene silencing on day 1 with a cell density of 20,000 cells per well. The graph shows that up to 0.125 ug of lipid per 100 uL and 125-250 nM siRNA provided acceptable levels of silencing by one (e.g., cyclo 14) out of the four siRNA tested. FIG. 19B is the graphical illustration of toxicity, which was minimal under the optimal silencing conditions. All other conditions produced either unacceptable levels of silencing and/or cell death across the collection of siRNA tested.

FIG. 20A is a graphical illustration of the gene silencing on day 2 with a cell density of 20,000 cells per well. The graph shows that up to 0.125 ug of lipid per 100 uL provided acceptable levels of silencing by two (e.g., cyclo 3 and cyclo 14) out of the four siRNA tested. FIG. 20B is the graphical illustration of toxicity, which was minimal under the optimal silencing conditions. All other conditions produced either unacceptable levels of silencing and/or cell death across the collection of siRNA tested.

FIG. 21A is a graphical illustration of the gene silencing on day 1 with a cell density of 40,000 cells per well. The graph shows that none of the conditions were acceptable. Additionally, FIG. 21B shows no acceptable toxicity. The results suggest that the process of reverse transfection is extremely sensitive to cell densities and that densities of less than 40,000 cells per well (in a 96-well plate) are preferred for successful gene knockdown in this format.

Example 16

The genes involved in the kinase pathway are studied by siRNA RTF to determine the genes responsible for cell viability. Rationally designed siRNAs targeting the 779 members of the kinase family are solubilized in RNase-free water and dried in individual wells of PLL coated 96-well plates. The amount of each siRNA is approximately 25 nM for 125 uL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HeLa cells in media are added for a final volume of 125 uL. The plates are maintained between 24 and 72 hours and assayed for cell viability. A comparison between the cell viability of cultures that were treated with lipid alone (i.e., control wells) and cultures treated with individual members of the Kinase siRNA array allows the identification of genes that are essential for HeLa cell viability.

Example 17

The genes involved in the cytokine receptor family are studied by siRNA RTF to determine the genes responsible for cell viability. Rationally designed siRNAs targeting the 166 members of the cytokine receptor family are solubilized in RNase-free water and dried in individual wells of PLL coated 96-well plates. The amount of each siRNA is approximately 25 nM for 125 µL of total solution. A lipid solution having 0.1 ug of DharmaFECT™ 1 lipid in 25 uL total volume of Hanks Balanced Saline Buffer is added to each well and incubated for 20-40 minutes to solubilize and complex the siRNA before 10,000 HT-29 cells in media are added for a final volume of 125 uL. The plates are maintained between 24 and 72 hours and assayed for cell viability. A comparison between the cell viability of cultures that were treated with lipid alone (i.e., control wells) and cultures treated with individual members of the cytokine receptor siRNA array allows the identification of genes that are essential for HT-29 cell viability.

Example 18

The ability of different lipid-containing solutions, which are aqueous based, to reduce or inhibit cell toxicity in siRNA RTF protocols was studied with siRNA having toxic motifs. A group of siRNAs containing the motifs AAA/UUU or GCCA/UGGC can induce cellular stress or death when administered alone or in combination with other stress-inducing factors (e.g., toxic small molecules, lipid solutions, lipids) were studied. Specifically, toxic siRNA directed against the SRD5a1 (sense, 5' CCGGAAATTTGAAGAGTAT SEQ. ID NO. 2) gene were dried on PLL-coated plates. The toxic siRNA used in these studies were either unmodified, or modified. A first modification includes 2'-O-methyl groups on the first and second sense nucleotides, 2'-O-methyl groups on the second antisense nucleotide, and a phosphate group on the 5' carbon of the antisense 5' terminal nucleotide of the antisense strand (Mod T1). A second modification includes a 5' deoxy nucleotide on the sense 5' terminal nucleotide, a 2'-O-ethanol group on the second antisense nucleotide, and a phosphate group on the 5' carbon of the antisense 5' terminal nucleotide (Mod T2).

FIG. 22 is a graphical representation of the cell viability using LIPOFECTAMINE™ 2000 in Opti-MEM™ and HBSS. In Opti-MEM™ unmodified toxic siRNA induce greater than 20% cell death under all of the conditions (e.g., 10 nM and 100 nM siRNA) independent of the lipid concentration. However, 0.04 ug of lipid per 100 uL had a cell viability that bordered at 80%. Additionally, both modified siRNA had cell viabilities greater than 80%. In HBSS unmodified toxic siRNA did not induce cell toxicity at 0.04 and 0.06 ug of lipid per 100 uL total solution. Cellular toxicity of greater than 20% was only observed at 100 nM unmodified siRNA at 0.1 ug of lipid per 100 uL total solution. All modified siRNA exhibited minimal toxicity. These results show that HBSS can reduce toxicity in RTF protocols. Moreover, these results show chemically modified siRNA are compatible with RTF protocols and can limit off-target effects that generate stress and toxicity.

Example 19

The ability of different lipids to reduce or inhibit cell toxicity in siRNA RTF protocols was studied with siRNA having toxic motifs. The toxicity generated by these molecules can be nullified by addition of chemical modifications that prevent, limit, or alter imperfect binding to off-target molecules. Specifically, toxic siRNA directed against the SRD5a1 gene (sense, 5'-CCGGAAATTTGAAGAGTAT, SEQ ID NO. 2) were deposited and dried on well floors of PLL-coated 96-well plates to achieve final concentrations of 10 or 100 nM. The toxic siRNA used in these studies were either unmodified or modified as in Example 18.

FIG. 23A is a graphical representation of the cell viability for the different lipids. The LIPOFECTAMINE™ 2000-OptiMEM™ unmodified toxic siRNA induced greater than 20% cell death under all of the conditions (e.g., 10 nM and 100 nM siRNA) regardless of the lipid concentration (e.g., 0.04, 0.06, 0.08, and 0.1 ug per 100 uL of solution). One borderline exception to this was observed at 0.04 ug per 100 uL, where culture viability bordered at 80%. Additionally, modified siRNA decreased cell toxicity. The DharmaFECT™ 1-OptiMEM™ unmodified toxic siRNA were not toxic at 0.04 and 0.06 ug of lipid per 100 uL total solution with 10 nM siRNA. Cellular toxicity greater than 20% was observed at 0.08 and 0.1 ug of lipid per 100 uL total solution at both 10 nM and 100 nM siRNA. All modified siRNA exhibited minimal toxicity.

FIG. 23B graphically represents the level of silencing provided under each condition, which is depicted to be roughly equivalent in all the samples. Thus, the results show DharmaFECT™ 1 provides improvements to RTF protocols by minimizing the level of toxicity induced by sequences that stress cells over a wide range of lipid concentrations. Moreover, these experiments show that chemically modified siRNA are compatible with the described reverse transfection format and are effective in eliminating off-target effects that generate stress and toxicity.

Example 20

The ability of a pool of siRNA to be directed against a selected gene was studied in an RTF protocol. To assess the effectiveness of pools of siRNA directed against a single target individual siRNAs and pools of three or four siRNAs directed against GAPDH, MAP2K1, or MAP2K2 were reverse transfected into HeLa cells using DharmaFECT™ 1.

In this study, the siRNA are designated as follows and include the following sequences (e.g., sense strands, listed 5'→3'): GAPDH siRNA duplex 1 (CAACGGAUUUG-GUCGUAUU, SEQ. ID NO. 3), duplex 2 (CAACGGA-UUUGGUCGUALU, SEQ. ID NO. 3), duplex 3 (GAAU-UUGGCUACAGCAACA, SEQ. ID NO. 4), and duplex 4 (GAAAUCCCAUCACCAUCUU, SEQ. ID NO. 5); MAP2K1 siRNA duplex 1 (GCACAUGGAUGGAGG-UUCU, SEQ. ID NO. 6), duplex 2 (GCAGAGAGAGCAGA-UUUGA, SEQ. ID NO. 7), duplex 4 (GAGCAGA-UUUGAAGCAACU, SEQ. ID NO. 8), and duplex 5 (CCAGAAAGCUAAUUCAUCU, SEQ. ID NO. 9); MAP2K2 siRNA duplex 1 (CAAAGACGAUGACUUC-GAA, SEQ. ID NO. 10), duplex 2 (GAUCAGCAUUUG-CAUGGAA, SEQ. ID NO. 11), duplex 4 (GGAAGCUGAUCCACCUUGA, SEQ. ID NO. 12), and duplex 7 (GAAAGUCAGCAUCGCGGUU, SEQ. ID NO. 13).

FIG. 24A is a graphical representation of results of an embodiment of GAPGH silencing that show pools act as well as or better than individual siRNA. FIG. 24B is a graphical representation of results of an embodiment of MAP2K2 silencing that show pools act as well as or better than individual siRNA. FIG. 24C is a graphical representation of results of an embodiment of GAPDH silencing that show pools act as well as or better than individual siRNA, where the pool provided superior silencing to any individual siRNA at 10 nM. In all of the cases tested, gene silencing using individual siRNA or pools did not alter overall cell toxicity (data not shown). Another benefit of pools involves the consistency of performance. For instance, while individual duplexes targeting GAPDH and MAP2K2 performed adequately (e.g., greater than 80% silencing at concentrations between 1 nM and 100 nM for all 8 siRNA), only a single siRNA (e.g., duplex 4) at a single concentration (e.g., 50 nM) provided greater then 80% silencing for MAP2K1. In contrast, pooled siRNA targeting all three targets generated 80% or greater silencing at concentrations of 10 nM, 50 nM and 100 nM. These results demonstrate that pooling can provides increased consistency in gene silencing in the RTF format.

Example 21

The ability of a pool of siRNA to be directed against a selected gene was studied in an RTF protocol. To assess the effectiveness of pools of siRNA directed against a single target combinations of individual siRNAs directed to multiple targets. The siRNA directed to GAPDH, MAP2K1, or MAP2K2 were reverse transfected into HeLa cells using DharmaFECT™ 1. The siRNA used in these assays are the same as in Example 20.

FIGS. 25A-25C are graphical representations that demonstrate that compatibility with multi-gene knockdown. FIG. 25A shows the GAPDH knockdown in the presence of GAPDH duplex 1, MAP2K2 duplex 1, and MAP2K1 duplex 1 (1, 1&1); and GAPDH knockdown in the presence of GAPDH duplex 2, MAP2K2 duplex 2, and MAP2K1 duplex 2 (2, 2&2); GAPDH knockdown in the presence of GAPDH duplex 4, MAP2K2 duplex 4, and MAP2K1 duplex 3 (4, 4&3); GAPDH knockdown in the presence of GAPDH duplex 5, MAP2K2 duplex 7, and MAP2K1 duplex 4 (5, 7&4); and GAPDH knockdown in the presence of GAPDH, MAP2K2, and MAP2K1 pools consisting of all of the before mentioned duplexes. FIG. 25B shows the MAP2K2 knockdown in the presence of all of the duplex combinations described in FIG. 25A. FIG. 25C shows the MAP2K1 knockdown in the presence of all the duplex combinations described in FIG. 25A. Greater than 75% silencing is achievable for all the GAPDH siRNA tested, even in the presence of competing siRNA directed against MAP2K1 and MAP2K2 targets. Similarly, greater than 75% silencing can be achieved for MAP2K2, even in the presence of siRNAs directed against GAPDH and MAP2K1. For MAP2K1, none of the individual siRNA provided greater than 75% silencing, but pools of MAP2K1 targeting siRNA were able to function adequately (at 1-100 nM) in the presence of pools of siRNA targeting GAPDH and MAP2K2. The compatibility of the invention with multi-gene targeting formats is a significant improvement, and allows users to simplify large genome-wide screens.

Example 32

Some exemplary siRNA sequences to which the foregoing Examples use appear below in Table 2. All sequences refers to the sense strand and are oriented in the 5'→3' direction. All antisense strands are, over the duplex region, presumed to be 100% complementary to the sense strands provided below unless otherwise indicated in the text of the specification above. Any dTdT overhangs are not part of the duplex region. Additional siRNA sequences can be reviewed in Tables I-IV in the incorporated provisional application.

TABLE 2

EXEMPLARY SEQUENCES

| SEQUENCE | siRNA NAME | SEQ. ID NO. |
|---|---|---|
| acagcaaauu ccaucgugu | Cyclo3 | 14 |
| ggccuuagcu acaggagagdt dt | Cyclo14 | 15 |
| ggcuacaaaa acagcaaaudt dt | Cyclo28 | 16 |
| uuccaucgug uaaucaaggdt dt | Cyclo37 | 17 |
| ugguuuacau guuccaauadt dt | gapdh 4 | 18 |
| gaccucaacu acaugguuudt dt | gapdh 3 | 19 |
| gaaaucccau caccaucuudt dt | gapdh 2 | 20 |
| caacggauuu ggucguauudt dt | gapdh 1 | 21 |
| gcacacagcu uacuacaucdt dt | UQCRC1 | 22 |
| gaaaugcccu gguaucucadt dt | UQCRC2 | 23 |
| gaaggaacgu gaugugaucdt dt | UQCRC3 | 24 |
| gagauguggu cuuuaacuadt dt | UQCRC4 | 25 |
| caaccaaagu cgaauaugadt dt | HSPLKSTK1 | 26 |
| gguaucagcu cugugauaadt dt | HSPLKSTK2 | 27 |
| gcaccgaaac cgaguuauudt dt | HSPLKSTK3 | 28 |
| gcacauaccg ccugagucudt dt | HSPLKSTK4 | 29 |
| acagauacaa gaacgugaadt dt | G6PD4 | 30 |
| acaucgccug cguuauccudt dt | G6PD3 | 31 |
| ucacgagucc ugcaugagcdt dt | G6PD2 | 32 |
| auucacgagu ccugcaugadt dt | G6PD1 | 33 |
| ugcugaccuc uguuaccuc | IGF1R-73 | 34 |

Example 31

In one example, a multi-well RTF plate or series of plates can be designed in order to optimize RTF with siRNA. Accordingly, the plates can be configured to include any of the following variables: (1) the concentration of individual or pools of siRNA being between 0.01-250 nM, more preferably between 0.05 and 100 nM, even more preferably between 0.1 and 50 nM, still even more preferably between 0.5 and 25 nM, and most preferably between 0.75 and 10 nM or about 1 nM; (3) the types of polynucleotide carrier being a lipid such as DharmaFECT™ 1, DharmaFECT™ 2, DharmaFECT™ 3, or DharmaFECT™ 4; (3) the concentration of the lipid polynucleotide carrier being at concentrations of 0.05-1 ug per 100 uL of solution, more preferably at concentrations of 0.05-0.5 ug of lipid per 100 uL of solution, even more preferably still at concentrations of 0.05-0.25 ug of lipid per 100 uL of solution, and most preferably at concentrations of 0.05-0.1 ug per 100 uL of solution; (4) the types of media and/or buffer used to complex the lipid being preferably Opti-MEM™, more preferably HyQ-MEM™, and most preferably buffered salt solutions such as Hanks Buffered salt solution or equivalent mixtures; and (5) the types and amounts of cells having densities of 1,000 to 35,000 cells per about 0.3 $cm^2$ to about 0.35 $cm^2$ preferred densities of 2,000-30,000 cells, more preferably 2,000-20,000 cells, even more preferably 2,000-15,000 cells, and most preferably cell densities of 2,000-10,000 cells per about 0.3 $cm^2$ to about 0.35 $cm^2$. The siRNA can be used to study the silencing of selected target genes, or control siRNA can be used to silence known genes in a reproducible manner.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

---

What is claimed is:

1. A reverse transfection apparatus for introducing siRNA into a cell to effect gene silencing, the apparatus comprising:

a well plate having a well for transfecting cells, the well plate being provided in a sealed, sterile package such that the well plate is storable for an extended period of time at a temperature of up to at least 37° C. while maintaining functionality of an siRNA deposited therein, wherein the well is substantially devoid of a cationic polynucleotide carrier selected from the group consisting of lipids, polymers, lipo-polymers, lipid-peptide mixtures, and combinations thereof; and a substantially dry gene silencing composition in the well, the gene silencing composition having at least a first siRNA which silences at least a first target gene, the gene silencing composition being substantially devoid of a cationic polynucleotide carrier selected from the group consisting of lipids, polymers, lipo-polymers, lipid-peptide mixtures, and combinations thereof such that the at least first siRNA in the substantially dry gene silencing composition is capable of being solubilized or suspended in an aqueous medium in an amount sufficient for transfecting cells in the well, the at least first siRNA comprising:

a sense strand having 2'-O-methyl modifications on the first and second 5' nucleotides; and an antisense strand having a 2'-O-methyl modification on the second 5' nucleotide and a 5' end phosphate;

wherein the sense region and the antisense region are capable of forming a duplex of 18-26 base pairs of nucleotides that has at least 80% complementarity over the range of the duplex, and wherein nucleotides of the sense strand and antisense strand other than the first 5' sense nucleotide, the second 5' sense nucleotide, and the second 5' antisense nucleotide are a 2'OH.

2. An apparatus as in claim 1, further comprising a conjugate coupled to the siRNA at the 5' terminal nucleotide or 3' terminal nucleotide on one of the sense strand or antisense strand.

3. An apparatus as in claim 1, wherein the total concentration of siRNA is less than about 100 nM when solubilized or suspended in the aqueous medium.

4. An apparatus as in claim 1, wherein the total concentration of siRNA is less than about 1 nM when solubilized or suspended in the aqueous medium.

5. A kit for introducing siRNA into a cell to effect gene silencing using reverse transfection, the kit comprising:
- a well plate having a well for transfecting cells, the well plate being provided in a sealed, sterile package such that the well plate is storable for an extended period of time at a temperature of up to at least 37° C. while maintaining functionality of an siRNA deposited therein, wherein the well is devoid of a cationic polynucleotide carrier selected from the group consisting of lipids, polymers, lipo-polymers, lipid-peptide mixtures, and combinations thereof, the well plate including:
  - a substantially dry gene silencing composition in the well, the gene silencing composition consisting essentially of at least one ribonucleic acid siRNA configured to silence at least one target gene, the gene silencing composition being disposed in the well such that the siRNA in the substantially dry gene silencing composition is capable of being solubilized or suspended in an aqueous medium in an amount sufficient for transfecting cells in the well, wherein the ribonucleic acid siRNA comprises:
    - (a) a sense strand and an antisense strand, wherein said sense strand and said antisense strand together form an RNA duplex region consisting of 19 base pairs, and wherein the sense strand has 2'-O-alkyl modifications on the first and second 5' nucleotides, and the antisense strand has a 2'-O-alkyl modification on the second 5' nucleotide and a 5' end phosphate and wherein all other nucleotides on the sense and antisense strands are 2' OH; and
    - (b) either zero overhang regions, or one or more overhang regions,
  - wherein each overhang region is two or fewer nucleotides in length;
- an aqueous medium configured for solubilizing or resuspending the substantially dry gene silencing composition; and
- a polynucleotide carrier compound configured to be added to the substantially dry gene silencing composition in the well either before the aqueous medium, with the aqueous medium, or after the aqueous medium in order to facilitate reverse transfection,
- wherein the polynucleotide carrier includes at least one of a lipid, a polymer, a lipo-polymer, or a lipid-peptide mixture.

6. The kit recited in claim 5, the gene silencing composition optionally including at least two ribonucleic acid siRNAs configured to silence the first target gene.

7. The kit recited in claim 5, the gene silencing composition optionally including at least four ribonucleic acid siRNAs configured to silence the first target gene.

8. The kit recited in claim 5, wherein the 2'-O-alkyl modifications are independently selected from the group consisting of 2'-O-methyl, 2'-O-ethyl, 2'-O-propyl, 2'-O-isopropyl, 2'-O-butyl, 2'-O-isobutyl, 2'-O—$CH_2CH_2OCH_3$, 2'-O—$CH_2CH_2OH$, 2'-orthoester, 2'-ACE group orthoester, and combinations thereof.

* * * * *